United States Patent
Velaparthi et al.

(10) Patent No.: US 9,956,220 B2
(45) Date of Patent: May 1, 2018

(54) IMIDAZO-PYRIDAZINE DERIVATIVES AS CASEIN KINASE 1 δ/ε INHIBITORS

(71) Applicant: Bristol-Myers Squibb Company, Princeton, NJ (US)

(72) Inventors: Upender Velaparthi, Cheshire, CT (US); Selvakumar Kumaravel, Bangalore (IN); Arul Mozhi Selvan Subbiah Karupplah, Bangalore (IN); Shilpa Holehatti Maheshwarappa, Karnataka (IN); Chandrasekhar Reddy Rachamreddy, Kadapa (IN); Mark D. Wittman, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 18 days.

(21) Appl. No.: 15/319,028

(22) PCT Filed: Jun. 18, 2015

(86) PCT No.: PCT/US2015/036380
§ 371 (c)(1),
(2) Date: Dec. 15, 2016

(87) PCT Pub. No.: WO2015/195880
PCT Pub. Date: Dec. 23, 2015

(65) Prior Publication Data
US 2017/0137427 A1    May 18, 2017

Related U.S. Application Data

(60) Provisional application No. 62/014,218, filed on Jun. 19, 2014.

(51) Int. Cl.
*A61K 31/5025* (2006.01)
*C07D 487/04* (2006.01)
*C07D 519/00* (2006.01)

(52) U.S. Cl.
CPC ........ *A61K 31/5025* (2013.01); *C07D 487/04* (2013.01); *C07D 519/00* (2013.01)

(58) Field of Classification Search
CPC .................... A61K 31/5025; C07D 487/04
USPC ...................................................... 514/230.5
See application file for complete search history.

(56) References Cited

U.S. PATENT DOCUMENTS 9,475,817 B2 *    5/2016   Velaparthi et al. .. C07D 487/04

FOREIGN PATENT DOCUMENTS

| EP | 2058309 | 5/2009 |
|---|---|---|
| WO | WO 2010/070238 | 6/2010 |
| WO | WO 2014/100533 | 6/2014 |
| WO | WO 2014/100540 | 6/2014 |

OTHER PUBLICATIONS

Shittek and Sinnberg, "Biological functions of casein kinase 1 isoforms and putative roles in tumorigenesis," Molecular Cancer (2014), vol. 13 (231), pp. 1-14.*

* cited by examiner

*Primary Examiner* — Craig D Ricci
*Assistant Examiner* — Janet L. Coppins
(74) *Attorney, Agent, or Firm* — Hong Liu; Elliott Korsen

(57) ABSTRACT

The invention provides compounds of Formula (I) and pharmaceutically-acceptable salts thereof. The compounds of Formula (I) inhibit protein kinase activity thereby making them useful as anticancer agents.

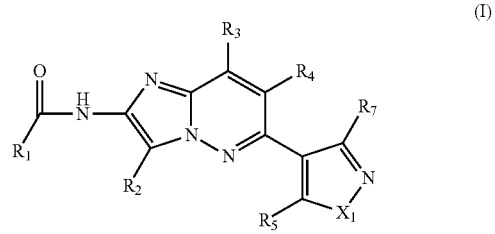

11 Claims, No Drawings

IMIDAZO-PYRIDAZINE DERIVATIVES AS CASEIN KINASE 1 δ/ε INHIBITORS

CROSS REFERENCE TO RELATED APPLICATIONS

This application is entitled to priority pursuant to 35 U.S.C. § 119(e) to U.S. provisional patent application No. 62/014,218, filed on Jun. 19, 2014, which is incorporated herein in its entirety.

FIELD OF THE INVENTION

The invention relates to novel substituted bicyclic pyrazoles useful as protein kinase inhibitors. This invention also relates to methods of using the compounds in the treatment of proliferative and other types of diseases and to pharmaceutical compositions containing the compounds.

BACKGROUND OF THE INVENTION

The invention relates to substituted bicyclic pyrazole compounds which inhibit protein kinase enzymes, compositions which contain protein kinase inhibiting compounds and methods of using inhibitors of protein kinase enzymes to treat diseases which are characterized by an overexpression or upregulation of protein kinases. Protein kinases mediate intracellular signal transduction by affecting a phosphoryl transfer from a nucleoside triphosphate to a protein acceptor that is involved in a signaling pathway. There are a number of kinases and pathways through which extracellular and other stimuli cause a variety of cellular responses to occur inside the cell. An extracellular stimulus may affect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Serine/threonine kinases are a class of protein kinases that are among the most promising drug targets for future small molecule inhibitors. Inhibition of serine/threonine kinases is likely to have relevance to the treatment of cancer, diabetes and a variety of inflammatory disorders. The successful development of GLEEVEC® as a Bcr/Abl protein kinase inhibitor has provided further evidence that protein kinases are valid drug targets for potential cancer therapies.

Casein kinase 1 (CK1) belongs to the serine/threonine kinase family. In mammals, the enzyme exists in seven isozymic forms: α, β, γ1, γ2, γ3, δ, and ε. By phosphorylating different substrate proteins, these isoforms are able to activate, inactivate, stabilize, or destabilize the functions of the proteins, regulating the functions of various types of different organisms. For example, a tumor suppressor factor p53 and an oncogene mdm2, which are both important proteins for controlling abnormal cell growth, are substrates of casein kinase 1.

Mammalian casein kinase 1δ and casein kinase 1ε are key regulators of diverse cellular growth and survival processes including Wnt signaling, DNA repair and circadian rhythms. They have a kinase domain that is similar to those of other isoforms. However, the N-terminal and C-terminal domains thereof are different from those of other isoforms. The C-terminal domain has a plurality of autophosphorylation sites, and it is considered to be involved in regulation of autoenzyme activity. Phosphorylation of p53 by casein kinase 1δ or casein kinase 1ε leads to a consequent change in the interaction between p53 and mdm2. It has also been known that casein kinase 1ε or casein kinase 1δ is involved in a regulatory protein associated with the formation of a spindle as a central body during cell division, and that the casein kinase 1δ or casein kinase 1ε is involved in apoptosis mediated by TRAIL (tumor necrosis factor-related apoptosis inducing factor) and Fas. It has been further reported that inhibition of casein kinase 1ε or casein kinase 1δ by a nonselective casein kinase 1 inhibitory compound IC261 reduces pancreatic tumor cell growth in vitro and in vivo (Brockschmidt et al., *Gut*, 57(6):799-806 (2008)). Hence, a medicament inhibiting the function of casein kinase 1δ or casein kinase 1ε would be expected to exert important phenotypic and therapeutic effects broadly in development and disease, especially cancer.

The present invention relates to a new class substituted bicyclic pyrazoles found to be effective in inhibiting casein kinase 1δ or casein kinase 1ε. These novel compounds are provided to be useful as pharmaceuticals with desirable stability, bioavailability, therapeutic index and toxicity values that are important to their drugability.

SUMMARY OF THE INVENTION

The invention is directed to substituted bicyclic pyrazole compounds of Formulae (I)-(VII) or stereoisomers, tautomers, pharmaceutically-acceptable salts, solvates or prodrugs thereof, which inhibit protein kinase enzymes, especially protein kinase CK1 for the treatment of cancer.

The present invention also provides processes and intermediates for making the compounds of the present invention or stereoisomers, tautomers, pharmaceutically-acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically-acceptable salts, solvates, or prodrugs thereof.

The present invention also provides methods for inhibiting the activity of protein kinase CK1 comprising administering to a host in need of such treatment a therapeutically effective amount of at least one of the compounds of the present invention or stereoisomers, tautomers, pharmaceutically-acceptable salts, solvates, or prodrugs thereof.

The present invention also provides methods for treating cancers comprising administering to a host in need of such treatment a therapeutically effective amount of at least one of the compounds of the present invention or stereoisomers, tautomers, pharmaceutically-acceptable salts, solvates, or prodrugs thereof.

The present invention also provides the compounds of the present invention or stereoisomers, tautomers, pharmaceutically-acceptable salts, solvates, or prodrugs thereof, for use in therapy.

The present invention also provides the use of the compounds of the present invention or stereoisomers, tautomers, pharmaceutically-acceptable salts, solvates, or prodrugs thereof, in preparing a medicament for the treatment of cancer in a human patient, particularly a cancer receptive to treatment via inhibition of the CK1 enzyme.

These and other features of the invention will be set forth in the expanded form as the disclosure continues.

DETAILED DESCRIPTION OF THE INVENTION

The invention provides for novel substituted pyrazole compounds useful as therapeutic agents, pharmaceutical compositions employing such novel compounds and for methods of using such compounds.

In accordance with the invention, there are disclosed compounds of Formula (I) including enantiomers, diastereomers, tautomers, pharmaceutically-acceptable salts, prodrugs, hydrates, or solvates thereof,

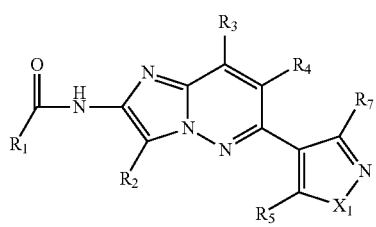

(I)

wherein:

$X_1$ is selected from O and $NR_6$; provided when X is $NR_6$, $R_5$ and $R_6$ together with the nitrogen atom and the adjacent carbon atom to which they are respectively attached form a heterocyclic ring comprising carbon atoms and zero to 3 additional heteroatoms selected from N, $NR_8$, O, S and substituted with 1-5 $R_{10}$;

$R_1$ is selected from $C_{1-4}$alkyl (optionally substituted with F, Cl, Br, OH, CN, and $NR_aR_a$), $-(CR_dR_d)_r$-carbocyclyl substituted with 0-5 $R_{11}$, and $-(CR_dR_d)_r$-heterocyclyl comprising carbon atoms and 1 to 4 heteroatoms selected from N, $NR_9$, O, S, and substituted with 0-5 $R_{11}$;

$R_2$ is selected from H, $C_{1-4}$alkyl, F, Cl, Br, CN, aryl, and heteroaryl;

$R_3$ is selected from H and $C_{1-4}$alkyl;

$R_4$ is selected from H, $C_{1-4}$alkyl F, Cl, Br, and CN;

$R_5$ is selected from H, $C_{1-4}$alkyl substituted with 0-4 $R_e$, $-(CH_2)_r-C_{3-6}$ carbocyclyl substituted with 0-4 $R_e$, and $-(CH_2)_r$-heterocyclyl comprising carbon atoms and 1 to 3 heteroatoms selected from N, O, S, and substituted with 0-4 $R_e$;

$R_7$ is aryl substituted with 0-3 $R_e$;

$R_8$ is selected from H, $C_{1-4}$ alkyl substituted with 0-3 $R_e$, $-(CH_2)_rCN$, $-(CH_2)_rOR_b$, $(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rC(=O)-C_{1-4}$ alkyl substituted with 0-3 $R_e$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_2NR_aR_a$, $-(CH_2)_rNR_aS(O)_2NR_aR_a$, $-(CH_2)_rNR_aS(O)_2R_c$, $(CH_2)_r$-carbocyclyl substituted with 0-3 $R_e$, and $-(CH_2)_r$-heterocyclyl substituted with 0-3 $R_e$;

$R_9$ is selected from H, $-C(=O)R_b$, $C_{1-6}$ alkyl substituted with 0-5 $R_e$, $-(CH_2)_r-C_{3-6}$carbocyclyl substituted with 0-5 $R_e$, and $-(CH_2)_r$-heterocyclyl substituted with 0-5 $R_e$;

$R_{10}$ is selected from H, $C_{1-6}$alkyl substituted with 0-3 $R_e$, $-(CH_2)_rNR_aR_a$, $-(CH_2)_rC(=O)R_b$, $-(CH_2)_rC(=O)OR_b$, $-(CH_2)_rC(=O)NR_aR_a$, $S(O)_pR_c$, $(CH_2)_r-C_{3-6}$ carbocyclyl substituted with 0-3 $R_e$, and $-(CH_2)_r$-heterocyclyl substituted with 0-3 $R_e$;

$R_{11}$, at each occurrence, is independently selected from H, F, Cl, Br, =O, CN, $NO_2$, $-OR_b$, $-S(O)_pR_c$, $-C(=O)R_b$, $-(CR_dR_d)_rNR_aR_a$, $-(CR_dR_d)_rC(=O)NR_aR_a$, $-NR_aC(=O)R_b$, $-NR_aC(=O)OR_b$, $-OC(=O)NR_aR_a$, $-NR_aC(=O)NR_aR_a$, $-(CR_dR_d)_rC(=O)OR_b$, $-S(O)_2NR_aR_a$, $-NR_aS(O)_2NR_aR_a$, $-NR_aS(O)_2R_c$, $C_{1-6}$ alkyl substituted with 0-5 $R_e$, $-(CR_dR_d)_r-C_{3-6}$carbocyclyl substituted with 0-5 $R_e$, and $-(CR_dR_d)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl substituted with 0-5 $R_e$, and heterocyclyl substituted with 0-5 $R_e$;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, F, Cl, Br, CN, $NO_2$, =O, $CO_2H$, $-(CH_2)_rOR_f$, $SR_f$, and $-(CH_2)_rNR_fR_f$;

$R_f$, at each occurrence, is independently selected from H, F, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another aspect, there are disclosed compounds of Formula (II) including enantiomers, diastereomers, tautomers, pharmaceutically-acceptable salts, prodrugs, hydrates, or solvates thereof,

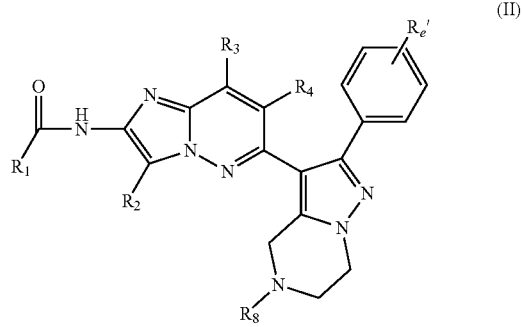

(II)

wherein:

$R_1$ is selected from aryl, cycloalkyl, and heterocyclyl selected from pyridyl, pyrimidinyl, pyrazinyl, pyridazinyl, triazinyl, furyl, quinolinyl, quinoxalinyl, dihydroquinolinyl, tetrahydroquinolinyl, tetrahydropyranyl, isoquinolinyl, thienyl, imidazolyl, thiazolyl, indolyl, pyrrolyl, oxazolyl, benzofuryl, benzothienyl, benzothiazolyl, benzoxazinyl, isoxazolyl, pyrazolyl, triazolyl, tetrazolyl, indazolyl, 1,2,3-thiadiazolyl, 1,2,4-thiadiazolyl, isothiazolyl, purinyl, carbazolyl, benzimidazolyl, indolinyl, benzodioxolanyl, benzodioxane, 1,5-naphthyridinyl, imidazopyridinyl, azetidinyl, pyrrolidinyl, piperidinyl, piperazinyl, and morpholinyl, each substituted with 0-4 $R_{11}$;

$R_2$ is selected from H, $C_{1-4}$alkyl, F, Cl, Br, CN, aryl, and heteroaryl;

$R_3$ is selected from H and $C_{1-4}$alkyl;

$R_4$ is selected from H, $C_{1-4}$alkyl F, Cl, Br, and CN; $R_e'$ is selected from F, Cl, Br, and $C_{1-6}$ alkyl substituted with 0-5 $R_f$;

$R_8$ is selected from H, $C_{1-4}$ alkyl substituted with 0-3 $R_e$—S(O)$_p R_c$, —C(=O)$R_b$, —C(=O)NR$_a$R$_a$, —C(=O)(CH$_2$)$_r$NR$_a$R$_a$, —(CH$_2$)$_r$C(=O)OR$_b$, —S(O)$_2$NR$_a$R$_a$, $C_{3-6}$ carbocyclyl substituted with 0-3 $R_e$, and heterocyclyl substituted with 0-3 $R_e$;

$R_{11}$, at each occurrence, is independently selected from H, F, Cl, Br, =O, CN, NO$_2$, —OR$_b$, —S(O)$_p R_c$, —C(=O)$R_b$, —(CH$_2$)$_r$NR$_a$R$_a$, —(CH$_2$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CH$_2$)$_r$C(=O)OR$_b$, $C_{1-6}$ alkyl substituted with 0-5 $R_e$, —(CH$_2$)$_r$—$C_{3-6}$carbocyclyl substituted with 0-5 $R_e$, and —(CH$_2$)$_r$-heterocyclyl substituted with 0-5 $R_e$; and other variables are as defined in Formula (I) above.

In another embodiment, there are disclosed compounds of Formula (III) including enantiomers, diastereomers, tautomers, pharmaceutically-acceptable salts, prodrugs, hydrates, or solvates thereof,

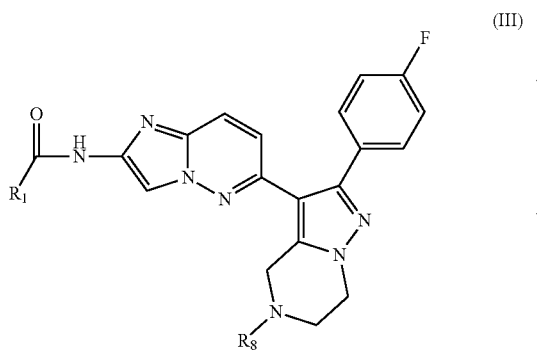

(III)

wherein:
$R_1$ is selected from

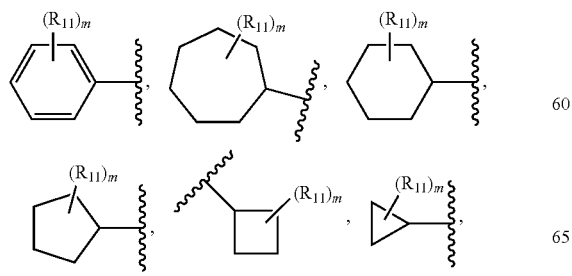

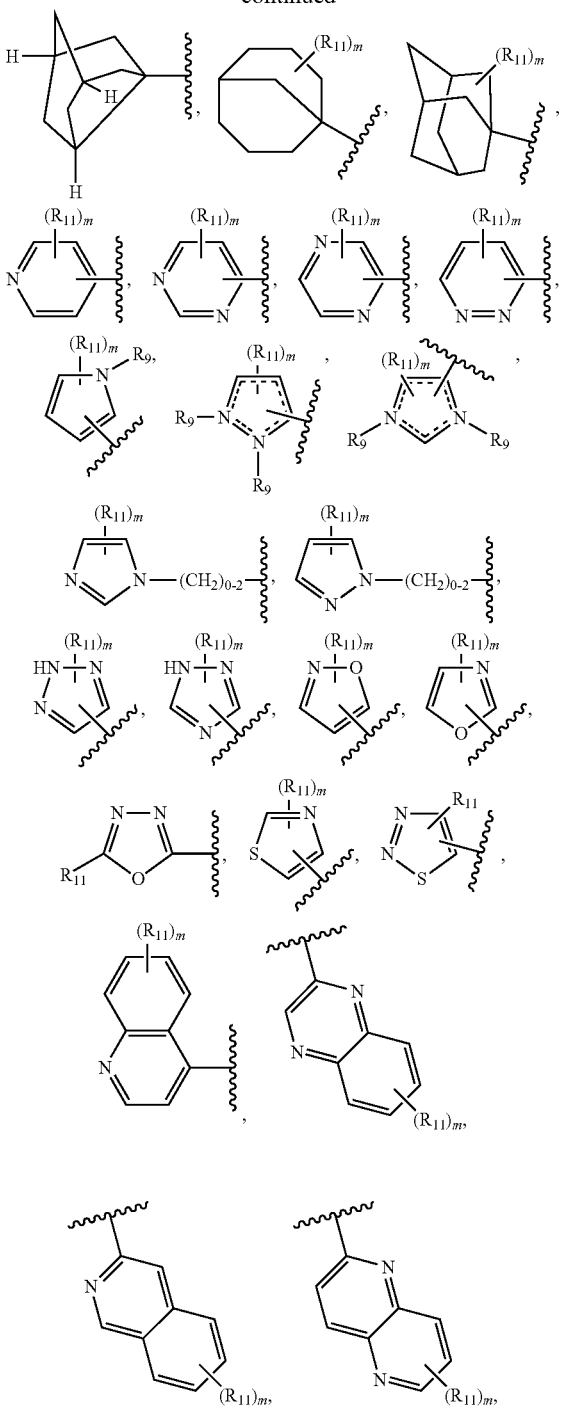

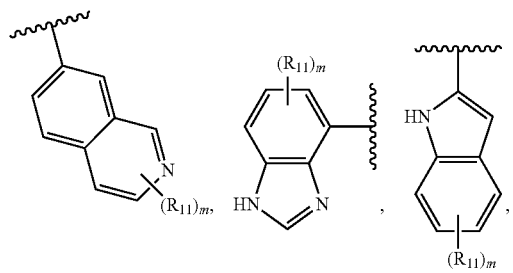

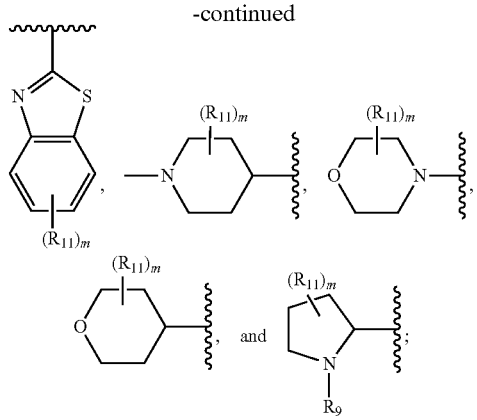

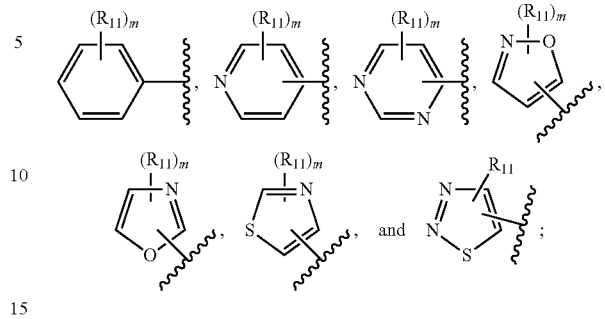

---- represents an optional bond;

$R_8$ is selected from H, $C_{1-4}$ alkyl substituted with 0-3 $R_e$, —S(O)$_p R_c$, —C(=O)$R_b$, —C(=O)NR$_a$R$_a$, —C(=O)(CH$_2$)$_r$NR$_a$R$_a$, —C(=O)OR$_b$, —S(O)$_2$NR$_a$R$_a$, $C_{3-6}$ carbocyclyl substituted with 0-3 $R_e$, and heterocyclyl substituted with 0-3 $R_e$;

$R_9$, at each occurrence, is independently selected from H, —C(=O)$R_b$, and $C_{1-6}$ alkyl substituted with 0-5 $R_e$;

$R_{11}$, at each occurrence, is independently selected from H, F, Cl, Br, =O, CN, —OR$_b$, —C(=O)R$_b$, —(CH$_2$)$_r$NR$_a$R$_a$, —(CH$_2$)$_r$C(=O)NR$_a$R$_a$, —NR$_a$C(=O)R$_b$, —(CH$_2$)$_r$C(=O)OR$_b$, $C_{1-6}$ alkyl substituted with 0-5 $R_e$, —(CH$_2$)$_r$—$C_{3-6}$carbocyclyl substituted with 0-5 $R_e$, and —(CH$_2$)$_r$-heterocyclyl substituted with 0-5 $R_e$;

$R_a$, at each occurrence, is independently selected from H, $C_{1-6}$ alkyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl substituted with 0-5 $R_e$, and heterocyclyl substituted with 0-5 $R_e$;

$R_e$, at each occurrence, is independently selected from $C_{1-6}$ alkyl substituted with 0-5 $R_f$, —(CH$_2$)$_r$—$C_{3-6}$ cycloalkyl, F, Cl, Br, CN, NO$_2$, =O, CO$_2$H, —(CH$_2$)$_r$OC$_{1-5}$alkyl, —(CH$_2$)$_r$OH, SH, and —(CH$_2$)$_r$NR$_f$R$_f$;

$R_f$, at each occurrence, is independently selected from H, F, $C_{1-5}$ alkyl, and phenyl, or $R_f$ and $R_f$ together with the nitrogen atom to which they are both attached form a heterocyclic ring; and m, at each occurrence, is independently selected from zero, 1, and 2.

In another embodiment, there are disclosed compounds of Formula (III) including enantiomers, diastereomers, tautomers, pharmaceutically-acceptable salts, prodrugs, hydrates, or solvates thereof, wherein:

$R_1$ is selected from $R_8$ is selected from H, $C_{1-4}$alkyl substituted with 0-3 $R_e$, —C(=O)$C_{1-4}$alkyl substituted with 0-3 $R_e$, —C(=O)-aryl substituted with 0-3 $R_e$, —C(=O)-heteroaryl substituted with 0-3 $R_e$, —C(=O)CH$_2$CN, $C_{3-6}$ cycloalkyl, heterocyclyl substituted with 0-3 $R_e$, —C(=O)OC$_{1-4}$alkyl substituted with 0-3 $R_e$, S(O)$_2$—$C_{1-4}$alkyl substituted with 0-3 $R_e$, S(O)$_2$—$C_{3-6}$ cycloalkyl substituted with 0-3 $R_e$, S(O)$_2$—(CH$_2$)$_r$-aryl substituted with 0-3 $R_e$, S(O)$_2$-heteroaryl substituted with 0-3 $R_e$, C(=O)NHC$_{1-4}$alkyl substituted with 0-3 $R_e$, C(=O)NHC$_{3-6}$ cycloalkyl substituted with 0-3 $R_e$, C(=O)NH-admantanyl, C(=O)NH-aryl substituted with 0-3 $R_e$, and C(=O)NH-heteroaryl substituted with 0-3 $R_e$;

$R_{11}$, at each occurrence, is independently selected from H, F, —NR$_a$R$_a$, $C_{1-6}$ alkyl substituted with 0-5 $R_e$, —(CH$_2$)$_r$—$C_{3-6}$carbocyclyl substituted with 0-5 $R_e$, and —(CH$_2$)$_r$-heterocyclyl substituted with 0-5 $R_e$;

$R_a$, at each occurrence, is independently selected from H, $C_{1-6}$ alkyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_e$, at each occurrence, is independently selected from $C_{1-6}$ alkyl substituted with 0-5 $R_f$, —(CH$_2$)$_r$—$C_{3-6}$ cycloalkyl, F, Cl, Br, CN, NO$_2$, =O, CO$_2$H, —(CH$_2$)$_r$OC$_{1-5}$alkyl, —(CH$_2$)$_r$OH, SH, and —(CH$_2$)$_r$NR$_f$R$_f$;

$R_f$, at each occurrence, is independently selected from H, F, $C_{1-5}$ alkyl;

m, at each occurrence, is independently selected from zero, 1, and 2; and other variables are as defined in Formula (III) above.

In another embodiment, there are disclosed compounds of formula (IV) including enantiomers, diastereomers, tautomers, pharmaceutically-acceptable salts, prodrugs, hydrates, or solvates thereof,

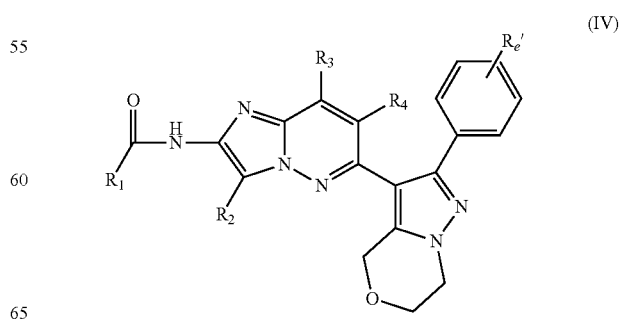

wherein:

$R_1$ is selected from carbocyclyl substituted with 0-5 $R_{11}$ and heteroaryl comprising carbon atoms and 1 to 4 heteroatoms selected from N, $NR_9$, O, S, and substituted with 0-5 $R_{11}$;

$R_2$ is selected from H, $C_{1-4}$alkyl, F, C, Br, CN, aryl, and heteroaryl;

$R_3$ is selected from H and $C_{1-4}$alkyl;

$R_4$ is selected from H, $C_{1-4}$alkyl F, Cl, Br, and CN;

$R_e'$ is selected from F, Cl, and Br;

$R_9$, at each occurrence, is independently selected from H, —C(=O)$R_b$, and $C_{1-6}$ alkyl substituted with 0-5 $R_e$;

$R_{11}$, at each occurrence, is independently selected from H, F, Cl, CN, —$OR_b$, —$(CH_2)_rNR_aR_a$, —$NR_aC(=O)R_b$, $C_{1-6}$ alkyl substituted with 0-5 $R_e$, —$(CH_2)_r$—$C_{3-6}$carbocyclyl substituted with 0-5 $R_e$, and —$(CH_2)_r$-5- to 10-membered heterocyclyl substituted with 0-5 $R_e$;

$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, —$(CH_2)_r$—$C_{3-6}$cycloalkyl, F, Cl, Br, CN, $NO_2$, =O, $CO_2H$, —$(CH_2)_rOC_{1-5}$alkyl, —$(CH_2)_rOH$, $S(O)_2C_{1-4}$alkyl, and —$(CH_2)_rNR_fR_f$;

$R_f$, at each occurrence, is independently selected from H, $C_{1-5}$ alkyl, and phenyl, or $R_f$ and $R_f$ together with the nitrogen atom to which they are both attached form a heterocyclic ring; and r, at each occurrence, is independently selected from zero, 1, 2, 3, and 4.

In another embodiment, there are disclosed compounds of Formula (IV) including enantiomers, diastereomers, tautomers, pharmaceutically-acceptable salts, prodrugs, hydrates, or solvates thereof, wherein:

$R_1$ is selected from

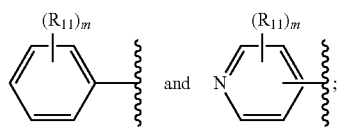

$R_{11}$, at each occurrence, is independently selected from F, Cl, —$NR_aR_a$, OH, $OC_{1-4}$alkyl, $C_{1-4}$ alkyl substituted with 0-5 $R_e$,

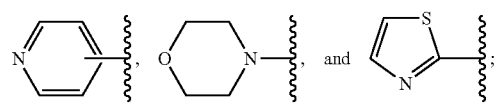

$R_a$, at each occurrence, is independently selected from H and $C_{1-4}$ alkyl substituted with 0-5 $R_e$;

$R_e$, at each occurrence, is independently selected from $C_{1-6}$ alkyl F, Cl, Br, CN, and $NH_2$;

m, at each occurrence, is independently selected from zero, 1, and 2; and other variables are as defined in Formula (IV) above.

In another embodiment, there are disclosed compounds of Formula (V) including enantiomers, diastereomers, tautomers, pharmaceutically-acceptable salts, prodrugs, hydrates, or solvates thereof,

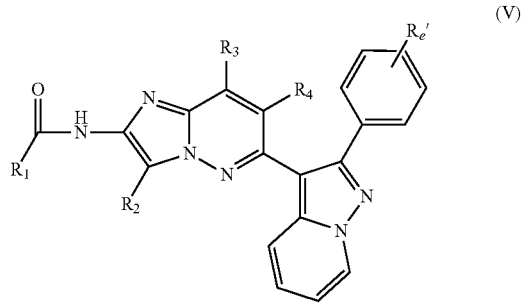

wherein:

$R_1$ is selected from carbocyclyl substituted with 0-5 $R_{11}$ and heteroaryl comprising carbon atoms and 1 to 4 heteroatoms selected from N, O, S, and substituted with 0-5 $R_{11}$;

$R_2$ is selected from H, $C_{1-4}$alkyl, F, Cl, Br, CN, aryl, and heteroaryl;

$R_3$ is selected from H and $C_{1-4}$alkyl;

$R_4$ is selected from H, $C_{1-4}$alkyl F, Cl, Br, and CN;

$R_e'$ is selected from F, Cl, and Br;

$R_{11}$, at each occurrence, is independently selected from H, F, —$NR_aR_a$, $C_{1-6}$ alkyl substituted with 0-5 $R_e$, —$(CH_2)_r$—$C_{3-6}$carbocyclyl substituted with 0-5 $R_e$, and —$(CH_2)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOR_f$, $SR_f$, and —$(CH_2)_rNR_fR_f$;

$R_f$, at each occurrence, is independently selected from H, F, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another embodiment, there are disclosed compounds of Formula (VI) including enantiomers, diastereomers, tautomers, pharmaceutically-acceptable salts, prodrugs, hydrates, or solvates thereof,

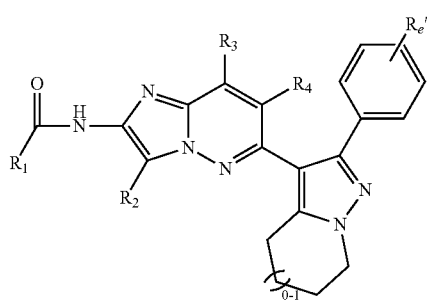

(VI)

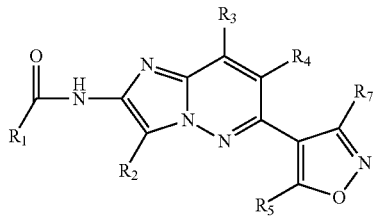

(VII)

wherein:

$R_1$ is selected from carbocyclyl substituted with 0-5 $R_{11}$ and heterocyclyl comprising carbon atoms and 1 to 4 heteroatoms selected from N, $NR_9$, O, S, and substituted with 0-5 $R_{11}$;

$R_2$ is selected from H, $C_{1-4}$alkyl, F, Cl, Br, CN, aryl, and heteroaryl;

$R_3$ is selected from H and $C_{1-4}$alkyl;

$R_4$ is selected from H, $C_{1-4}$alkyl F, Cl, Br, and CN;

$R_e{'}$ is selected from F, Cl, and Br;

$R_9$, at each occurrence, is independently selected from H, —C(=O)$R_b$, and $C_{1-6}$ alkyl substituted with 0-5 $R_e$;

$R_{11}$, at each occurrence, is independently selected from H, F, —$NR_aR_a$, $C_{1-6}$ alkyl substituted with 0-5 $R_e$, —(CH$_2$)$_r$—$C_{3-6}$carbocyclyl substituted with 0-5 $R_e$, and —(CH$_2$)$_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;

$R_e$, at each occurrence, is independently selected from $C_{1-6}$ alkyl substituted with 0-5 $R_f$, —(CH$_2$)$_r$—$C_{3-6}$ cycloalkyl, F, Cl, Br, CN, NO$_2$, =O, CO$_2$H, —(CH$_2$)$_r$OR$_f$, SR$_f$, and —(CH$_2$)$_r$NR$_f$R$_f$;

$R_f$, at each occurrence, is independently selected from H, F, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl; and r, at each occurrence, is independently selected from zero, 1, 2, 3, and 4.

In another embodiment, there are disclosed compounds of Formula (VII) including enantiomers, diastereomers, tautomers, pharmaceutically-acceptable salts, prodrugs, hydrates, or solvates thereof, wherein:

$R_1$ is selected from carbocyclyl substituted with 0-5 $R_{11}$ and heterocyclyl comprising carbon atoms and 1 to 4 heteroatoms selected from N, $NR_9$, O, S, and substituted with 0-5 $R_{11}$;

$R_2$ is selected from H, $C_{1-4}$alkyl, F, Cl, Br, CN, aryl, and heteroaryl;

$R_3$ is selected from H and $C_{1-4}$alkyl;

$R_4$ is selected from H, $C_{1-4}$alkyl F, Cl, Br, and CN;

$R_5$ is selected from H, $C_{1-4}$alkyl substituted with 0-4 $R_e$, —(CH$_2$)$_r$—$C_{3-6}$ carbocyclyl substituted with 0-4 $R_e$, and —(CH$_2$)$_r$-heterocyclyl comprising carbon atoms and 1 to 3 heteroatoms selected from N, O, S, and substituted with 0-4 $R_e$;

$R_7$ is aryl substituted with 0-3 $R_e$;

$R_9$ is selected from H, —C(=O)$R_b$, $C_{1-6}$ alkyl substituted with 0-5 $R_e$, —(CH$_2$)$_r$—$C_{3-6}$carbocyclyl substituted with 0-5 $R_e$, and —(CH$_2$)$_r$-heterocyclyl substituted with 0-5 $R_e$;

$R_{11}$, at each occurrence, is independently selected from H, F, —$NR_aR_a$, $C_{1-6}$ alkyl substituted with 0-5 $R_e$, —(CH$_2$)$_r$—$C_{3-6}$carbocyclyl substituted with 0-5 $R_e$, and —(CH$_2$)$_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;

$R_e$, at each occurrence, is independently selected from $C_{1-6}$ alkyl substituted with 0-5 $R_f$, —(CH$_2$)$_r$—$C_{3-6}$ cycloalkyl, F, Cl, Br, CN, NO$_2$, =O, CO$_2$H, —(CH$_2$)$_r$OR$_f$, SR$_f$, and —(CH$_2$)$_r$NR$_f$R$_f$;

$R_f$ at each occurrence, is independently selected from H, F, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl; and r, at each occurrence, is independently selected from zero, 1, 2, 3, and 4.

All aspects of the compounds, including individual variable definitions, may be combined with other aspects to form additional compounds. For example, in one embodiment of Formula (I), $R_1$ is heteroaryl and $R_5$ and $R_6$ together form a heterocyclic ring comprising carbon atoms. In another embodiment, $R_1$ is heteroaryl and $R_5$ and $R_6$ together form a heterocyclic ring comprising carbon atoms and a nitrogen atom. In still another embodiment, $R_1$ is heteroaryl and $R_1$ is heteroaryl and $R_5$ and $R_6$ together form a heterocyclic ring comprising carbon atoms and an oxygen atom.

The compounds of Formulae (I)-(VII) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for Formulae (I)-(VII) may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

The present invention is also intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the Formulae (I)-(VII) may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) Bundgaard, H., ed., *Design of Prodrugs*, Elsevier (1985);

b) Widder, K. et al., eds., *Methods in Enzymology*, 112: 309-396, Academic Press (1985);

c) Bundgaard, H., Chapter 5, "Design and Application of Prodrugs", *A Textbook of Drug Design and Development*, pp. 113-191, Krosgaard-Larsen, P. et al., eds., Harwood Academic Publishers (1991); and d) Bundgaard, H., *Adv. Drug Deliv. Rev.*, 8:1-38 (1992).

It should further be understood that solvates (e.g., hydrates) of the compounds of Formulae (I)-(VII) are also within the scope of the invention. Methods of solvation are generally known in the art. The inventive compounds may either be in the free or hydrate form.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

Definitions

The following are definitions of terms used in this specification and appended claims. The initial definition provided for a group or term herein applies to that group or term throughout the specification and claims, individually or as part of another group, unless otherwise indicated.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

As used herein, the term "alkyl" or "alkylene" is intended to include both branched and straight-chain saturated aliphatic hydrocarbon groups having the specified number of carbon atoms. For example, "C$_{1-10}$ alkyl" (or alkylene), is intended to include C$_1$, C$_2$, C$_3$, C$_4$, C$_5$, C$_6$, C$_7$, C$_8$, C$_9$, and C$_{10}$ alkyl groups. Additionally, for example, "C$_1$-C$_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "halogen" or "halo" refers to fluorine (F), chlorine (Cl), bromine (Br) and iodine.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle", "carbocyclic residue", or "carbocyclyl" is intended to mean any stable 3-, 4-, 5-, 6-, or 7-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle", "carbocyclic residue", or "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The term "aryl" refers to monocyclic, bicyclic, tricyclic aromatic hydrocarbon groups having 6 to 15 carbon atoms in the ring portion, such as phenyl, naphthyl, biphenyl and diphenyl groups, each of which may be substituted. Aryl groups which are bicyclic or tricyclic must include at least one fully aromatic ring but the other fused ring or rings may be aromatic or non-aromatic. When an aryl is substituted with a further heterocyclic ring, said ring may be attached to the aryl through a carbon atom or a heteroatom and said ring in turn is optionally substituted with one to two substituents as valence allows.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "cycloalkyl" refers to an optionally substituted, saturated cyclic hydrocarbon ring systems, preferably containing 1 to 3 rings and 3 to 7 carbons per ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

As used herein, the term "heterocycle", "heterocyclyl", "heterocyclic ring" or "heterocyclic group" is intended to mean a stable 4-, 5-, 6-, or 7-membered monocyclic or bicyclic or 7-, 8-, 9-, 10-, 11-, 12-, 13-, or 14-membered bicyclic heterocyclic ring which is saturated, partially unsaturated or fully unsaturated or aromatic, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on a carbon atom or on a nitrogen atom if the resulting compound is stable. A nitrogen atom in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle", "heterocyclyl", "heterocyclic ring" or "heterocyclic group" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, dihydroisoquinolinyl, tetrahydroquinolinyl, isoquinolinyl, benzimidazolyl, benzopyranyl, benzoxazinyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and the like.

Exemplary tricyclic heteroaryl groups include carbazolyl, benzidolyl, phenanthrollinyl, acridinyl, phenanthridinyl, xanthenyl and the like.

The term "heteroatoms" shall include oxygen, sulfur and nitrogen.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

When any variable occurs more than one time in any constituent or formula for a compound, its definition at each occurrence is independent of its definition at every other occurrence. Thus, for example, if a group is shown to be substituted with 0-3 $R_e$, then said group may optionally be substituted with up to three $R_e$ groups and $R_e$ at each occurrence is selected independently from the definition of $R_e$. Also, combinations of substituents and/or variables are permissible only if such combinations result in stable compounds.

Utility

The compounds of the invention may be used to modulate kinase activities.

Applicants have discovered that compounds of Formulae (I)-(VII) have particular utility in treating conditions associated with the modulation of serine/threonine kinase activity, especially that of casein kinase 1δ or casein kinase 1ε. The diseases, with the pathological conditions of which the activation mechanism of casein kinase 1δ or casein kinase 1ε associated, are not limited. Examples of such diseases include circadian rhythm disorder (including sleep disorder), neurodegenerative disease, and proliferative disorder (cancer).

In the present specification, the type of circadian rhythm disorder is not limited. The circadian rhythm disorder includes mood disorder and sleep disorder. Such sleep disorder is circadian rhythm sleep disorder, and the circadian rhythm sleep disorder includes a disease selected from the group consisting of shift work sleep disorder, jet lag syndrome, advanced sleep phase syndrome, and delayed sleep phase syndrome.

Moreover, the sleep disorder includes a disease selected from the group consisting of insomnia, sleep-related breathing disorder, central hypersomnia, parasomnia, and sleep-related movement disorder. Furthermore, the above-described mood disorder is selected from either depressive disorder or bipolar disorder, and the depressive disorder is major depressive disorder. Further, the mood disorder is selected from either depressive disorder or bipolar disorder, and the bipolar disorder is selected from the group consisting of bipolar type-I disorder or bipolar type-II disorder. Still further, examples of the disease in the present invention include insomnia, sleep-related breathing disorder, central hypersomnia, circadian rhythm sleep disorder, parasomnia, sleep-related movement disorder, and sleep disorder caused by other reasons.

In the present specification, insomnia includes psychophysiologic insomnia caused by stress or the like, insomnia caused by medical disease, and the like. Sleep-related breathing disorder includes central sleep apnea syndrome, obstructive sleep apnea syndrome, sleep-related hypoventilation/anoxemia syndrome, and the like. Central hypersomnia includes narcolepsy, idiopathic hypersomnia, recurrent hypersomnia, and the like. Circadian rhythm sleep disorder includes shift work sleep disorder, jet lag syndrome, advanced sleep phase syndrome, delayed sleep phase syndrome, and the like. Parasomnia includes sleep walking, REM sleep behavior disorder, and the like. Sleep-related movement disorder includes restless legs syndrome, periodic limb movement disorder, and the like.

In the present specification, the type of neurodegenerative disease is not limited, Examples of central neurodegenerative disease include: neurodegenerative disease caused by Alzheimer's disease, Parkinson's disease or Down's syndrome; nerve degeneration caused by physical nerve damage (brain tissue damage such as brain contusion, and nerve damage caused by head injury and the like); and nerve degeneration caused by nerve damage occurred after ischemia or ischemic reperfusion include: stroke, cerebral infarction, cerebral hemorrhage, cerebral ischemia, subarachnoid hemorrhage, aneurysmal hemorrhage, myocardial infarction, hypoxia, anoxia and nerve damage caused by grand mal/cerebral ischemia.

The compounds of the present invention can be used to treat proliferative disorders associated with abnormal kinase activity. As used herein, the terms "treating" and "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

Accordingly, one aspect of the invention is the use of a compound of the Formulae (I)-(VII), or a pharmaceutically-acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of Formulae (I)-(VII) or a pharmaceutically-acceptable salt thereof as defined herein before.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. Compounds of Formulae (I)-(VII) may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, aminoglutethimide, estramustine, medroxyprogesteroneacetate, leuprolide, flutamide, toremifene, ZOLADEX®; matrix metalloproteinase inhibitors; VEGF inhibitors, such as anti-VEGF antibodies (AVASTIN®) and small molecules such as ZD6474 and SU6668; Vatalanib, BAY-43-9006, SU11248, CP-547632, and CEP-7055; HER 1 and HER 2 inhibitors including anti-HER$_2$ antibodies (HERCEPTIN®); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g., GLEEVEC® and dasatinib; CASODEX® (bicalutamide, Astra Zeneca), Tamoxifen; MEK-1 kinase inhibitors, MAPK kinase inhibitors, PI3 kinase inhibitors; PDGF inhibitors, such as imatinib; antiangiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo [14.1.0] heptadecane-5,9-dione (ixabepilone), [1S-[1R*,3R*(E), 7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; other CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g., 6-thioguanine and 6-mercaptopurine; glutamine antagonists, e.g., DON (AT-125; d-oxonorleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein may be surgery, radiotherapy or chemotherapy. Such chemotherapy may cover three main categories of therapeutic agent:

(i) antiangiogenic agents that work by different mechanisms from those defined herein before (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), famesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as AVASTIN® (bevacizumab) and ERBITUX® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); intercalating antitumor antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide, nitrosoureas, thiotepa; antimitotic agents (for example, vinca alkaloids like vincristine, vinorelbine, vinblastine and vinflunine) and taxoids such as TAXOL® (paclitaxel), Taxotere (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as VELCADE® (bortezomib).

As stated above, the Formulae (I)-(VII) compounds of the invention are of interest for their antiproliferative effects. More specifically, the compounds of Formulae (I)-(VII) are useful in the treatment of a variety of cancers, including (but not limited to) the following:

carcinoma, including that of the prostate, pancreatic ductal adenocarcinoma, breast, colon, lung, ovary, pancreas, and thyroid;

tumors of the central and peripheral nervous system, including neuroblastoma, glioblastoma, and medulloblastoma; and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neurofibromatosis, pulmonary fibrosis, arthritis, psoriasis, glomerulonephritis, restenosis following angioplasty or vascular surgery, hypertrophic scar formation and inflammatory bowel disease.

The compounds of Formulae (I)-(VII) are especially useful in treatment of tumors having a high incidence of serine/threonine kinase activity, such as prostate, colon, lung, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of Formulae (I)-(VII) may also be useful in the treatment of other cancerous diseases (such as acute myelogenous leukemia) that may be associated with signal transduction pathways operating through kinases such as DYRK1a, CDK, and GSK3β. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formulae (I)-(VII) and a pharmaceutically acceptable carrier.

A "pharmaceutically acceptable carrier" refers to media generally accepted in the art for the delivery of biologically active agents to animals, in particular, mammals.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS® Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

The compounds of Formulae (I)-(VII) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; buccally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically-acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

When a compound according to this invention is administered into a human subject, the daily dosage will normally be determined by the prescribing physician with the dosage generally varying according to the age, weight, sex and response of the individual patient, as well as the severity of the patient's symptoms. Exemplary dosage amounts for a mammal may include from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of protein kinase enzyme levels.

If formulated as a fixed dose, a combination product can, for example, utilize a dosage of the compound of Formulae (I)-(VII) within the dosage range described above and the dosage of another anti-cancer agent/treatment within the approved dosage range for such known anti-cancer agent/treatment. If a combination product is inappropriate, the compounds of Formulae (I)-(VII) and the other anti-cancer agent/treatment can, for example, be administered simultaneously or sequentially. If administered sequentially, the present invention is not limited to any particular sequence of administration. For example, compounds of Formulae (I)-(VII) can be administered either prior to, or after, administration of the known anti-cancer agent or treatment.

Biological Assays

CK1ε and CK1δ Kinase Assays

The kinase assay was performed in V-bottom 384-well plates. The final assay volume was 30 µl prepared from 15 µl additions of enzyme, substrates (fluoresceinated peptide FL-AHA-KRRRAL-PSER-VASLPGL-OH and ATP) and test compounds in assay buffer (20 mM HEPES pH 7.4, 30 mM $MgCl_2$, 0.015% Brij35 and 4 mM DTT).

The reaction was incubated at room temperature for 22 hours and terminated by adding 45 µl of 35 mM EDTA to each sample. The reaction mixture was analyzed on the Caliper LABCHIP®3000 (Caliper, Hopkinton, Mass.) by electrophoretic separation of the unphosphorylated substrate and phosphorylated product. Inhibition data were calculated by comparison of the no enzyme control reactions for 100% inhibition and vehicle-only reactions for 0% inhibition. The final concentration of reagents in the assay were 200 pM CK1ε or CK1δ, 50 µM ATP, 1.5 µM FL-AHA-KRRRAL-PSER-VASLPGL-OH, and 1.6% DMSO. Dose response curves were generated to determine the concentration required to inhibit 50% of the kinase activity ($IC_{50}$). Compounds were dissolved at 10 mM in dimethylsulfoxide (DMSO) and evaluated at eleven concentrations. $IC_{50}$ values were derived by non-linear regression analysis.

The following compounds were found to have the $IC_{50}$ described in Table A when measured in the assays described above.

TABLE A

| Example No. | CK1ε ($IC_{50}$, µM) | CK1δ ($IC_{50}$, µM) |
| --- | --- | --- |
| 1 | 0.0037 | 0.0005 |
| 2 | 0.0024 | 0.0002 |
| 3 | 0.0051 | 0.0005 |
| 4 | 0.0013 | 0.0003 |
| 5 | 0.0047 | 0.0004 |
| 6 | 0.0023 | 0.0003 |
| 7 | — | — |
| 8 | — | — |
| 9 | — | — |
| 10 | 0.0126 | 0.0021 |
| 11 | 0.0152 | 0.0018 |
| 12 | 0.0020 | 0.0003 |
| 13 | 0.0045 | 0.0005 |
| 14 | 0.0031 | 0.0005 |
| 15 | 0.0007 | 0.0002 |
| 16 | 0.0049 | 0.0008 |
| 17 | 0.0010 | 0.0002 |
| 18 | 0.0056 | 0.0005 |
| 19 | 0.0027 | 0.0002 |
| 20 | 0.0070 | 0.0005 |
| 21 | 0.0030 | 0.0002 |
| 22 | 0.0031 | 0.0006 |
| 23 | 0.0004 | 0.0001 |
| 24 | 0.0029 | 0.0004 |
| 25 | 0.2423 | 0.0095 |
| 26 | 0.0073 | 0.0004 |
| 27 | 0.0036 | 0.0005 |
| 28 | 0.0025 | 0.0002 |
| 29 | 0.0060 | 0.0004 |
| 30 | 0.0065 | 0.0005 |
| 31 | 0.0011 | 0.0001 |
| 32 | 0.0015 | 0.0003 |
| 33 | 0.0019 | 0.0003 |
| 34 | 0.0065 | 0.0010 |
| 35 | 0.0008 | 0.0002 |
| 36 | 0.0012 | 0.0001 |
| 37 | 0.0140 | 0.0011 |
| 38 | 0.0049 | 0.0003 |
| 39 | 0.0046 | 0.0004 |
| 40 | 0.0103 | 0.0028 |
| 41 | 0.0205 | 0.0028 |
| 42 | 0.0095 | 0.0008 |
| 43 | 0.0240 | 0.0016 |
| 44 | 0.0139 | 0.0020 |
| 45 | 0.1542 | 0.0192 |
| 46 | 0.0025 | 0.0004 |
| 47 | 0.1455 | 0.0120 |
| 48 | 0.0056 | 0.0004 |
| 49 | 0.0073 | 0.0007 |
| 50 | 0.0093 | 0.0007 |
| 51 | 0.0123 | 0.0015 |
| 52 | 0.0077 | 0.0009 |
| 53 | 0.0041 | 0.0004 |
| 54 | 0.0026 | 0.0003 |
| 55 | 0.0024 | 0.0003 |
| 56 | 0.0040 | 0.0003 |
| 57 | 0.0017 | 0.0002 |
| 58 | 0.0027 | 0.0002 |
| 59 | — | — |
| 60 | — | — |
| 61 | 0.1374 | 0.0195 |
| 62 | 0.0013 | 0.0004 |
| 63 | 0.0012 | 0.0003 |
| 64 | 0.0039 | 0.0005 |
| 65 | 0.0047 | 0.0004 |
| 66 | 0.0053 | 0.0007 |
| 67 | 0.0036 | 0.0004 |
| 68 | 0.0036 | 0.0003 |
| 69 | 0.0279 | 0.0014 |
| 70 | 0.0273 | 0.0038 |
| 71 | 0.0290 | 0.0025 |

Methods of Preparation

The compounds of the present invention may be prepared by methods such as those illustrated in the following schemes. Solvents, temperatures, pressures, and other reaction conditions may readily be selected by one of ordinary skill in the art. Starting materials are commercially available or readily prepared by one of ordinary skill in the art. These schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). All documents cited herein are incorporated herein by reference in their entirety.

In general, the time taken to complete a reaction procedure will be judged by the person performing the procedure, preferably with the aid of information obtained by monitoring the reaction by methods such as HPLC or TLC. A reaction does not have to go to completion to be useful to this invention. The methods for the preparation of various heterocycles used to this invention can be found in standard organic reference books, for example, Katritzky, A. R. et al., eds., *Comprehensive Heterocyclic Chemistry, The Structure, Reactions, Synthesis and Uses, of Heterocyclic Compounds*, First Edition, Pergamon Press, New York (1984), and Katritzky, A. R. et al., eds., *Comprehensive Heterocyclic Chemistry II, A Review of the Literature 1982-1995: The Structure, Reactions, Synthesis and Uses, of Heterocyclic Compounds*, Pergamon Press, New York (1996).

Unless otherwise specified, the various substituents of the compounds are defined in the same manner as the Formula (I) compound of the invention.

The following abbreviations are used in the example section below and elsewhere herein:
Ac Acetyl
Bn Benzyl
Boc$_2$O Di-tert-butyl dicarbonate
dba dibenzylideneacetone
DCM Dichloromethane
DIPEA Diisopropylethylamine
DMAP 4-Dimethylaminopyridine
DMF Dimethyl formamide
DMSO Dimethylsulfoxide
dppf 1,1'-Bis(diphenylphosphino)ferrocene
EtOAc Ethyl acetate
EtOH Ethanol
HATU (O-(7-azabenzotriazol-1-yl)-N,N,N',N'-tetramethyluronium hexafluorophosphate)
HPLC High-performance liquid chromatography
K$_3$PO$_4$ Potassium phosphate tribasic
LAH Lithium aluminum hydride
MeOH Methanol
MW Microwave
NaBH$_4$ Sodium borohydride
NaHCO$_3$ Sodium bicarbonate
NaOH Sodium hydroxide
Na$_2$SO$_4$ Sodium sulfate
NBS N-Bromosuccinimide
NH$_4$OAc Ammonium acetate
NIS N-Iodosuccinimide
PPh$_3$ Triphenylphosphine
Pd/C Palladium on Carbon
Pd$_2$(dba)$_3$ Tris(dibenzylideneacetone)dipalladium(0)
PdCl$_2$(dppf) [1,1'-Bis(diphenylphosphino)ferrocene]dichloropalladium(II)
RT Room Temperature
TEA or Et$_3$N Triethylamine
TFA Trifluoroacetic acid
TFAA Trifluoroacetic anhydride
THF Tetrahydrofuran HPLC Methods: Analytical HPLC/LC-MS retention time reported for each example and intermediate uses one of the following general analytical HPLC/LC-MS methods:

Method A: SunFire C18 (4.6×150) mm, 3.5 μ column; flow rate 1 mL/min; gradient time 15 min; 10% Solvent B to 100% Solvent B; monitoring at 254 nm and 220 nm (Solvent A: 5% Acetonitrile, 95% water, 0.05% TFA; Solvent B: 95% Acetonitrile, 5% water, 0.05% TFA).

Method B: XBridge Phenyl (4.6×150) mm, 3.5 μ column; flow rate 1 mL/min; gradient time 15 min; 10% Solvent B to 100% Solvent B; monitoring at 254 nm and 220 nm (Solvent A: 5% Acetonitrile, 95% water, 0.05% TFA; Solvent B: 95% Acetonitrile, 5% water, 0.05% TFA).

Method C: SunFire C18 (4.6×150) mm, 3.5 μ column; flow rate 1 mL/min; gradient time 23 min; 100% Solvent A to 100% Solvent B and holding 100% Solvent B for 5 min. Monitoring at 254 nm and 220 nm (Solvent A: 5% Acetonitrile, 95% water, 0.05% TFA Solvent B: 95% Acetonitrile, 5% water, 0.05% TFA).

Method D: XBridge Phenyl (4.6×150) mm, 3.5 μ column; flow rate 1 mL/min; gradient time 23 min; 100% Solvent A to 100% Solvent B and holding 100% Solvent B for 5 min. Monitoring at 254 nm and 220 nm (Solvent A: 5% Acetonitrile, 95% water, 0.05% TFA; Solvent B: 95% Acetonitrile, 5% water, 0.05% TFA).

Method E: SunFire C18 (4.6×150) mm, 3.5 μ column; flow rate 1 mL/min; gradient time 30 min; 10% Solvent B to 100% Solvent B and holding 100% Solvent B for 5 min. Monitoring at 254 nm and 220 nm (Solvent A: 5% Acetonitrile, 95% water, 0.05% TFA Solvent B: 95% Acetonitrile, 5% water, 0.05% TFA).

Method F: XBridge Phenyl (4.6×150) mm, 3.5 μ column; flow rate 1 mL/min; gradient time 30 min; 10% Solvent B to 100% Solvent B and holding 100% Solvent B for 5 min. Monitoring at 254 nm and 220 nm (Solvent A: 5% Acetonitrile, 95% water, 0.05% TFA; Solvent B: 95% Acetonitrile, 5% water, 0.05% TFA).

Method G: Eclipse XDB C18 (150×4.6) mm, 3.5 μ column; flow rate 1 mL/min; gradient time 18 min; 10% Solvent B to 100% Solvent B and holding 100% Solvent B for 5 min. Monitoring at 254 nm and 220 nm (Solvent A: 10 mM NH$_4$OAc in water, Solvent B: Acetonitrile).

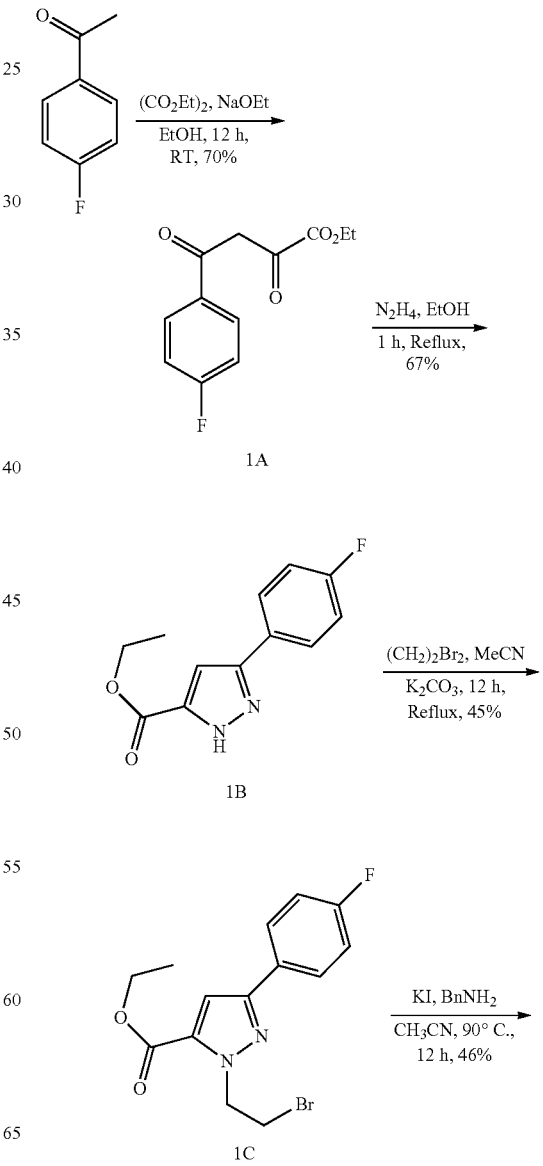

Scheme 1

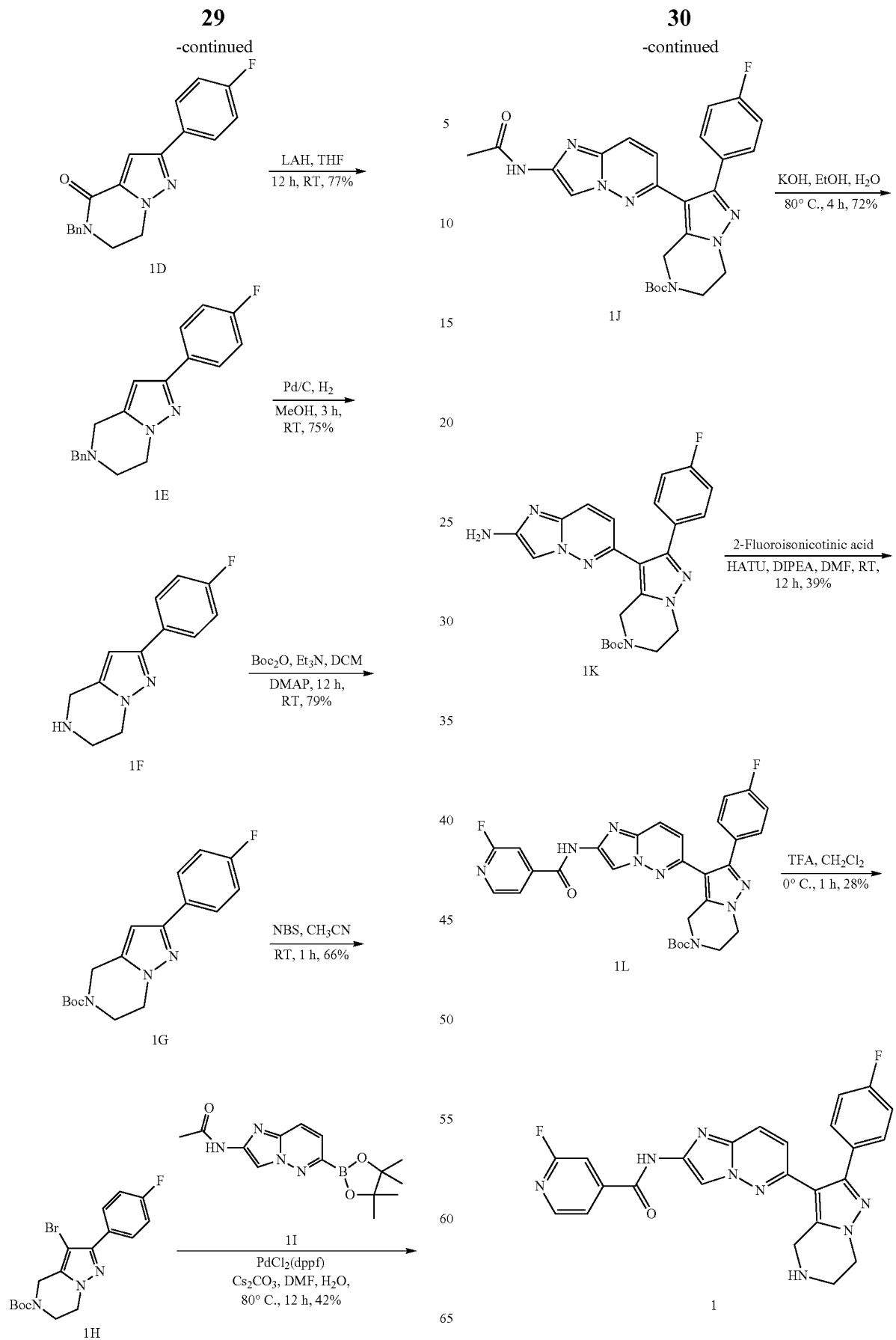

Intermediate 1A: Ethyl 4-(4-fluorophenyl)-2,4-dioxobutanoate

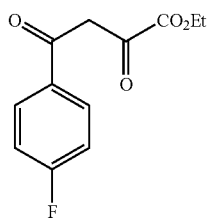 [SMILES: CCOC(=O)C(=O)CC(=O)c1ccc(F)cc1]

To a solution of sodium ethoxide (351 mL, 21% in ethanol, 1629 mmol) was added 1-(4-fluorophenyl) ethanone (150 g, 1086 mmol) in ethanol (100 mL) at 0° C. under a nitrogen atmosphere and stirred at RT for 10 min. Diethyl oxalate (156 mL, 1140 mmol) in ethanol (100 mL) was added and reaction was allowed to stir at RT for 12 h. The reaction mixture was cooled to 0° C. and acidified with 1.5 N HCl and the solid was filtered and the filtrate was diluted with water and extracted with DCM (3×750 mL). The combined organic layer was washed with brine, dried over $Na_2SO_4$, filtered and concentrated to afford Intermediate 1A (180 g, 70%), which was taken to next step without further purification. MS(ES): m/z=237 [M−H]$^+$; $^1$H NMR (300 MHz, $CDCl_3$) δ ppm 15.2 (bs, 1H), 8.00-8.09 (m, 2H), 7.15-7.25 (m, 2H), 7.05 (s, 1H), 4.42 (q, J=7.15 Hz, 2H), 1.43 (t, J=7.15 Hz, 3H).

Intermediate 1B: Ethyl 3-(4-fluorophenyl)-1H-pyrazole-5-carboxylate

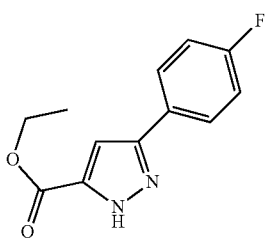 [SMILES: CCOC(=O)c1cc(-c2ccc(F)cc2)n[nH]1]

To a solution of Intermediate 1A (120 g, 504 mmol) in ethanol (1200 mL) was added hydrazine monohydrate (25.7 mL, 529 mmol) slowly and the resulting reaction mixture was refluxed for 1 h. The reaction mixture was cooled to RT, poured into ice cold water and the resultant solid was filtered and dried under vacuum to afford Intermediate 1B (80 g, 67%). MS(ES): m/z=235 [M+H]$^+$; $^1$H NMR (300 MHz, $CDCl_3$) δ ppm 7.75 (m, 2H), 7.12 (m, 2H), 7.07 (s, 1H), 4.42 (q, J=7.2 Hz, 2H), 1.42 (t, J=7.2 Hz, 3H).

Intermediate 1C: Ethyl 1-(2-bromoethyl)-3-(4-fluorophenyl)-1H-pyrazole-5-carboxylate

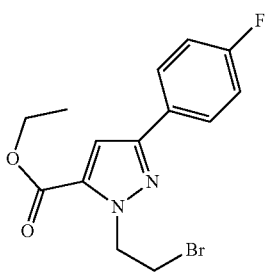 [SMILES: CCOC(=O)c1cc(-c2ccc(F)cc2)nn1CCBr]

To a solution of Intermediate 1B (135 g, 576 mmol) and potassium carbonate (159 g, 1153 mmol) in acetonitrile (1400 mL) was added 1,2-dibromoethane (59.6 mL, 692 mmol) and the resulting reaction mixture was refluxed for 4 h. Acetonitrile was removed under reduced pressure and the residue was diluted with water. The aqueous layer was extracted with DCM (2×500 mL). The combined organic layer was washed with brine, dried over $Na_2SO_4$, filtered and concentrated. The residue was purified by ISCO using 880 g REDISEP® column with 1% methanol in chloroform as the eluent. Combined fractions were concentrated to afford Intermediate 1C (90 g, 45%). MS(ES): m/z=343 [M+H]$^+$; $^1$H NMR (400 MHz, DMSO-$d_6$) δ ppm 7.91-7.97 (m, 2H), 7.41 (s, 1H), 7.24-7.30 (m, 2H), 4.96 (t, J=6.34 Hz, 2H), 4.36 (q, J=7.11 Hz, 2H), 3.90 (t, J=6.34 Hz, 2H), 1.35 (t, J=7.12 Hz, 3H).

Intermediate 1D: 5-Benzyl-2-(4-fluorophenyl)-6,7-dihydropyrazolo[1,5-a]pyrazin-4(5H)-one

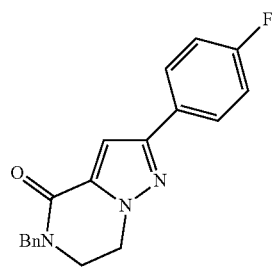 [SMILES: O=C1c2cc(-c3ccc(F)cc3)nn2CCN1Cc1ccccc1]

To a solution of Intermediate 1C (80 g, 234 mmol) and potassium iodide (78 g, 469 mmol) in acetonitrile (800 mL) was added benzyl amine (28.2 mL, 258 mmol) and the reaction mixture was stirred at 90° C. for 12 h. Acetonitrile was removed under reduced pressure, crude was diluted with water and the aqueous layer was extracted with DCM (3×500 mL). The combined organic layer washed with brine, dried over $Na_2SO_4$, filtered and concentrated. The residue was purified by silica gel chromatography (120 g REDISEP® column, eluting with 1-2% methanol in chloroform). Collected fractions were concentrated together to afford Intermediate 1D (35 g, 46%). MS(ES): m/z=322 [M+H]$^+$; $^1$H NMR (400 MHz, $CDCl_3$) δ ppm 7.71-7.83 (m, 2H), 7.29-7.42 (m, 5H), 7.14 (s, 1H), 7.06-7.12 (m, 2H), 4.78 (s, 2H), 4.32-4.40 (m, 2H), 3.63-3.75 (m, 2H).

Intermediate 1E: 5-Benzyl-2-(4-fluorophenyl)-4,5,6,7-tetrahydropyrazolo[1,5-a]pyrazine

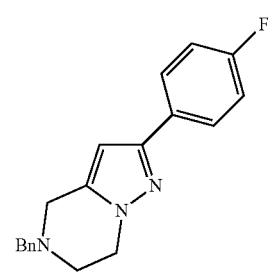

To a stirred solution of Intermediate 1D (23.00 g, 71.6 mmol) in THF (230 mL) under N₂ at −10° C. was added LAH (59.6 mL, 2.4 M solution in THF, 143 mmol), and then stirred at room temperature for additional 12 h. The reaction mixture was quenched with ice-cold water and filtered through CELITE® pad and the filtrate was extracted with chloroform (3×150 mL). The combined organic layer was washed with brine, dried over Na₂SO₄, filtered and concentrated. The residue was triturated with diethyl ether (2×150 mL) and the resulting solid was filtered, rinsed with diethyl ether and dried to afford Intermediate 1E (17 g, 77%). MS(ES): m/z=308 [M+H]⁺; ¹H NMR (300 MHz, CDCl₃) δ ppm 7.67-7.82 (m, 2H), 7.31-7.47 (m, 5H), 7.01-7.14 (m, 2H), 6.19 (s, 1H), 4.22 (t, J=4.2 Hz, 2H), 3.73 (s, 2H), 3.70 (s, 2H), 2.97 (t, J=5.6 Hz, 2H).

Intermediate 1F: 2-(4-Fluorophenyl)-4,5,6,7-tetrahydropyrazolo[1,5-a]pyrazine

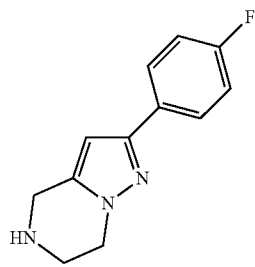 [SMILES: Fc1ccc(-c2cc3n(n2)CCNC3)cc1]

To a degassed solution of Intermediate 1E (17 g, 55.3 mmol) in methanol (170 mL) was added 10% palladium on carbon (2.94 g, 2.77 mmol) and stirred under one atmospheric hydrogen pressure for 3 h. The reaction mixture was filtered through CELITE® pad, washed with methanol (500 mL) and concentrated. The residue was triturated with diethyl ether (2×100 mL) and the resulting solid was filtered, rinsed with diethyl ether (200 mL) and dried under vacuum to afford Intermediate 1F (9 g, 75%). MS(ES): m/z=218 [M+H]⁺; ¹H NMR (300 MHz, DMSO-d₆) δ ppm 7.73-7.87 (m, 2H), 7.13-7.28 (m, 2H), 6.43 (s, 1H), 4.02 (t, J=5.57 Hz, 2H), 3.94 (s, 2H), 3.16 (t, J=5.57 Hz, 2H).

Intermediate 1G: tert-Butyl 2-(4-fluorophenyl)-6,7-dihydropyrazolo[1,5-a]pyrazine-5(4H)-carboxylate

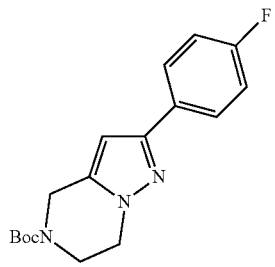 [SMILES: CC(C)(C)OC(=O)N1CCn2nc(-c3ccc(F)cc3)cc2C1]

To a stirred solution of Intermediate 1F (9.50 g, 43.7 mmol) and triethylamine (18.29 mL, 131 mmol) in DCM (80 mL) was added Boc₂O (19.09 g, 87 mmol) and DMAP (0.534 g, 4.37 mmol). Stirring was continued at RT for 12 h. DCM was removed under reduced pressure and the residue was purified by ISCO using 120 g REDISEP® column with 1-2% methanol in chloroform as eluent. Collected fractions were concentrated together to afford Intermediate 1G (11 g, 79%). MS(ES): m/z=318 [M+H]⁺; ¹H NMR (400 MHz, CDCl₃) δ ppm 7.70-7.75 (m, 2H), 7.02-7.12 (m, 2H), 6.31 (s, 1H), 4.68 (s, 2H), 4.21 (t, J=5.4 Hz, 2H), 3.92 (t, J=5.7 Hz, 2H), 1.50 (s, 9H).

Intermediate 1H: tert-Butyl 3-bromo-2-(4-fluorophenyl)-6,7-dihydropyrazolo[1,5-a]pyrazine-5 (4H)-carboxylate

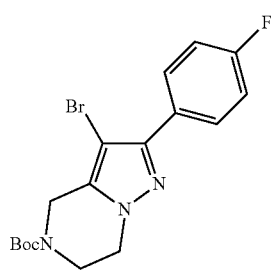 [SMILES: CC(C)(C)OC(=O)N1CCn2nc(-c3ccc(F)cc3)c(Br)c2C1]

To a solution of Intermediate 1F (6.0 g, 18.91 mmol) in DCM (60 mL) at 0° C. was added N-bromosuccinimide (3.36 g, 18.91 mmol) and reaction was stirred at RT for 1 h. The solvent was removed under reduced pressure and the residue was purified by silica gel chromatography (120 g REDISEP® column, eluting with 1-2% methanol in chloroform). Collected fractions were concentrated together to afford Intermediate 1H (5 g, 66%). MS(ES): m/z=396 [M+H]⁺; ¹H NMR (300 MHz, chloroform-d) δ ppm 7.80-7.93 (m, 2H), 7.07-7.21 (m, 2H), 4.60 (s, 2H), 4.17-4.27 (m, 2H), 3.90-3.99 (m, 2H), 1.54 (s, 9H).

Intermediate 1J: tert-Butyl 3-(2-acetamidoimidazo[1,2-b]pyridazin-6-yl)-2-(4-fluorophenyl)-6,7-dihydropyrazolo[1,5-a]pyrazine-5(4H)-carboxylate

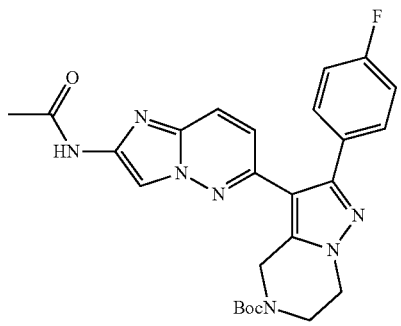 [SMILES: CC(=O)Nc1cn2nc(-c3c(-c4ccc(F)cc4)nn4c3CN(C(=O)OC(C)(C)C)CC4)ccc2n1]

To a solution of Intermediate 1H (4.0 g, 10.09 mmol), boronate ester 1I (7.62 g, 25.2 mmol), cesium carbonate (9.87 g, 30.3 mmol) in DMF (3 mL) and water (12 mL) under N₂ was added PdCl₂(dppf) (0.443 g, 0.606 mmol). The reaction was degasified with N₂ for 5 min. and heated at 80° C. for 12 h. DMF was removed under high vacuum, diluted with ethyl acetate and filtered through CELITE® pad. The organic layer was washed with water, brine, dried over Na₂SO₄, filtered and concentrated. The residue was purified by silica gel chromatography (40 g REDISEP® column, eluting with 3% methanol in chloroform). Collected fractions were concentrated together to afford Intermediate 1J (2.1 g, 42%). MS(ES): m/z=492 [M+H]; $^1$H NMR (300 MHz, DMSO-d$_6$) δ ppm 10.89 (s, 1H), 8.21 (s, 1H), 7.85 (dd, J=9.40, 0.57 Hz, 1H), 7.44-7.57 (m, 2H), 7.17-7.32 (m, 2H), 6.77 (d, J=9.40 Hz, 1H), 4.84 (s, 2H), 4.24 (t, J=5.26 Hz, 2H), 3.86-4.00 (m, 2H), 2.11 (s, 3H), 1.45 (s, 9H).

Intermediate 1K: tert-Butyl 3-(2-aminoimidazo[1,2-b]pyridazin-6-yl)-2-(4-fluorophenyl)-6,7-dihydropyrazolo[1,5-a]pyrazine-5(4H)-carboxylate

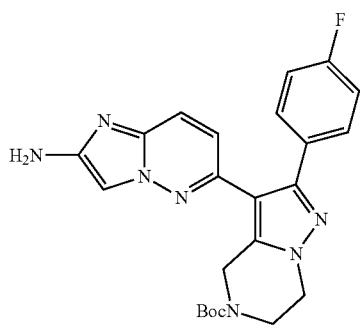 [SMILES: CC(C)(C)OC(=O)N1CCn2nc(-c3ccc(F)cc3)c(-c3ccc4nc(N)cn4n3)c2C1]

To a stirred solution of Intermediate 1J (0.45 g, 0.916 mmol) in ethanol (10 mL) and water (5 mL) was added potassium hydroxide pellets (0.257 g, 4.58 mmol) and the resulting solution was heated at 80° C. for 4 h. Volatiles were removed, diluted with water and the aqueous layer was extracted with DCM (2×50 mL). The combined the organic layer was washed with brine, dried over Na$_2$SO$_4$, filtered and concentrated to afford Intermediate 1K (0.3 g, 72%), which was used for the next step without further purification. $^1$H NMR (400 MHz, chloroform-d) δ ppm 7.39-7.49 (m, 3H), 7.31 (s, 1H), 7.02-7.12 (m, 2H), 6.63 (d, J=9.22 Hz, 1H), 4.84-5.01 (m, 2H), 4.27 (t, J=5.21 Hz, 2H), 3.93-4.01 (m, 2H), 1.58 (s, 9H).

Intermediate 1L: tert-Butyl 3-(2-(2-fluoroisonicotinamido)imidazo[1,2-b]pyridazin-6-yl)-2-(4-fluorophenyl)-6,7-dihydropyrazolo[1,5-a]pyrazine-5(4H)-carboxylate

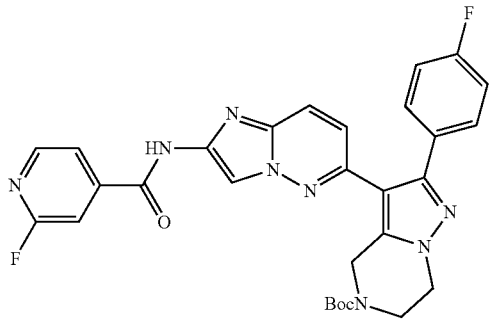 [SMILES: CC(C)(C)OC(=O)N1CCn2nc(-c3ccc(F)cc3)c(-c3ccc4nc(NC(=O)c5ccnc(F)c5)cn4n3)c2C1]

To a stirred solution of Intermediate 1K (0.80 g, 1.780 mmol) and 2-fluoroisonicotinic acid (0.50 g, 3.56 mmol) in DMF (18 mL) under N$_2$ was added HATU (1.35 g, 3.56 mmol) and DIPEA (0.93 mL, 5.34 mmol) and the reaction mixture was stirred at RT for 12 h. DMF was removed by high vacuum and the crude product was diluted with water and extracted with ethyl acetate (2×50 mL). The combined the organic layer was washed with brine, dried over Na$_2$SO$_4$, filtered and concentrated. The residue was purified by silica gel chromatography (24 g REDISEP® column, eluting with 2-3% methanol in chloroform). Collected fractions were concentrated together to afford Intermediate 1L (0.4 g, 39%). MS(ES): m/z=573 [M+H]$^+$; $^1$H NMR (300 MHz, DMSO-d$_6$) δ ppm 11.86 (s, 1H), 8.42-8.54 (m, 2H), 7.93-8.02 (m, 2H), 7.77-7.84 (m, 1H), 7.47-7.59 (m, 2H), 7.19-7.32 (m, 2H), 6.84 (d, J=9.44 Hz, 1H), 4.87 (s, 2H), 4.18-4.34 (m, 2H), 3.84-4.01 (m, 2H), 1.43-1.52 (m, 9H).

Compound 1: 2-Fluoro-N-(6-(2-(4-fluorophenyl)-4,5,6,7-tetrahydropyrazolo[1,5-a]pyrazin-3-yl)imidazo[1,2-b]pyridazin-2-yl)isonicotinamide

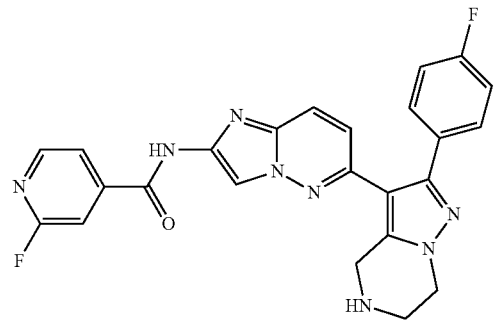 [SMILES: O=C(Nc1cn2nc(-c3c(-c4ccc(F)cc4)nn4c3CNCC4)ccc2n1)c1ccnc(F)c1]

To a solution of Intermediate 1L (50 mg, 0.087 mmol) in DCM (2 mL) at 0° C. was added trifluoroacetic acid (0.020 mL, 0.262 mmol) and the reaction mixture was stirred at RT for 1 h, volatiles were removed under reduced pressure, the residue was diluted with water and the aqueous layer was extracted with DCM (3×15 mL). The combined organic layer was washed with sodium bicarbonate solution (2×20 mL), dried over Na$_2$SO$_4$, filtered and concentrated. The crude product was purified by preparative HPLC to afford Compound 1 (0.012 g, 28%) as an off-white solid. MS(ES): m/z=473 [M+H]$^+$; HPLC Ret. Time 5.65 min and 6.31 min (HPLC Methods A and B, respectively); $^1$H NMR (400 MHz, DMSO-d$_6$) δ ppm 11.84 (s, 1H), 8.43-8.48 (m, 2H), 7.90-7.98 (m, 2H), 7.80 (s, 1H), 7.51 (dd, J=8.78, 5.52 Hz, 2H), 7.23 (t, J=8.91 Hz, 2H), 6.85 (d, J=9.54 Hz, 1H), 4.09-4.15 (m, 4H), 3.21 (t, J=5.27 Hz, 2H).

The Compounds shown in Table 1 have been prepared similar to Compound 1 by coupling of Intermediate 1K with various carboxylic acids followed by deprotection of the BOC group.

TABLE 1

| Ex. No. | Structure | Name | [M + H]+ | Ret Time (min) | HPLC Methods |
|---|---|---|---|---|---|
| 2 | 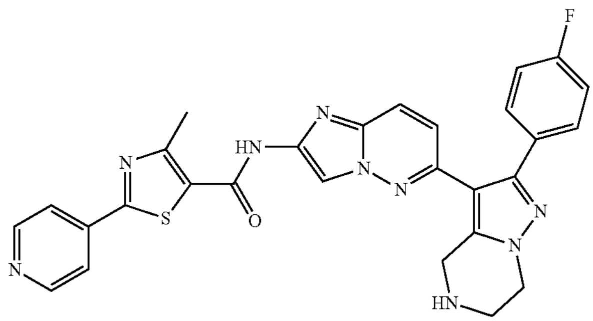 [SMILES: Cc1nc(-c2ccncc2)sc1C(=O)Nc1cn2nc(-c3c(-c4ccc(F)cc4)nn4c3CNCC4)ccc2n1] | N-(6-(2-(4-Fluorophenyl)-4,5,6,7-tetrahydropyrazolo[1,5-a]pyrazin-3-yl)imidazo[1,2-b]pyridazin-2-yl)-4-methyl-2-(pyridin-4-yl)thiazole-5-carboxamide | 552 | 5.49<br>9.99 | B<br>C |
| 3 | 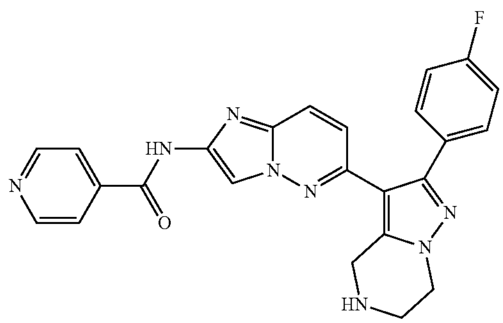 [SMILES: O=C(Nc1cn2nc(-c3c(-c4ccc(F)cc4)nn4c3CNCC4)ccc2n1)c1ccncc1] | N-(6-(2-(4-Fluorophenyl)-4,5,6,7-tetrahydropyrazolo[1,5-a]pyrazin-3-yl)imidazo[1,2-b]pyridazin-2-yl)isonicotinamide | 453[M − H] | 4.47<br>5.15 | A<br>B |
| 4 | 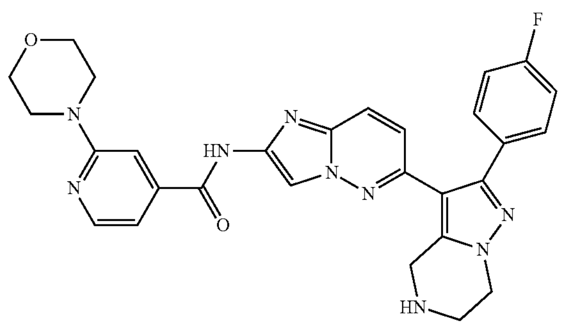 [SMILES: O=C(Nc1cn2nc(-c3c(-c4ccc(F)cc4)nn4c3CNCC4)ccc2n1)c1ccnc(N2CCOCC2)c1] | N-(6-(2-(4-Fluorophenyl)-4,5,6,7-tetrahydropyrazolo[1,5-a]pyrazin-3-yl)imidazo[1,2-b]pyridazin-2-yl)-2-morpholinoisonicotinamide | 583[M − H] | 4.73<br>5.53 | A<br>B |
| 5 | 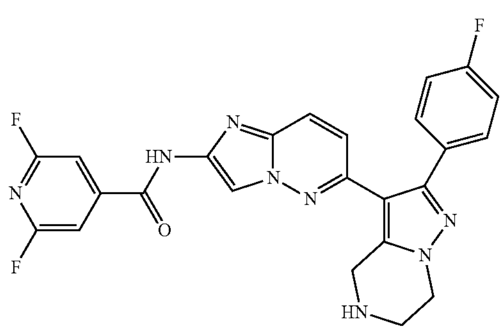 | 2,6-Difluoro-N-(6-(2-(4-fluorophenyl)-4,5,6,7-tetrahydropyrazolo[1,5-a]pyrazin-3-yl)imidazo[1,2-b]pyridazin-2-yl)isonicotinamide | 491 | 6.58<br>7.63 | A<br>B |

TABLE 1-continued

| Ex. No. | Structure | Name | [M + H]+ | Ret Time (min) | HPLC Methods |
|---|---|---|---|---|---|
| 6 | 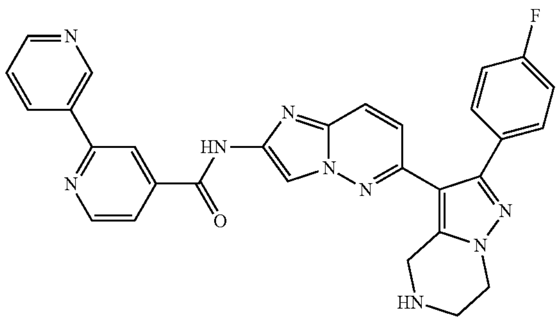 [SMILES: O=C(Nc1cn2nc(-c3c(-c4ccc(F)cc4)nn4c3CNCC4)ccc2n1)c1ccnc(-c2cccnc2)c1] | N-(6-(2-(4-Fluorophenyl)-4,5,6,7-tetrahydropyrazolo[1,5-a]pyrazin-3-yl)imidazo[1,2-b]pyridazin-2-yl)-[2,3'-bipyridine]-4-carboxamide | 532 | 10.17<br>11.63 | C<br>D |
| 7 | 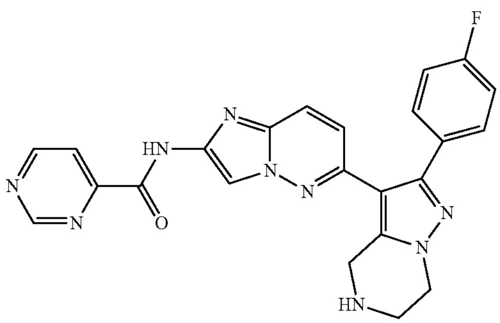 | N-(6-(2-(4-Fluorophenyl)-4,5,6,7-tetrahydropyrazolo[1,5-a]pyrazin-3-yl)imidazo[1,2-b]pyridazin-2-yl)pyrimidine-4-carboxamide | 456 | 5.22<br>6.03 | A<br>B |
| 8 | 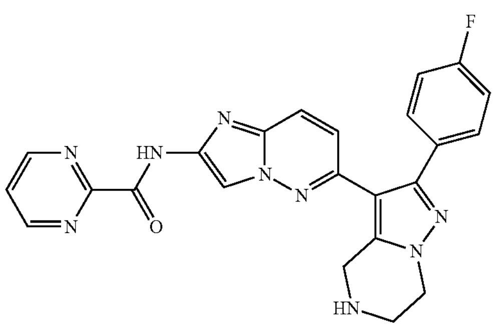 [SMILES: O=C(Nc1cn2nc(-c3c(-c4ccc(F)cc4)nn4c3CNCC4)ccc2n1)c1ncccn1] | N-(6-(2-(4-Fluorophenyl)-4,5,6,7-tetrahydropyrazolo[1,5-a]pyrazin-3-yl)imidazo[1,2-b]pyridazin-2-yl)pyrimidine-2-carboxamide | 456 | 5.79<br>10.09 | B<br>C |
| 9 | 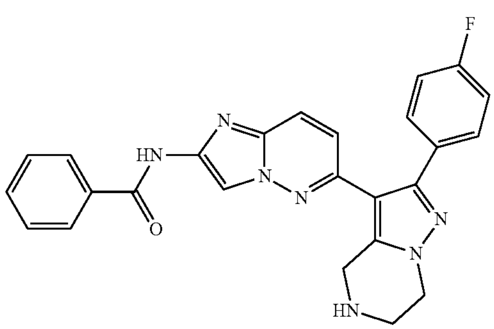 [SMILES: O=C(Nc1cn2nc(-c3c(-c4ccc(F)cc4)nn4c3CNCC4)ccc2n1)c1ccccc1] | N-(6-(2-(4-Fluorophenyl)-4,5,6,7-tetrahydropyrazolo[1,5-a]pyrazin-3-yl)imidazo[1,2-b]pyridazin-2-yl)benzamide | 454 | 6.07<br>7.00 | A<br>B |

TABLE 1-continued

| Ex. No. | Structure | Name | [M + H]+ | Ret Time (min) | HPLC Methods |
|---|---|---|---|---|---|
| 10 | 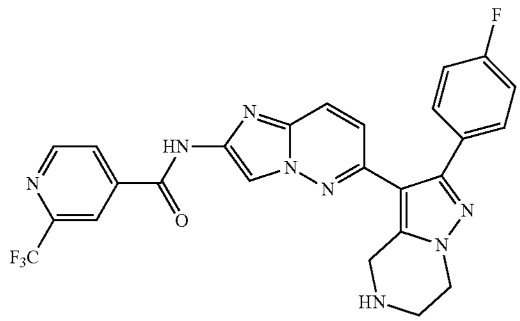 [SMILES: O=C(Nc1cn2nc(-c3c(-c4ccc(F)cc4)nn4c3CNCC4)ccc2n1)c1ccnc(C(F)(F)F)c1] | N-(6-(2-(4-Fluorophenyl)-4,5,6,7-tetrahydropyrazolo[1,5-a]pyrazin-3-yl)imidazo[1,2-b]pyridazin-2-yl)-2-(trifluoromethyl)isonicotinamide | 521[M − H] | 6.42 9.38 | A G |
| 11 | 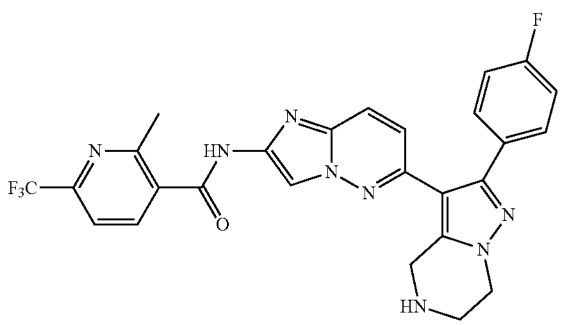 [SMILES: Cc1nc(C(F)(F)F)ccc1C(=O)Nc1cn2nc(-c3c(-c4ccc(F)cc4)nn4c3CNCC4)ccc2n1] | N-(6-(2-(4-Fluorophenyl)-4,5,6,7-tetrahydropyrazolo[1,5-a]pyrazin-3-yl)imidazo[1,2-b]pyridazin-2-yl)-2-methyl-6-(trifluoromethyl)nicotinamide | 537 | 6.45 7.48 | A B |

Compound 12: N-(6-(5-Acetyl-2-(4-fluorophenyl)-4,5,6,7-tetrahydropyrazolo[1,5-a]pyrazin-3-yl)imidazo[1,2-b]pyridazin-2-yl)-2-fluoroisonicotinamide

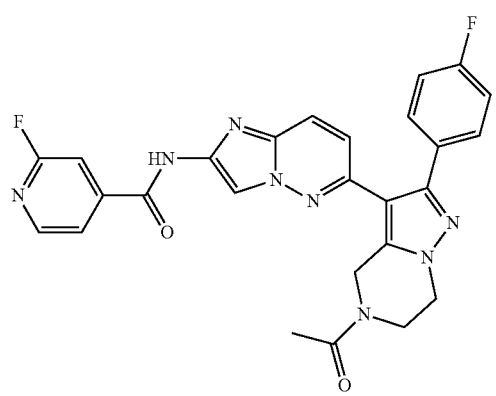 [SMILES: CC(=O)N1CCn2nc(-c3ccc(F)cc3)c(-c3ccc4nc(NC(=O)c5ccnc(F)c5)cn4n3)c2C1]

To a stirred solution of Compound 1 (25 mg, 0.053 mmol) and acetic acid (3.18 mg, 0.053 mmol) in DMF (0.5 mL) under $N_2$ was added HATU (40.2 mg, 0.106 mmol) and DIPEA (0.028 mL, 0.159 mmol) and the reaction mixture was stirred at RT for 24 h. DMF was removed under high vacuum, the crude was diluted with water, and the aqueous layer was back extracted with chloroform (3×25 mL). The combined organic layer was washed with brine, dried over $Na_2SO_4$, filtered and concentrated. Crude was purified by preparative HPLC to afford Compound 12 (12 mg, 44%) as pale yellow solid. MS(ES): m/z=513 [M−H]+; HPLC Ret. Time 8.38 min and 7.85 min (HPLC Methods A and B, respectively). $^1$H NMR (400 MHz, DMSO-$d_6$) δ ppm 11.85 (br. s., 1H), 8.41-8.55 (m, 2H), 7.92-7.99 (m, 2H), 7.81 (s, 1H), 7.47-7.57 (m, 2H), 7.20-7.30 (m, 2H), 6.82-6.90 (m, 1H), 4.91-5.04 (m, 2H), 4.23-4.39 (m, 2H), 4.05 (br. s., 2H), 2.14-2.19 (m, 2H).

The Compounds shown in Table 2 have been prepared similar to 12 by coupling of Compound 1 and various carboxylic acids.

TABLE 2

| Ex. No. | Structure | Name | [M + H]+ | Ret Time (min) | HPLC Methods |
|---|---|---|---|---|---|
| 13 | 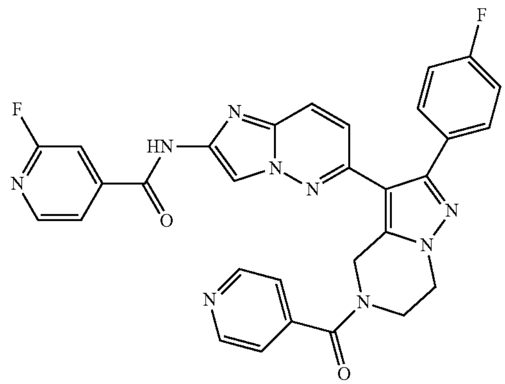 [SMILES: O=C(Nc1cn2nc(-c3c(-c4ccc(F)cc4)nn4c3CN(C(=O)c3ccncc3)CC4)ccc2n1)c1ccnc(F)c1] | 2-Fluro-N-(6-(2-(4-fluorophenyl)-5-isonicotinoyl-4,5,6,7-tetrahydropyrazolo[1,5-a]pyrazin-3-yl)imidazo[1,2-b]pyridazin-2-yl)isonicotinamide | 577.7 | 8.44 | G |
| 14 | 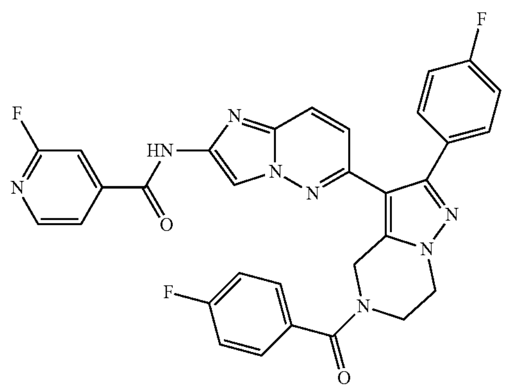 [SMILES: O=C(Nc1cn2nc(-c3c(-c4ccc(F)cc4)nn4c3CN(C(=O)c3ccc(F)cc3)CC4)ccc2n1)c1ccnc(F)c1] | 2-Fluoro-N-(6-(5-(4-fluorobenzoyl)-2-(4-fluorophenyl)-4,5,6,7-tetrahydropyrazolo[1,5-a]pyrazin-3-yl)imidazo[1,2-b]pyridazin-2-yl)isonicotinamide | 593[M − H] | 15.73 14.18 | E F |
| 15 | 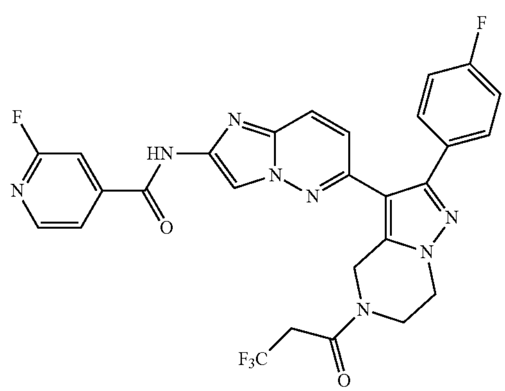 [SMILES: O=C(Nc1cn2nc(-c3c(-c4ccc(F)cc4)nn4c3CN(C(=O)CC(F)(F)F)CC4)ccc2n1)c1ccnc(F)c1] | 2-Fluoro-N-(6-(2-(4-fluorophenyl)-5-(3,3,3-trifluoropropanoyl)-4,5,6,7-tetrahydropyrazolo[1,5-a]pyrazin-3-yl)imidazo[1,2-b]pyridazin-2-yl)isonicotinamide | 581[M − H] | 15.17 13.71 | E F |
| 16 | 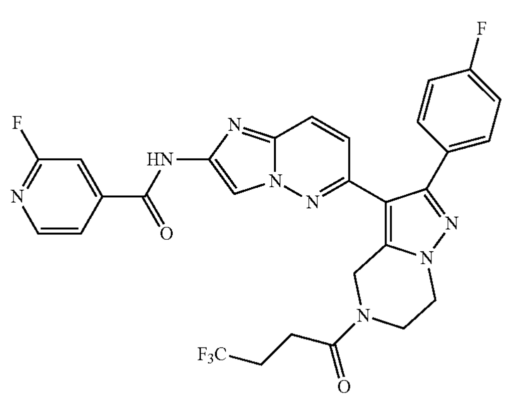 [SMILES: O=C(Nc1cn2nc(-c3c(-c4ccc(F)cc4)nn4c3CN(C(=O)CCC(F)(F)F)CC4)ccc2n1)c1ccnc(F)c1] | 2-Fluoro-N-(6-(2-(4-fluorophenyl)-5-(4,4,4-trifluorobutanoyl)-4,5,6,7-tetrahydropyrazolo[1,5-a]pyrazin-3-yl)imidazo[1,2-b]pyridazin-2-yl)isonicotinamide | 595[M − H] | 16.00 14.35 | E F |

TABLE 2-continued

| Ex. No. | Structure | Name | [M + H]+ | Ret Time (min) | HPLC Methods |
|---|---|---|---|---|---|
| 17 | 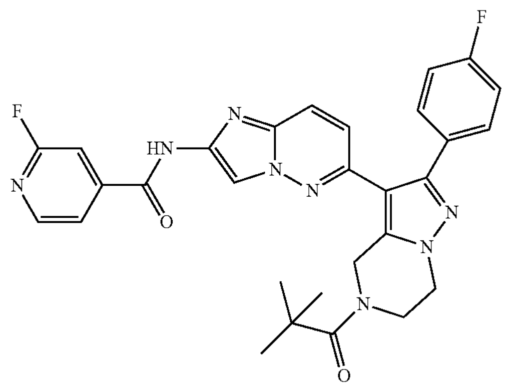 [SMILES: CC(C)(C)C(=O)N1CCn2nc(-c3ccc(F)cc3)c(-c3ccc4nc(NC(=O)c5ccnc(F)c5)cn4n3)c2C1] | 2-Fluoro-N-(6-(2-(4-fluorophenyl)-5-pivaloyl-4,5,6,7-tetrahydropyrazolo[1,5-a]pyrazin-3-yl)imidazo[1,2-b]pyridazin-2-yl)isonicotinamide | 557 | 16.78 14.98 | E F |
| 18 | 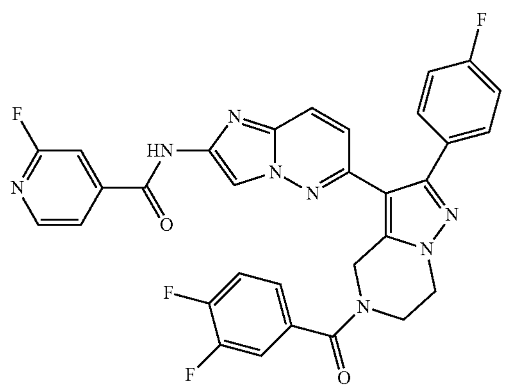 [SMILES: O=C(Nc1cn2nc(-c3c(-c4ccc(F)cc4)nn4c3CN(C(=O)c3ccc(F)c(F)c3)CC4)ccc2n1)c1ccnc(F)c1] | N-(6-(5-(3,4-Difluorobenzoyl)-2-(4-fluorophenyl)-4,5,6,7-tetrahydropyrazolo[1,5-a]pyrazin-3-yl)imidazo[1,2-b]pyridazin-2-yl)-2-fluoroisonicotinamide | 611[M − H] | 10.47 9.66 | A B |
| 19 | 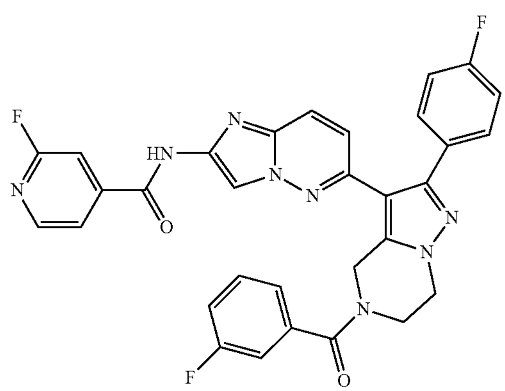 [SMILES: O=C(Nc1cn2nc(-c3c(-c4ccc(F)cc4)nn4c3CN(C(=O)c3cccc(F)c3)CC4)ccc2n1)c1ccnc(F)c1] | 2-Fluoro-N-(6-(5-(3-fluorobenzoyl)-2-(4-fluorophenyl)-4,5,6,7-tetrahydropyrazolo[1,5-a]pyrazin-3-yl)imidazo[1,2-b]pyridazin-2-yl)isonicotinamide | 593[M − H] | 10.25 9.48 | A B |
| 20 | 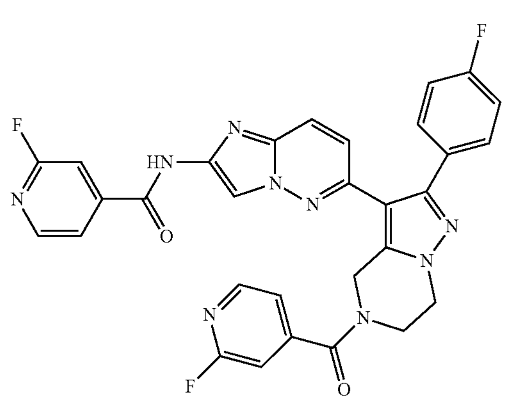 [SMILES: O=C(Nc1cn2nc(-c3c(-c4ccc(F)cc4)nn4c3CN(C(=O)c3ccnc(F)c3)CC4)ccc2n1)c1ccnc(F)c1] | 2-Fluoro-N-(6-(5-(2-fluoroisonicotinoyl)-2-(4-fluorophenyl)-4,5,6,7-tetrahydropyrazolo[1,5-a]pyrazin-3-yl)imidazo[1,2-b]pyridazin-2-yl)isonicotinamide | 594[M − H] | 9.39 8.80 | A B |

TABLE 2-continued

| Ex. No. | Structure | Name | [M + H]+ | Ret Time (min) | HPLC Methods |
|---|---|---|---|---|---|
| 21 | 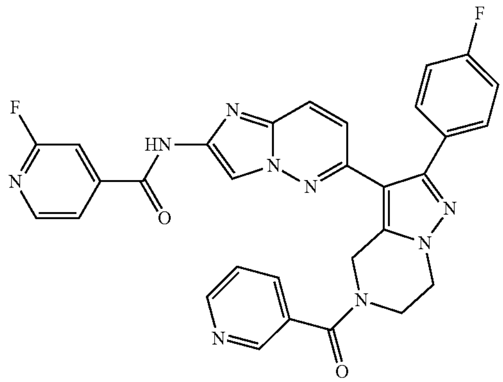 [SMILES: O=C(Nc1cn2nc(-c3c(-c4ccc(F)cc4)nn4c3CN(C(=O)c3cccnc3)CC4)ccc2n1)c1ccnc(F)c1] | 2-Fluoro-N-(6-(2-(4-fluorophenyl)-5-nicotinoyl-4,5,6,7-tetrahydropyrazolo[1,5-a]pyrazin-3-yl)imidazo[1,2-b]pyridazin-2-yl)isonicotinamide | 576[M − H] | 7.47<br>7.34 | A<br>B |
| 22 | 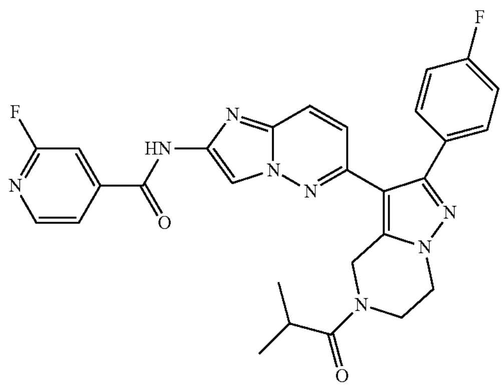 [SMILES: CC(C)C(=O)N1CCn2nc(-c3ccc(F)cc3)c(-c3ccc4nc(NC(=O)c5ccnc(F)c5)cn4n3)c2C1] | 2-Fluoro-N-(6-(2-(4-fluorophenyl)-5-isobutyryl-4,5,6,7-tetrahydropyrazolo[1,5-a]pyrazin-3-yl)imidazo[1,2-b]pyridazin-2-yl)isonicotinamide | 541[M − H] | 9.61<br>8.79 | A<br>B |
| 23 | 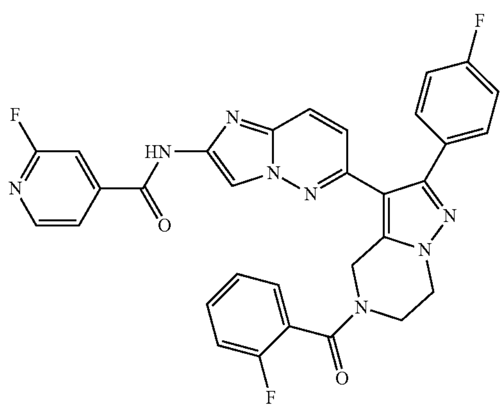 [SMILES: O=C(Nc1cn2nc(-c3c(-c4ccc(F)cc4)nn4c3CN(C(=O)c3ccccc3F)CC4)ccc2n1)c1ccnc(F)c1] | 2-Fluoro-N-(6-(5-(2-fluorobenzoyl)-2-(4-fluorophenyl)-4,5,6,7-tetrahydropyrazolo[1,5-a]pyrazin-3-yl)imidazo[1,2-b]pyridazin-2-yl)isonicotinamide | 595 | 16.29<br>15.05 | E<br>F |
| 24 | 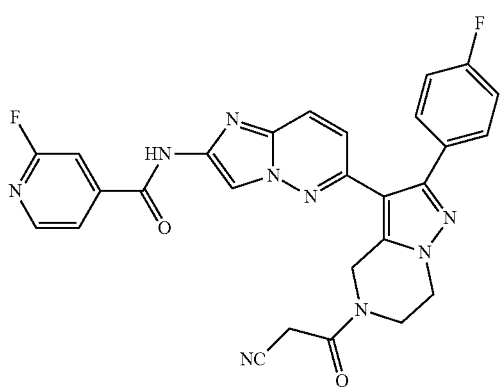 [SMILES: N#CCC(=O)N1CCn2nc(-c3ccc(F)cc3)c(-c3ccc4nc(NC(=O)c5ccnc(F)c5)cn4n3)c2C1] | N-(6-(5-(2-Cyanoacetyl)-2-(4-fluorophenyl)-4,5,6,7-tetrahydropyrazolo[1,5-a]pyrazin-3-yl)imidazo[1,2-b]pyridazin-2-yl)-2-fluoroisonicotinamide | 540 | 8.02<br>8.07 | A<br>B |

TABLE 2-continued

| Ex. No. | Structure | Name | [M + H]+ | Ret Time (min) | HPLC Methods |
|---|---|---|---|---|---|
| 25 | 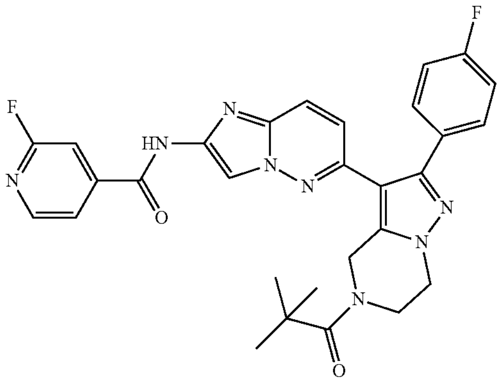 [SMILES: CC(C)(C)C(=O)N1CCn2nc(-c3ccc(F)cc3)c(-c3ccc4nc(NC(=O)c5ccnc(F)c5)cn4n3)c2C1] | 2-Fluoro-N-(6-(2-(4-fluorophenyl)-5-pivaloyl-4,5,6,7-tetrahydropyrazolo[1,5-a]pyrazin-3-yl)imidazo[1,2-b]pyridazin-2-yl)isonicotinamide | 571[M − H] | 11.62<br>10.65 | A<br>B |

Compound 26: 2-Fluoro-N-(6-(2-(4-fluorophenyl)-5-methyl-4,5,6,7-tetrahydropyrazolo [1,5-a]pyrazin-3-yl)imidazo[1,2-b]pyridazin-2-yl)isonicotinamide

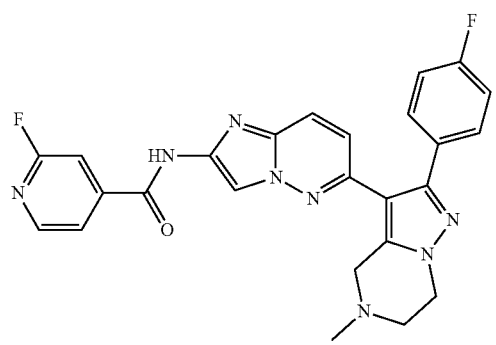 [SMILES: CN1CCn2nc(-c3ccc(F)cc3)c(-c3ccc4nc(NC(=O)c5ccnc(F)c5)cn4n3)c2C1]

To a stirred solution of Compound 1 (20 mg, 0.042 mmol) and paraformaldehyde (6.36 mg, 0.212 mmol) in methanol (0.5 mL) and THF (0.5 mL) was added sodium cyanoborohydride (3.99 mg, 0.063 mmol) and stirred at RT for 4 h. Reaction mixture was concentrated under reduced pressure, diluted with water and the aqueous layer was back extracted with DCM (3×15 mL). The combined organic layer was washed with brine, dried over $Na_2SO_4$, filtered and concentrated. The crude was purified by preparative HPLC to afford Compound 26 (0.005 g, 24%) as white solid. MS(ES): m/z=485 [M+H]+; HPLC Ret. Time 6.46 min and 5.76 min (HPLC Methods B and E, respectively). $^1$H NMR (400 MHz, DMSO-$d_6$) δ ppm 11.83 (s, 1H), 8.45-8.49 (m, 2H), 7.95-7.98 (m, 1H), 7.93 (d, J=9.41 Hz, 1H), 7.80 (s, 1H), 7.49-7.54 (m, 2H), 7.21-7.27 (m, 2H), 6.86 (d, J=9.41 Hz, 1H), 4.24 (t, J=5.40 Hz, 2H), 3.83 (s, 2H), 2.95 (t, J=5.43 Hz, 2H), 2.46 (s, 4H).

The Compounds shown in Table 3 have been prepared similar to Compound 26 by reductive amination of Compound 1 with various carbonyl compounds.

TABLE 3

| Ex. No. | Structure | Name | [M + H]+ | Ret Time (min) | HPLC Methods |
|---|---|---|---|---|---|
| 27 | 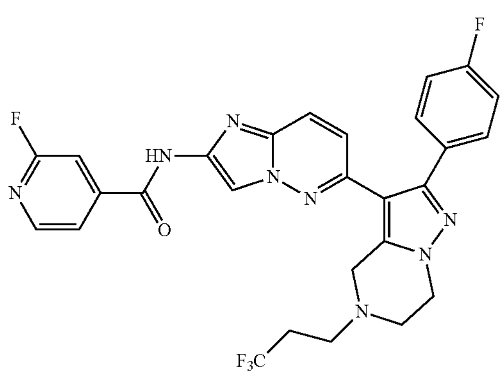 [SMILES: O=C(Nc1cn2nc(-c3c(-c4ccc(F)cc4)nn4c3CN(CCC(F)(F)F)CC4)ccc2n1)c1ccnc(F)c1] | 2-Fluoro-N-(6-(2-(4-fluorophenyl)-5-(3,3,3-trifluoropropyl)-4,5,6,7-tetrahydropyrazolo[1,5-a]pyrazin-3-yl)imidazo[1,2-b]pyridazin-2-yl)isonicotinamide | 569 | 9.76<br>9.17 | A<br>B |

TABLE 3-continued

| Ex. No. | Structure | Name | [M + H]+ | Ret Time (min) | HPLC Methods |
|---|---|---|---|---|---|
| 28 | 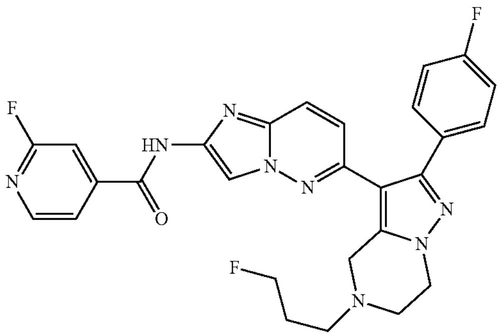 [SMILES: O=C(Nc1cn2nc(-c3c(-c4ccc(F)cc4)nn4c3CN(CCCF)CC4)ccc2n1)c1ccnc(F)c1] | 2-Fluoro-N-(6-(2-(4-fluorophenyl)-5-(3-fluoropropyl)-4,5,6,7-tetrahydropyrazolo[1,5-a]pyrazin-3-yl)imidazo[1,2-b]pyridazin-2-yl)isonicotinamide | 533 | 5.70<br>6.67 | A<br>B |
| 29 | 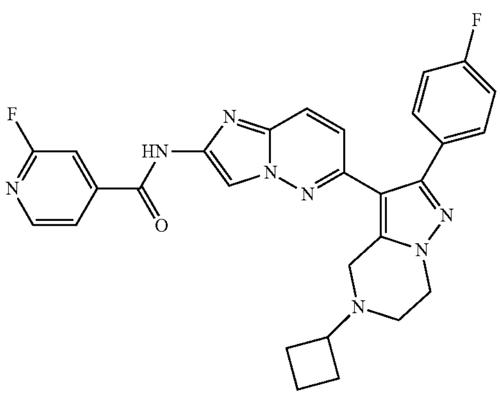 [SMILES: O=C(Nc1cn2nc(-c3c(-c4ccc(F)cc4)nn4c3CN(C3CCC3)CC4)ccc2n1)c1ccnc(F)c1] | N-(6-(5-Cyclobutyl-2-(4-fluorophenyl)-4,5,6,7-tetrahydropyrazolo[1,5-a]pyrazin-3-yl)imidazo[1,2-b]pyridazin-2-yl)-2-fluoroisonicotinamide | 527 | 5.57<br>6.70 | A<br>B |
| 30 | 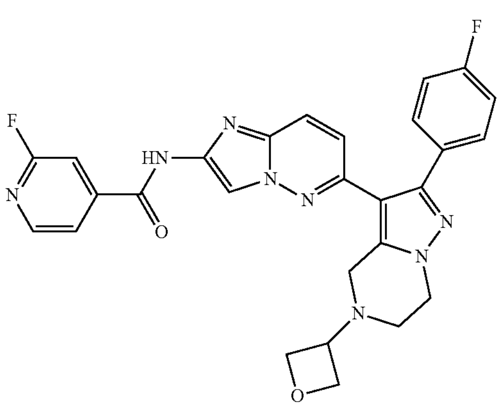 [SMILES: O=C(Nc1cn2nc(-c3c(-c4ccc(F)cc4)nn4c3CN(C3COC3)CC4)ccc2n1)c1ccnc(F)c1] | 2-Fluoro-N-(6-(2-(4-fluorophenyl)-5-(oxetan-3-yl)-4,5,6,7-tetrahydropyrazolo[1,5-a]pyrazin-3-yl)imidazo[1,2-b]pyridazin-2-yl)isonicotinamide | 529 | 8.04<br>7.73 | A<br>B |

Compound 31: N-(6-(5-Cyclopropyl-2-(4-fluorophenyl)-4,5,6,7-tetrahydropyrazolo[1,5-a]pyrazin-3-yl)imidazo[1,2-b]pyridazin-2-yl)-2-fluoroisonicotinamide

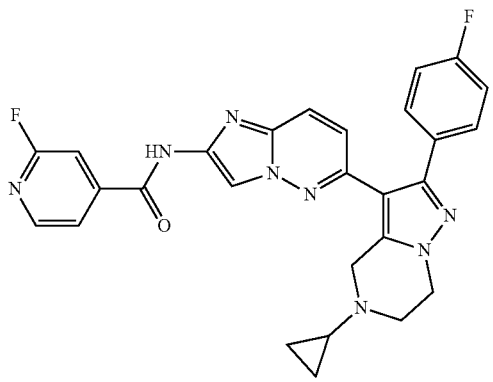 [SMILES: O=C(Nc1cn2nc(-c3c(-c4ccc(F)cc4)nn4c3CN(C3CC3)CC4)ccc2n1)c1ccnc(F)c1]

To a stirred solution of Compound 1 (25 mg, 0.053 mmol) in THF (0.5 mL) and methanol (0.5 mL) were added NaBH$_4$ (4.0 mg, 0.106 mmol) and (1-ethoxycyclopropoxy)trimethylsilane (18.45 mg, 0.106 mmol) and the resulting reaction mixture was stirred at room temperature for 12 h. The reaction mixture was diluted with water and the aqueous layer was back extracted with ethyl acetate (2×20 mL). The combined organic layer was washed with brine, dried over Na$_2$SO$_4$, filtered and concentrated. The crude product was purified by preparative HPLC to afford Compound 31 as pale yellow solid (10 mg, 36%). MS(ES): m/z=511 [M−H]; HPLC Ret. Time 7.57 min and 7.53 min (HPLC Methods A and B, respectively). $^1$H NMR (400 MHz, DMSO-d$_6$) δ ppm 11.84 (s, 1H), 8.47 (t, J=2.51 Hz, 2H), 7.92-7.99 (m, 2H), 7.81 (s, 1H), 7.49-7.54 (m, 2H), 7.21-7.26 (m, 2H), 6.87 (d, J=9.54 Hz, 1H), 4.21 (t, J=5.27 Hz, 2H), 4.03 (s, 2H), 3.18 (t, J=5.27 Hz, 2H), 2.03 (dt, J=6.40, 3.07 Hz, 1H), 0.52-0.58 (m, 2H), 0.42-0.48 (m, 2H).

Compound 32: N-(6-(5-(2,2-Difluoroethyl)-2-(4-fluorophenyl)-4,5,6,7-tetrahydropyrazolo[1,5-a]pyrazin-3-yl)imidazo[1,2-b]pyridazin-2-yl)-2-fluoroisonicotinamide

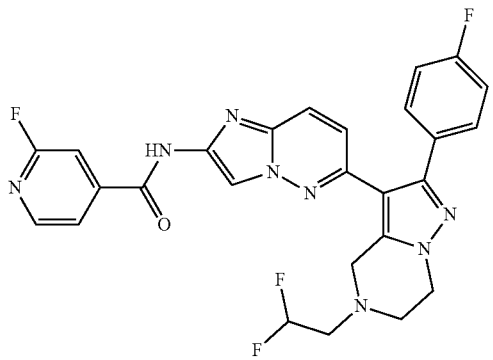 [SMILES: O=C(Nc1cn2nc(-c3c(-c4ccc(F)cc4)nn4c3CN(CC(F)F)CC4)ccc2n1)c1ccnc(F)c1]

To a stirred solution of Compound 1 (25 mg, 0.053 mmol) in DMF (0.5 mL) was added 2,2-difluoroethyl trifluoromethanesulfonate (16.99 mg, 0.079 mmol) and DIPEA (0.018 mL, 0.106 mmol) and the resulting reaction mixture was heated at 60° C. overnight. The reaction completion was monitored by LCMS. The reaction mixture was diluted with water (10 mL) and the aqueous layer was back extracted with ethyl acetate (2×15 mL). The combined organic layer was washed with sodium bicarbonate solution, brine, dried over Na$_2$SO$_4$, filtered and concentrated. Crude product was purified by preparative HPLC to afford Compound 32 as pale yellow solid (17 mg, 60%). MS(ES): m/z=537 [M+H]$^+$; HPLC Ret. Time 16.28 min and 14.75 min (HPLC Methods E and F, respectively). $^1$H NMR (400 MHz, DMSO-d$_6$) δ ppm 11.84 (s, 1H), 8.45-8.51 (m, 2H), 7.92-7.99 (m, 2H), 7.80 (s, 1H), 7.49-7.55 (m, 2H), 7.21-7.29 (m, 2H), 6.85 (d, J=9.54 Hz, 1H), 6.09-6.41 (m, 1H), 4.25 (t, J=5.52 Hz, 2H), 4.10 (s, 2H), 3.20 (t, J=5.52 Hz, 2H), 3.09 (td, J=15.44, 4.27 Hz, 2H).

Compound 33: Methyl 3-(2-(2-fluoroisonicotinamido)imidazo[1,2-b]pyridazin-6-yl)-2-(4-fluorophenyl)-6,7-dihydropyrazolo[1,5-a]pyrazine-5(4H)-carboxylate

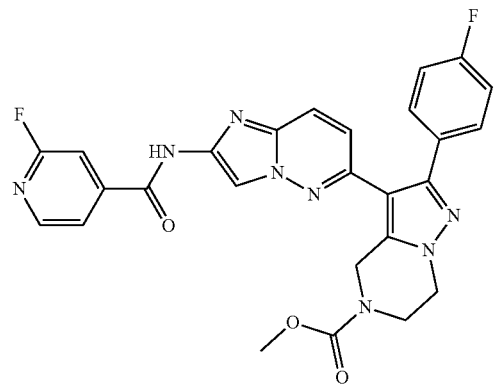 [SMILES: COC(=O)N1CCn2nc(-c3ccc(F)cc3)c(-c3ccc4nc(NC(=O)c5ccnc(F)c5)cn4n3)c2C1]

To a stirred solution of Compound 1 (25 mg, 0.053 mmol) in DMF (2 mL) was added DIPEA (0.028 mL, 0.159 mmol) and methyl carbonochloridate (15.00 mg, 0.159 mmol) and the reaction mixture was stirred at RT for 12 h., diluted with water and extracted with DCM (3×15 mL). The combined organic layer was washed with brine, dried over Na$_2$SO$_4$, filtered and concentrated. Crude was purified by preparative HPLC to afford Compound 33 as pale yellow solid (10 mg, 36%). MS(ES): m/z=531 [M+H]$^+$; HPLC Ret. Time 9.57 min and 13.6 min (HPLC Methods A and F, respectively). $^1$H NMR (400 MHz, DMSO-d$_6$) δ ppm 11.86 (br. s., 1H), 8.45-8.49 (m, 2H), 7.93-8.00 (m, 2H), 7.81 (s, 1H), 7.49-7.55 (m, 2H), 7.23-7.29 (m, 2H), 6.85 (d, J=9.54 Hz, 1H), 4.91 (s, 2H), 4.25-4.31 (m, 2H), 3.99 (t, J=5.27 Hz, 2H), 3.69 (s, 3H).

The Compound shown in Table 4 has been prepared similar to Compound 33 by reaction of Compound 1 with isopropyl chloroformate.

TABLE 4

| Ex. No. | Structure | Name | [M + H]+ | Ret Time (min) | HPLC Method |
|---|---|---|---|---|---|
| 34 | 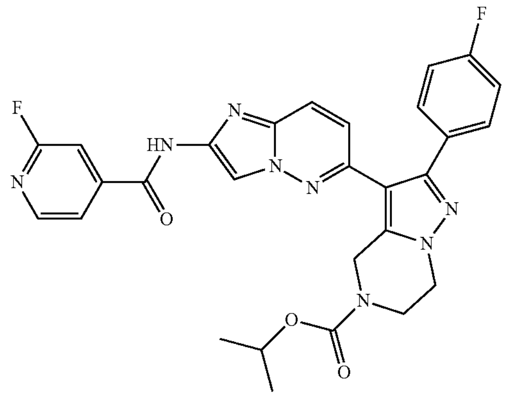 [SMILES: CC(C)OC(=O)N1CCn2nc(-c3ccc(F)cc3)c(-c3ccc4nc(NC(=O)c5ccnc(F)c5)cn4n3)c2C1] | Isopropyl 3-(2-(2-fluoroisonicotinamido)imidazo[1,2-b]pyridazin-6-yl)-2-(4-fluorophenyl)-6,7-dihydropyrazolo[1,5-a]pyrazine-5(4H)-carboxylate | 559 | 17.35<br>15.54 | E<br>F |

Compound 35: 2-Fluoro-N-(6-(2-(4-fluorophenyl)-5-(methylsulfonyl)-4,5,6,7-tetrahydropyrazolo[1,5-a]pyrazin-3-yl)imidazo[1,2-b]pyridazin-2-yl)isonicotinamide

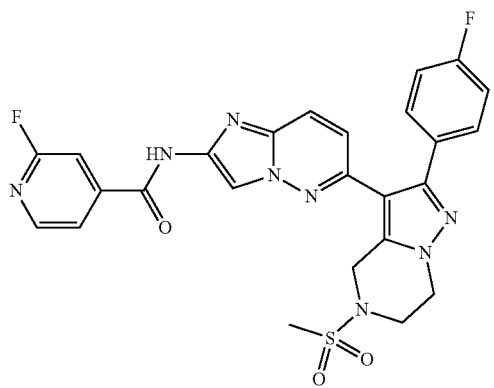 [SMILES: CS(=O)(=O)N1CCn2nc(-c3ccc(F)cc3)c(-c3ccc4nc(NC(=O)c5ccnc(F)c5)cn4n3)c2C1]

To a stirred solution of Compound 1 (25 mg, 0.053 mmol) and methanesulfonyl chloride (12.12 mg, 0.106 mmol) in DMF (0.5 mL) was added DIPEA (0.018 mL, 0.106 mmol) and the resulting reaction mixture was stirred at room temperature for 4 h. The reaction mixture was concentrated under vacuum, diluted with water and the aqueous layer was back extracted with DCM (3×15 mL). The combined the organic layer was washed with brine, dried over $Na_2SO_4$, filtered and concentrated. The crude product was purified by preparative HPLC to afford Compound 35 as a pale yellow solid (15 mg, 51%). MS(ES): m/z=551 [M+H]+; HPLC Ret. time 9.26 min and 8.92 min (HPLC Methods A and B, respectively). $^1$H NMR (400 MHz, DMSO-$d_6$) δ ppm 11.79 (br. s., 1H), 8.53 (s, 1H), 8.46 (d, J=5.52 Hz, 1H), 7.93-7.99 (m, 2H), 7.80 (s, 1H), 7.52-7.57 (m, 2H), 7.23-7.30 (m, 2H), 6.86 (d, J=9.54 Hz, 1H), 4.75 (s, 2H), 4.37 (t, J=5.27 Hz, 2H), 3.83 (t, J=5.52 Hz, 2H), 3.14 (s, 3H).

The Compounds shown in Table 5 have been prepared similar to 35 by coupling of Compound 1 with various sulfonyl chlorides.

TABLE 5

| Ex. No. | Structure | Name | [M + H]+ | Ret Time (min) | HPLC Methods |
|---|---|---|---|---|---|
| 36 | 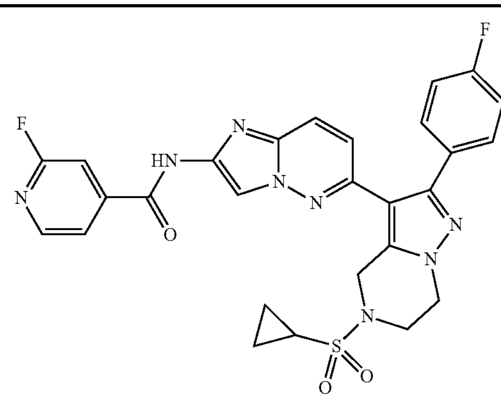 | N-(6-(5-(Cyclopropylsulfonyl)-2-(4-fluorophenyl)-4,5,6,7-tetrahydropyrazolo[1,5-a]pyrazin-3-yl)imidazo[1,2-b]pyridazin-2-yl)-2-fluoroisonicotinamide | 577 | 15.80<br>14.91 | E<br>F |

TABLE 5-continued

| Ex. No. | Structure | Name | [M + H]+ | Ret Time (min) | HPLC Methods |
|---|---|---|---|---|---|
| 37 | 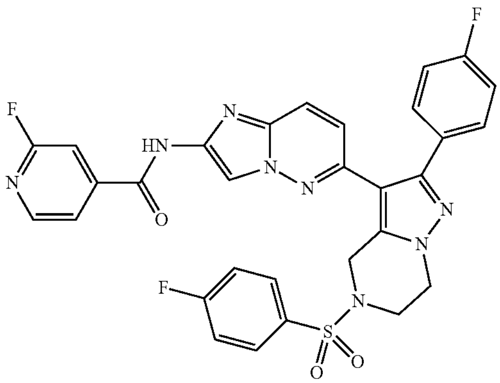 [SMILES: O=C(Nc1cn2nc(-c3c(-c4ccc(F)cc4)nn4c3CN(S(=O)(=O)c3ccc(F)cc3)CC4)ccc2n1)c1ccnc(F)c1] | 2-Fluoro-N-(6-(2-(4-fluorophenyl)-5-((4-fluorophenyl)sulfonyl)-4,5,6,7-tetrahydropyrazolo[1,5-a]pyrazin-3-yl)imidazo[1,2-b]pyridazin-2-yl)isonicotinamide | 629[M − H] | 18.12 16.82 | E F |
| 38 | 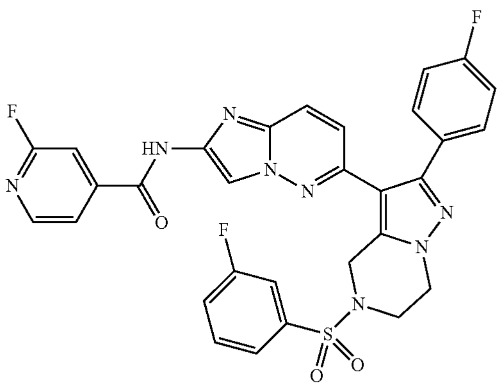 [SMILES: O=C(Nc1cn2nc(-c3c(-c4ccc(F)cc4)nn4c3CN(S(=O)(=O)c3cccc(F)c3)CC4)ccc2n1)c1ccnc(F)c1] | 2-Fluoro-N-(6-(2-(4-fluorophenyl)-5-((3-fluorophenyl)sulfonyl)-4,5,6,7-tetrahydropyrazolo[1,5-a]pyrazin-3-yl)imidazo[1,2-b]pyridazin-2-yl)isonicotinamide | 629[M − H] | 18.17 16.82 | E F |
| 39 | 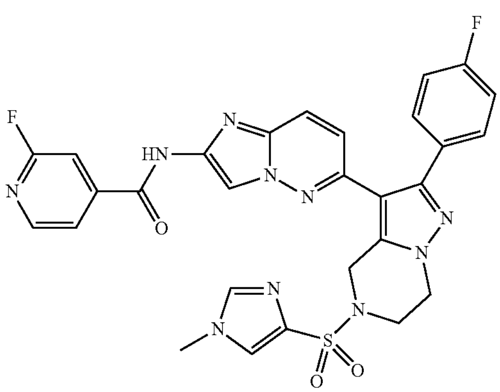 [SMILES: Cn1cnc(S(=O)(=O)N2CCn3nc(-c4ccc(F)cc4)c(-c4ccc5nc(NC(=O)c6ccnc(F)c6)cn5n4)c3C2)c1] | 2-Fluoro-N-(6-(2-(4-fluorophenyl)-5-((1-methyl-1H-imidazol-4-yl)sulfonyl)-4,5,6,7-tetrahydropyrazolo[1,5-a]pyrazin-3-yl)imidazo[1,2-b]pyridazin-2-yl)isonicotinamide | 617 | 9.08 8.85 | A B |
| 40 | 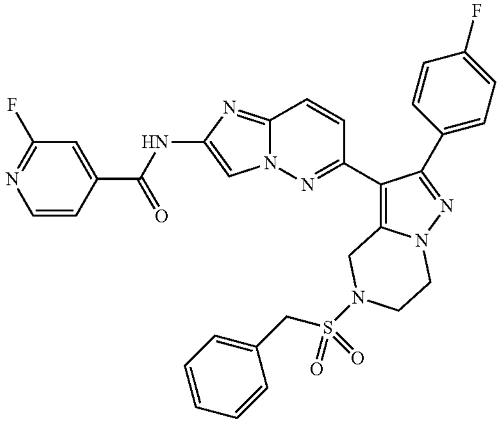 [SMILES: O=C(Nc1cn2nc(-c3c(-c4ccc(F)cc4)nn4c3CN(S(=O)(=O)Cc3ccccc3)CC4)ccc2n1)c1ccnc(F)c1] | N-(6-(5-(Benzylsulfonyl)-2-(4-fluorophenyl)-4,5,6,7-tetrahydropyrazolo[1,5-a]pyrazin-3-yl)imidazo[1,2-b]pyridazin-2-yl)-2-fluoroisonicotinamide | 625[M − H] | 10.88 10.43 | A B |

Compound 41: N-(tert-Butyl)-3-(2-(2-fluoroisonicotinamido)imidazo[1,2-b]pyridazin-6-yl)-2-(4-fluorophenyl)-6,7-dihydropyrazolo[1,5-a]pyrazine-5 (4)-carboxamide

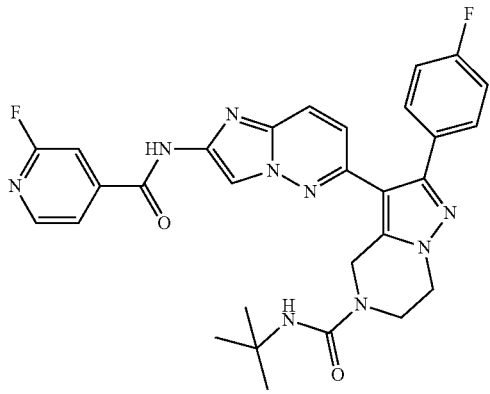 [SMILES: CC(C)(C)NC(=O)N1CCn2nc(-c3ccc(F)cc3)c(-c3ccc4nc(NC(=O)c5ccnc(F)c5)cn4n3)c2C1]

To a stirred solution of Compound 1 (20 mg, 0.042 mmol) in DMF (0.5 mL), was added tert-butylisocyanate (4.20 mg, 0.042 mmol) and it was stirred at RT for 12 h. Water was added and the crude solid product separated was filtered and purified by preparative HPLC to afford Compound 41 (0.013 g, 52%) as pale yellow solid. MS(ES): m/z=572 [M+H]$^+$; HPLC Ret. Time 16.68 min and 14.80 min (HPLC Methods E and F, respectively). $^1$H NMR (400 MHz, DMSO-d$_6$) δ ppm 11.85 (s, 1H), 8.45-8.52 (m, 2H), 7.94-8.00 (m, 2H), 7.81 (s, 1H), 7.50-7.55 (m, 2H), 7.22-7.29 (m, 2H), 6.89 (d, J=9.04 Hz, 1H), 6.26 (s, 1H), 4.79 (s, 2H), 4.21 (t, J=5.02 Hz, 2H), 3.91 (t, J=5.27 Hz, 2H), 1.28 (s, 9H).

The Compounds shown in Table 6 have been prepared similar to Compound 41 by coupling Compound 1 with various isocyanates.

TABLE 6

| Ex. No. | Structure | Name | [M + H]$^+$ | Ret Time (min) | HPLC Methods |
|---|---|---|---|---|---|
| 42 | 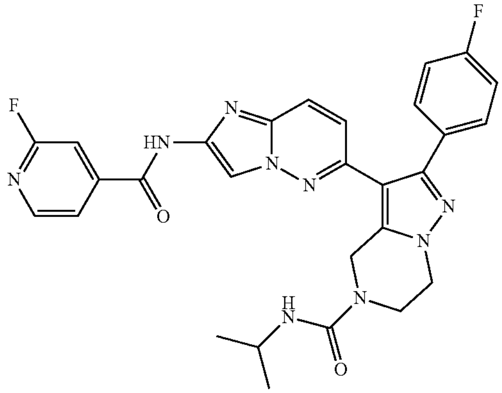 [SMILES: CC(C)NC(=O)N1CCn2nc(-c3ccc(F)cc3)c(-c3ccc4nc(NC(=O)c5ccnc(F)c5)cn4n3)c2C1] | 3-(2-(2-Fluoroisonicotinamido)imidazo[1,2-b]pyridazin-6-yl)-2-(4-fluorophenyl)-N-isopropyl-6,7-dihydropyrazolo[1,5-a]pyrazine-5(4H)-carboxamide | 558 | 15.15<br>1308 | E<br>F |
| 43 | 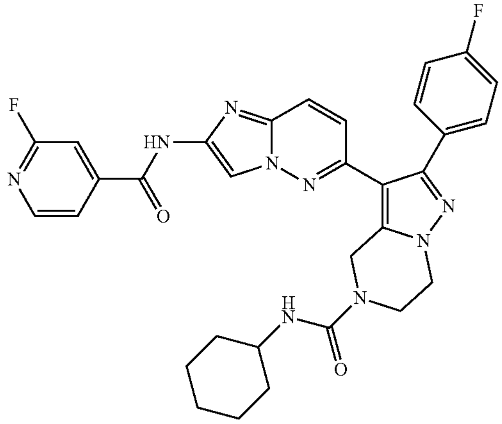 [SMILES: O=C(Nc1cn2nc(-c3c(-c4ccc(F)cc4)nn4c3CN(C(=O)NC3CCCCC3)CC4)ccc2n1)c1ccnc(F)c1] | N-Cyclohexyl-3-(2-(2-fluoroisonicotinamido)imidazo[1,2-b]pyridazin-6-yl)-2-(4-fluorophenyl)-6,7-dihydropyrazolo[1,5-a]pyrazine-5(4H)-carboxamide | 598 | 17.50<br>15.01 | E<br>F |

TABLE 6-continued

| Ex. No. | Structure | Name | [M + H]+ | Ret Time (min) | HPLC Methods |
|---|---|---|---|---|---|
| 44 | 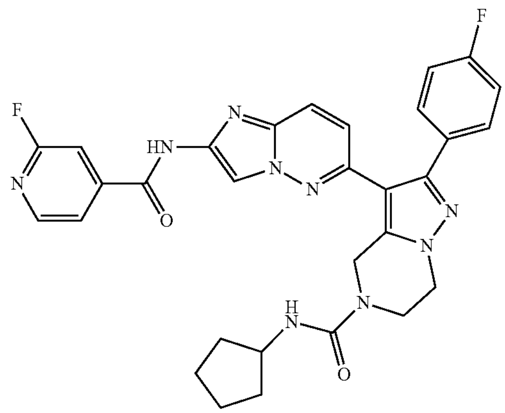 [SMILES: O=C(Nc1cn2nc(-c3c(-c4ccc(F)cc4)nn4c3CN(C(=O)NC3CCCC3)CC4)ccc2n1)c1ccnc(F)c1] | N-Cyclopentyl-3-(2-(2-fluoroisonicotinamido)imidazo[1,2-b]pyridazin-6-yl)-2-(4-fluorophenyl)-6,7-dihydropyrazolo[1,5-a]pyrazine-5(4H)-carboxamide | 584 | 10.34<br>9.51 | A<br>B |
| 45 | 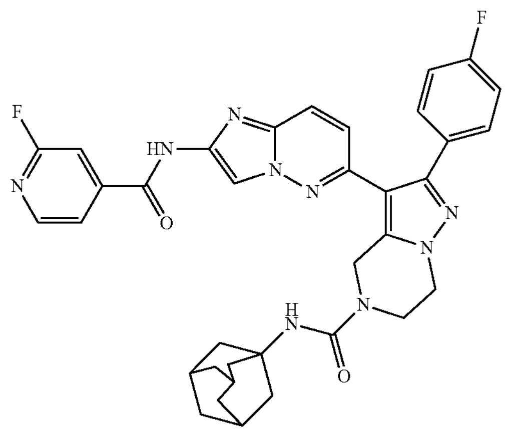 [SMILES: O=C(Nc1cn2nc(-c3c(-c4ccc(F)cc4)nn4c3CN(C(=O)NC35CC6CC(CC(C6)C3)C5)CC4)ccc2n1)c1ccnc(F)c1] | N-(Adamantan-1-yl)-3-(2-(2-fluoroisonicotinamido)imidazo[1,2-b]pyridazin-6-yl)-2-(4-fluorophenyl)-6,7-dihydropyrazolo[1,5-a]pyrazine-5(4H)-carboxamide | 650 | 12.56<br>11.11 | A<br>B |

Compound 46: N-Cyclopropyl-3-(2-(2-fluoroisonicotinamido)imidazo[1,2-b]pyridazin-6-yl)-2-(4-fluorophenyl)-6,7-dihydropyrazolo[1,5-a]pyrazine-5(4H)-carboxamide

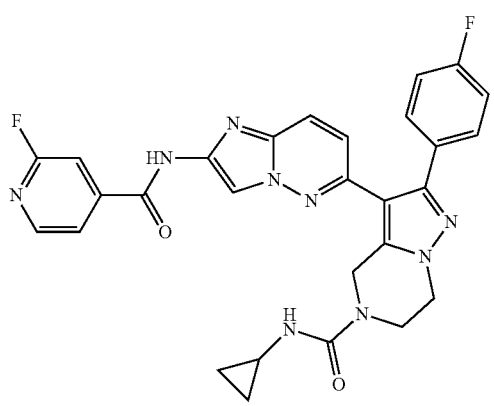 [SMILES: O=C(Nc1cn2nc(-c3c(-c4ccc(F)cc4)nn4c3CN(C(=O)NC3CC3)CC4)ccc2n1)c1ccnc(F)c1]

To a stirred solution of cyclopropylamine (7.25 mg, 0.127 mmol) in DCM (2 mL) and triethylamine (0.018 mL, 0.127 mmol) at 0° C. was added triphosgene (18.84 mg, 0.063 mmol) in DCM and stirred at same temperature for 10 min. Then, Compound 1 (30 mg, 0.063 mmol) dissolved in DMF (1 mL) was added dropwise and stirred at RT for 12 h. The reaction mixture was diluted with water; the aqueous layer was back extracted with DCM (2×15 mL). The combined organic layer was washed with brine, dried over $Na_2SO_4$, filtered and concentrated. The crude product was purified by preparative HPLC to afford Compound 46 (0.013 g, 36%) as a white solid. MS(ES): m/z=556 [M+H]+; HPLC Ret. Time 9.04 min and 8.52 min (HPLC Methods A and B, respectively). $^1$H NMR (400 MHz, DMSO-$d_6$) δ ppm 11.85 (s, 1H), 8.51 (s, 1H), 8.47 (d, J=5.21 Hz, 1H), 7.95-8.00 (m, 2H), 7.81 (s, 1H), 7.52 (dd, J=8.88, 5.55 Hz, 2H), 7.25 (t, J=8.91 Hz, 2H), 6.99 (d, J=2.64 Hz, 1H), 6.87 (d, J=9.41 Hz, 1H), 4.80 (s, 2H), 4.20 (t, J=5.33 Hz, 2H), 3.91 (t, J=5.36 Hz, 2H), 0.57 (dd, J=6.84, 2.13 Hz, 2H), 0.41 (dd, J=3.80, 2.35 Hz, 2H).

The Compounds shown in Table 7 have been prepared similar to Compound 46 by coupling Compound 1 with in-situ isocyanates generated from various amines.

TABLE 7

| Ex. No. | Structure | Name | [M + H]+ | Ret Time (min) | HPLC Methods |
|---|---|---|---|---|---|
| 47 | 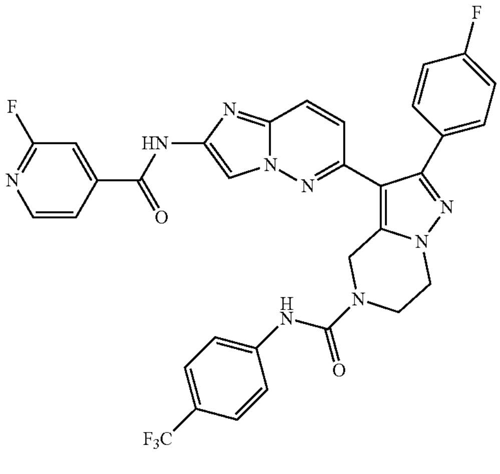 [SMILES: O=C(Nc1cn2nc(-c3c(-c4ccc(F)cc4)nn4c3CN(C(=O)Nc3ccc(C(F)(F)F)cc3)CC4)ccc2n1)c1ccnc(F)c1] | 3-(2-(2-Fluoroisonicotinamido) imidazo[1,2-b]pyridazin-6-yl)-2-(4-fluorophenyl)-N-(4-(trifluoromethyl)phenyl)-6,7-dihydropyrazolo[1,5-a]pyrazine-5(4H)-carboxamide | 660 | 11.61<br>10.72 | A<br>B |
| 48 | 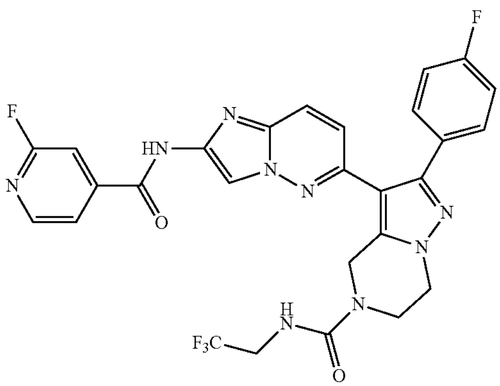 [SMILES: O=C(Nc1cn2nc(-c3c(-c4ccc(F)cc4)nn4c3CN(C(=O)NCC(F)(F)F)CC4)ccc2n1)c1ccnc(F)c1] | 3-(2-(2-Fluoroisonicotinamido) imidazo[1,2-b]pyridazin-6-yl)-2-(4-fluorophenyl)-N-(2,2,2-trifluoroethyl)-6,7-dihydropyrazolo[1,5-a]pyrazine-5(4H)-carboxamide | 598 | 9.79<br>9.25 | A<br>B |

Compound 49: 3-(2-(2-Fluoroisonicotinamido)imidazo[1,2-b]pyridazin-6-yl)-2-(4-fluorophenyl)-N-(pyridin-4-yl)-6,7-dihydropyrazolo[1,5-a]pyrazine-5(4H)-carboxamide

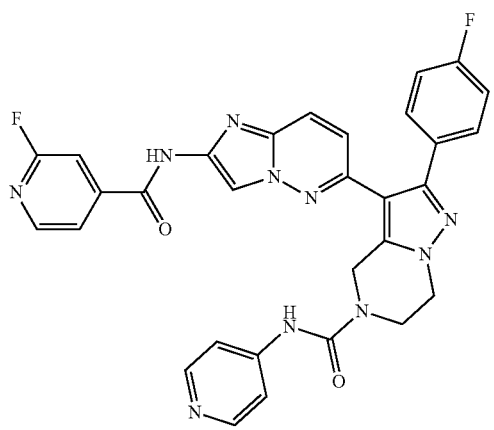 [SMILES: O=C(Nc1cn2nc(-c3c(-c4ccc(F)cc4)nn4c3CN(C(=O)Nc3ccncc3)CC4)ccc2n1)c1ccnc(F)c1]

To a stirred solution of isonicotinic acid (6.51 mg, 0.053 mmol) in toluene (2 mL) was added triethylamine (0.015 mL, 0.106 mmol) and diphenylphosphoryl azide (0.023 mL, 0.106 mmol) and heated at 100° C. for 2 h. The reaction mass was cooled to RT, Compound 1 (25 mg, 0.053 mmol) dissolved in DMF (1 mL) was added dropwise and the resulting reaction mixture was stirred at RT for 12 h., diluted with water. The aqueous layer was extracted with DCM (3×15 mL). The combined organic layer was washed with brine, dried over $Na_2SO_4$, filtered and concentrated. The crude product was purified by preparative HPLC to afford Compound 49 (0.005 g, 15%) as a white solid. MS(ES): m/z=591 [M–H]+; HPLC Ret. Time 6.56 min and 7.57 min (HPLC Methods A and B, respectively). $^1$H NMR (400 MHz, DMSO-$d_6$) δ ppm 11.85 (s, 1H), 9.34 (s, 1H), 8.53 (s, 1H), 8.47 (d, J=5.21 Hz, 1H), 8.30-8.37 (m, 2H), 7.93-8.00 (m, 2H), 7.81 (s, 1H), 7.50-7.58 (m, 2H), 7.45-7.50 (m, 2H), 7.21-7.31 (m, 2H), 6.89 (d, J=9.41 Hz, 1H), 5.03 (s, 2H), 4.34 (t, J=5.21 Hz, 2H), 4.07-4.15 (t, J=5.21 Hz, 2H).

The Compounds shown in Table 8 have been prepared similar to Compound 49 by coupling Compound 1 with in-situ isocyanates generated from various carboxylic acids.

TABLE 8

| Ex. No. | Structure | Name | [M + H]+ | Ret Time (min) | HPLC Methods |
|---|---|---|---|---|---|
| 50 | 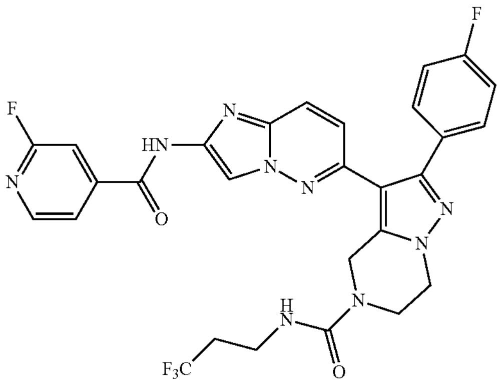 [SMILES: O=C(Nc1cn2nc(-c3c(-c4ccc(F)cc4)nn4c3CN(C(=O)NCCC(F)(F)F)CC4)ccc2n1)c1ccnc(F)c1] | 3-(2-(2-Fluoroisonicotinamido)imidazo[1,2-b]pyridazin-6-yl)-2-(4-fluorophenyl)-N-(3,3,3-trifluoropropyl)-6,7-dihydropyrazolo[1,5-a]pyrazine-5(4H)-carboxamide | 610[M − H] | 10.13 9.48 | A B |
| 51 | 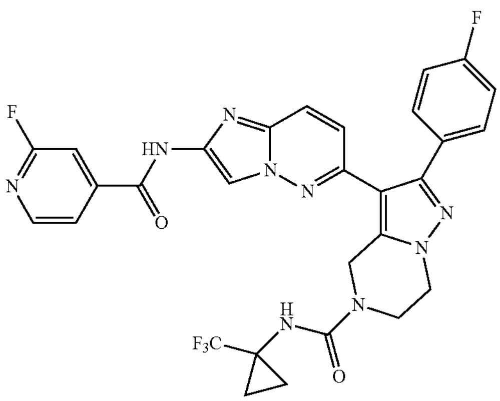 [SMILES: O=C(Nc1cn2nc(-c3c(-c4ccc(F)cc4)nn4c3CN(C(=O)NC3(C(F)(F)F)CC3)CC4)ccc2n1)c1ccnc(F)c1] | 3-(2-(2-Fluoroisonicotinamido)imidazo[1,2-b]pyridazin-6-yl)-2-(4-fluorophenyl)-N-(1-(trifluoromethyl)cyclopropyl)-6,7-dihydropyrazolo[1,5-a]pyrazine-5(4H)-carboxamide | 624 | 10.00 9.42 | A B |
| 52 | 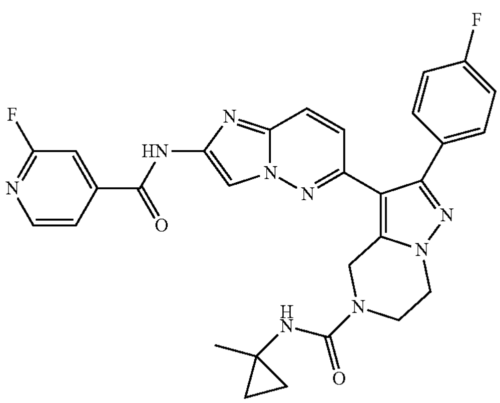 [SMILES: CC1(NC(=O)N2CCn3nc(-c4ccc(F)cc4)c(-c4ccc5nc(NC(=O)c6ccnc(F)c6)cn5n4)c3C2)CC1] | 3-(2-(2-Fluoroisonicotinamido)imidazo[1,2-b]pyridazin-6-yl)-2-(4-fluorophenyl)-N-(1-methylcyclopropyl)-6,7-dihydropyrazolo[1,5-a]pyrazine-5(4H)-carboxamide | 568[M − H] | 9.57 8.88 | A B |

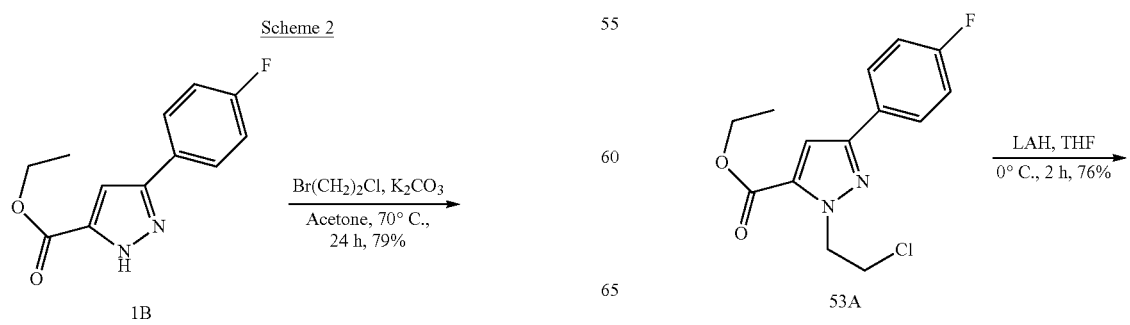

Scheme 2

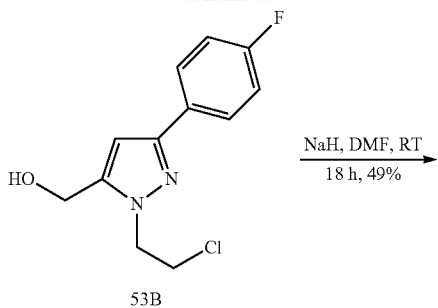

53B

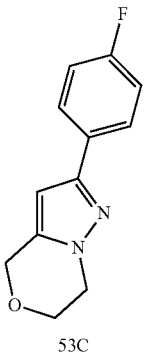

53C

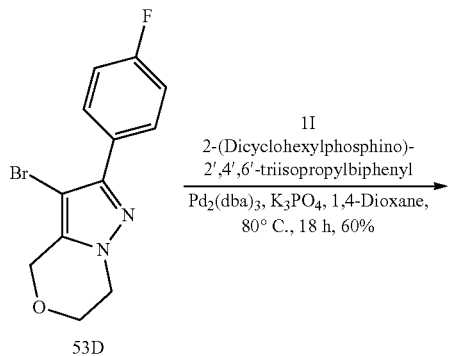

53D

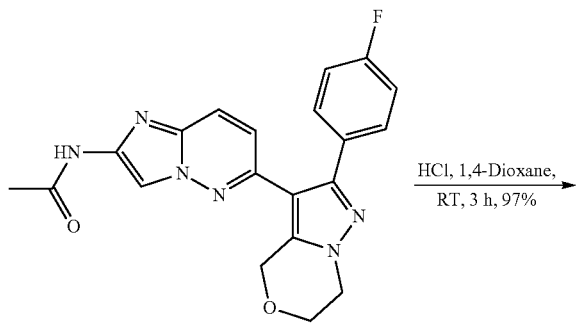

53E

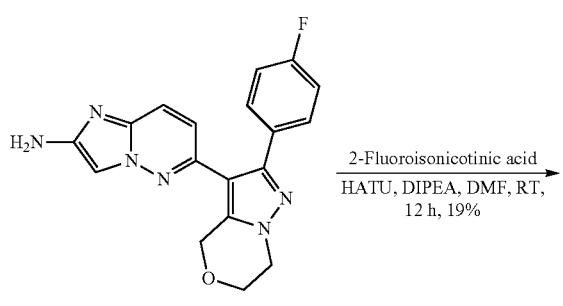

53F

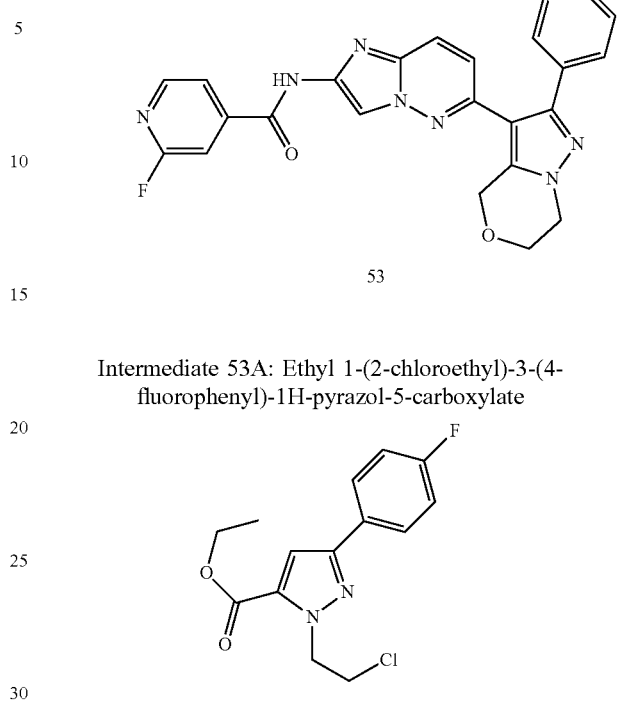

53

Intermediate 53A: Ethyl 1-(2-chloroethyl)-3-(4-fluorophenyl)-1H-pyrazol-5-carboxylate To a solution of Intermediate 1B (0.5 g, 2.135 mmol) and 1-bromo-2-chloroethane (0.885 mL, 10.67 mmol) in acetone (10 mL) was added $K_2CO_3$ (0.885 g, 6.40 mmol) and the reaction mixture was stirred at 70° C. for 24 h. Acetone was removed under reduced pressure and the residue was diluted with ice cold water and extracted with ethyl acetate (3×10 mL). The combined organic layer was washed with water, brine, dried over $Na_2SO_4$, filtered and concentrated to afford crude product as yellow solid. The residue was purified by silica gel chromatography (40 g REDISEP® column, eluting with 50% EtOAc in hexane). The collected fractions were concentrated together to afford Intermediate 53A (0.5 g, 79%) as yellow solid. MS(ES): m/z=297 [M+H]$^+$; $^1$H NMR (300 MHz, chloroform-d) δ ppm 7.79 (dd, J=8.95, 5.36 Hz, 2H), 7.07-7.17 (m, 3H), 4.95 (t, J=6.66 Hz, 2H), 4.41 (q, J=7.13 Hz, 2H), 3.95 (t, J=6.66 Hz, 2H), 1.43 (t, J=7.13 Hz, 3H).

Intermediate 53B: (1-(2-Chloroethyl)-3-(4-fluorophenyl)-1H-pyrazol-5-yl)methanol

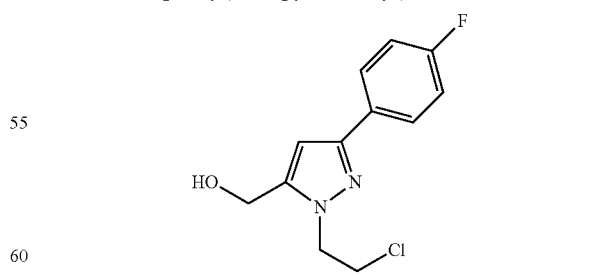

To a solution of Intermediate 53A (12 g, 42.4 mmol) in tetrahydrofuran (100 mL) at 0° C. was added LAH (16.98 mL, 2.4 M solution in THF, 42.4 mmol) and the reaction mixture was stirred at 0° C. for 2 h. The reaction mixture was quenched with 10% NaOH, filtered through CELITE® and the aqueous layer was extracted with ethyl acetate (3×50 mL). The combined organic layer was washed with water, brine, dried over Na$_2$SO$_4$, filtered and concentrated to afford Intermediate 53B (9.5 g, 76%) as off-white solid, which was taken to the next step without further purification. MS(ES): m/z=255 [M+H]; $^1$H NMR (400 MHz, chloroform-d) δ ppm 7.70-7.79 (m, 2H), 7.02-7.13 (m, 2H), 6.46 (s, 1H), 4.77 (d, J=5.71 Hz, 2H), 4.51 (t, J=6.31 Hz, 2H), 3.99 (t, J=6.27 Hz, 2H), 1.73-1.83 (m, 1H).

Intermediate 53C: 2-(4-Fluorophenyl)-6,7-dihydro-4H-pyrazolo[5,1-c][1,4]oxazine

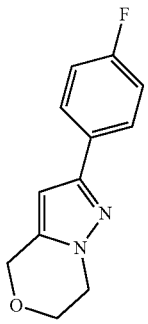 [SMILES: Fc1ccc(-c2cc3n(n2)CCOC3)cc1]

To a solution of Intermediate 53B (9.5 g, 37.3 mmol) in DMF (10 mL) at 0° C. under nitrogen was added NaH (60% suspension, 1.492 g, 37.3 mmol) and the reaction mixture was stirred at room temperature for 18 h. The reaction mixture was quenched with ice and the aqueous layer was extracted with ethyl acetate (3×10 mL). The combined organic layer was washed with water, brine, dried over Na$_2$SO$_4$, filtered and concentrated to afford crude compound as brown semisolid. The residue was further purified by silica gel chromatography (24 g REDISEP® column, eluting with 30% EtOAc in hexane). Collected fractions were concentrated together to afford Intermediate 53C (4 g, 49%) as an off-white solid. MS(ES): m/z=219 [M+H]$^+$; $^1$H NMR (400 MHz, chloroform-d) δ ppm 12.45-12.54 (m, 2H), 11.80-11.89 (m, 2H), 11.02 (t, J=0.75 Hz, 1H), 9.64 (d, J=0.44 Hz, 2H), 8.97-9.06 (m, 2H), 8.86-8.95 (m, 2H).

Intermediate 53D: 3-Bromo-2-(4-fluorophenyl)-6,7-dihydro-4H-pyrazolo[5,1-c][1,4]oxazine

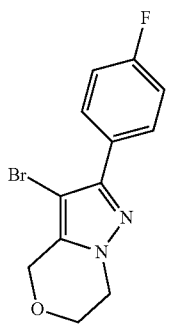 [SMILES: Fc1ccc(-c2nn3c(c2Br)COCC3)cc1]

To a solution of Intermediate 53C (1.2 g, 5.50 mmol) in DCM (20 mL) was added NBS (1.028 g, 5.77 mmol) and the mixture was stirred at room temperature for 18 h. DCM was removed under reduced pressure, and the residue was triturated with water and the solid product obtained was filtered through Buchner funnel, washed with water to afford crude compound as off-white solid. The residue was purified by silica gel chromatography (40 g REDISEP® column, eluting with 30% EtOAc in hexane). The collected fractions were concentrated together to afford Intermediate 53D (1.2 g, 73%) as a white solid. MS(ES): m/z=299 [M+H]$^+$; $^1$H NMR (400 MHz, chloroform-d) δ ppm 7.81-7.92 (m, 2H), 7.06-7.20 (m, 2H), 4.78 (s, 2H), 4.18-4.22 (m, 2H), 4.11-4.16 (m, 2H).

Intermediate 53E: N-(6-(2-(4-Fluorophenyl)-6,7-dihydro-4H-pyrazolo[5,1-c][1,4]oxazin-3-yl)imidazo[1,2-b]pyridazin-2-yl)acetamide

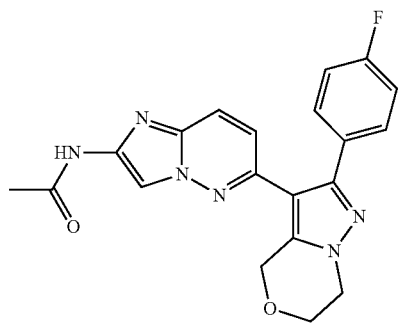 [SMILES: CC(=O)Nc1cn2nc(-c3c(-c4ccc(F)cc4)nn4c3COCC4)ccc2n1]

To a solution of Intermediate 53D (200 mg, 0.673 mmol), Intermediate 1I (610 mg, 2.019 mmol), and K$_3$PO$_4$ (428 mg, 2.019 mmol) in 1,4-dioxane (5 mL) was added Pd$_2$(dba)$_3$ (61.6 mg, 0.067 mmol) and 2-(dicyclohexylphosphino)-2',4',6'-triisopropylbiphenyl (64.2 mg, 0.135 mmol). The reaction mixture was degassed for 15 min. and stirred at 80° C. for 18 h. The reaction mixture was cooled to RT, filtered through CELITE® and the filtrate was evaporated under reduced pressure. The residue obtained was diluted with water and the aqueous layer was extracted with EtOAc (3×5 mL). The combined organic layer was and washed with brine, dried over Na$_2$SO$_4$, filtered and concentrated to give crude compound a yellow solid. The residue was purified by silica gel chromatography (40 g REDISEP® column, eluting with 2% methanol in chloroform). The collected fractions were concentrated together to afford Intermediate 53E (0.16 g, 60%) as a white solid. MS(ES): m/z=393 [M+H]$^+$; $^1$H NMR (400 MHz, DMSO-d$_6$) δ ppm 10.86 (s, 1H), 8.22 (s, 1H), 7.83 (dd, J=9.41, 0.63 Hz, 1H), 7.49-7.56 (m, 2H), 7.21-7.29 (m, 2H), 6.77 (d, J=9.41 Hz, 1H), 5.04 (s, 2H), 4.22-4.29 (m, 2H), 4.13-4.20 (m, 2H), 2.11 (s, 3H).

Intermediate 53F: 6-(2-(4-Fluorophenyl)-6,7-dihydro-4H-pyrazolo[5,1-c][1,4]oxazin-3-yl)imidazo[1,2-b]pyridazin-2-amine

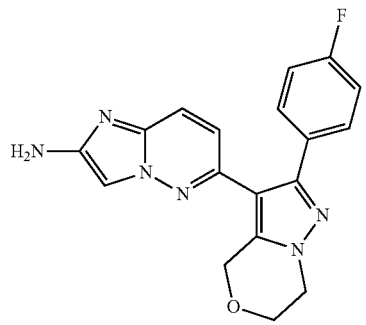 [SMILES: Nc1cn2nc(-c3c(-c4ccc(F)cc4)nn4c3COCC4)ccc2n1]

To a solution of Intermediate 53E (150 mg, 0.382 mmol) in MeOH (1 mL) at 0° C. was added 4 M HCl in 1,4-dioxane (1.434 mL, 5.73 mmol) and it stirred at room temperature for 3 h. Solvents were removed under reduced pressure, the residue was basified to pH ~8.0 using 10% aq. NaHCO$_3$ solution and extracted with ethyl acetate (3×15 mL). The combined organic layer was washed with 10% NaHCO$_3$, brine dried over Na$_2$SO$_4$, filtered and concentrated to afford crude Intermediate 53F (0.13 g, 97%) as a yellow solid. This was used to the next step without further purification. MS(ES): m/z=351 [M+H]$^+$; $^1$H NMR (400 MHz, DMSO-d$_6$) δ ppm 7.44-7.57 (m, 3H), 7.19-7.29 (m, 3H), 6.58 (d, J=9.16 Hz, 1H), 5.44 (s, 2H), 4.98 (s, 2H), 4.20-4.27 (m, 2H), 4.11-4.18 (m, 2H).

Intermediate 53: 2-Fluoro-N-(6-(2-(4-fluorophenyl)-6,7-dihydro-4H-pyrazolo[5,1-c][1,4]oxazin-3-yl) imidazo[1,2-b]pyridazin-2-yl)isonicotinamide

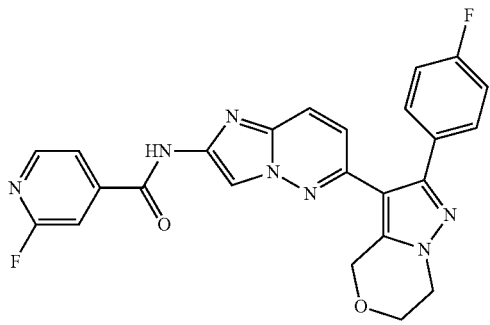 [SMILES: O=C(Nc1cn2nc(-c3c(-c4ccc(F)cc4)nn4c3COCC4)ccc2n1)c1ccnc(F)c1]

A solution of 2-fluoroisonicotinic acid (45.3 mg, 0.321 mmol), HATU (122 mg, 0.321 mmol), and DIPEA (0.067 mL, 0.385 mmol) in DMF (2 mL) was stirred for 15 min., and then Intermediate 53F (45 mg, 0.128 mmol) was added and the reaction mixture was stirred at room temperature for 18 h. The reaction mixture was diluted with water (5 mL) and extracted with EtOAc (3×5 mL). The combined organic layer was washed with water, brine, dried over Na$_2$SO$_4$, filtered and concentrated to afford the crude compound as a dark brown residue. The crude was purified by preparative HPLC to afford Compound 53 (0.012 g, 19%) as pale yellow solid. MS(ES): m/z=474 [M+H]$^+$; HPLC Ret. Time 9.74 min and 8.67 min. (HPLC Methods A and B, respectively); $^1$H NMR (400 MHz, DMSO-d$_6$) δ ppm 11.83 (br. s., 1H), 8.44-8.50 (m, 2H), 7.96 (d, J=5.02 Hz, 1H), 7.92 (d, J=9.29 Hz, 1H), 7.80 (s, 1H), 7.51-7.58 (m, 2H), 7.27 (t, J=8.91 Hz, 2H), 6.84 (d, J=9.54 Hz, 1H), 5.07 (s, 2H), 4.26 (d, J=5.27 Hz, 2H), 4.19 (d, J=5.02 Hz, 2H).

The Compounds shown in Table 9 have been prepared similar to Compound 53 by coupling Compound 53F with various carboxylic acids.

TABLE 9

| Ex. No. | Structure | Name | [M − H]$^+$ | Ret Time (min) | HPLC Methods |
|---|---|---|---|---|---|
| 54 | 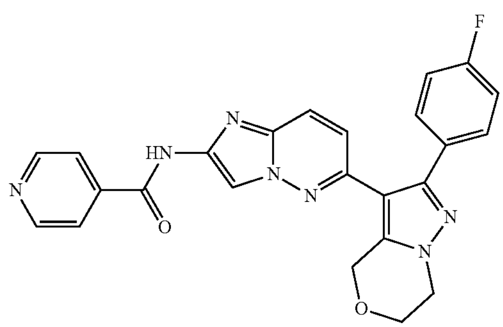 [SMILES: O=C(Nc1cn2nc(-c3c(-c4ccc(F)cc4)nn4c3COCC4)ccc2n1)c1ccncc1] | N-(6-(2-(4-Fluorophenyl)-6,7-dihydro-4H-pyrazolo[5,1-c][1,4]oxazin-3-yl)imidazo[1,2-b]pyridazin-2-yl)isonicotinamide | 454 | 6.76<br>6.63 | A<br>B |
| 55 | 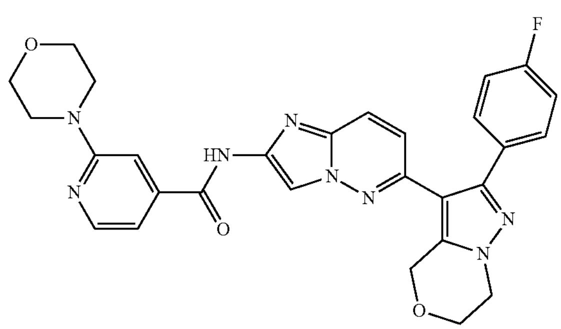 | N-(6-(2-(4-Fluorophenyl)-6,7-dihydro-4H-pyrazolo[5,1-c][1,4]oxazin-3-yl)imidazo[1,2-b]pyridazin-2-yl)-2-morpholinoisonicotinamide | 539 | 6.94<br>7.14 | A<br>B |

TABLE 9-continued

| Ex. No. | Structure | Name | [M − H]+ | Ret Time (min) | HPLC Methods |
|---|---|---|---|---|---|
| 56 | 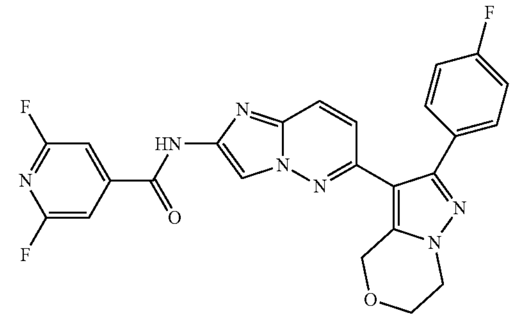 [SMILES: O=C(Nc1cn2nc(-c3c(-c4ccc(F)cc4)nn4c3COCC4)ccc2n1)c1cc(F)nc(F)c1] | 2,6-Difluoro-N-(6-(2-(4-fluorophenyl)-6,7-dihydro-4H-pyrazolo[5,1-c][1,4]oxazin-3-yl)imidazo[1,2-b]pyridazin-2-yl)isonicotinamide | 490 | 10.86 9.67 | A B |
| 57 | 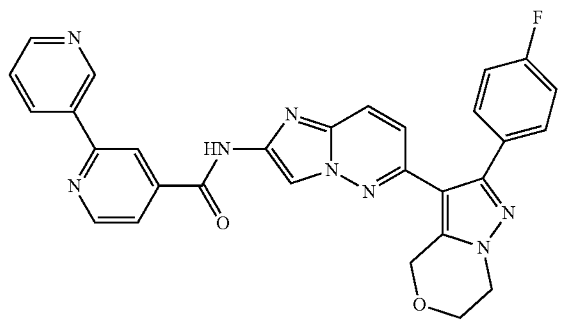 [SMILES: O=C(Nc1cn2nc(-c3c(-c4ccc(F)cc4)nn4c3COCC4)ccc2n1)c1ccnc(-c2cccnc2)c1] | N-(6-(2-(4-Fluorophenyl)-6,7-dihydro-4H-pyrazolo[5,1-c][1,4]oxazin-3-yl)imidazo[1,2-b]pyridazin-2-yl)-[2,3'-bipyridine]-4-carboxamide | 530 | 6.71 7.224 | A B |
| 58 | 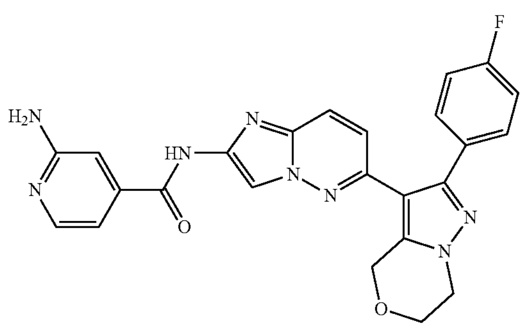 [SMILES: Nc1cc(C(=O)Nc2cn3nc(-c4c(-c5ccc(F)cc5)nn5c4COCC5)ccc3n2)ccn1] | 2-Amino-N-(6-(2-(4-fluorophenyl)-6,7-dihydro-4H-pyrazolo[5,1-c][1,4]oxazin-3-yl)imidazo[1,2-b]pyridazin-2-yl)isonicotinamide | 469 | 5.72 6.39 | A B |

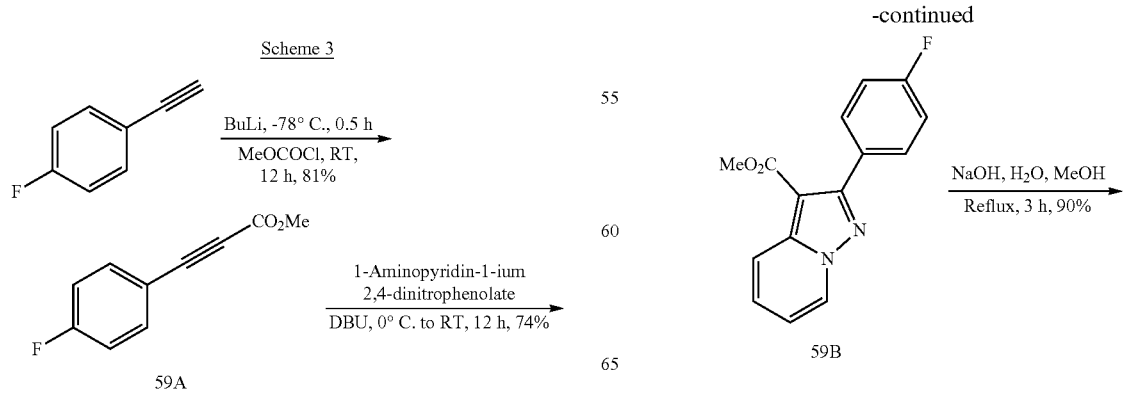

Scheme 3

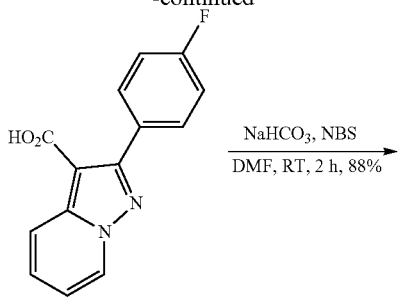

59C

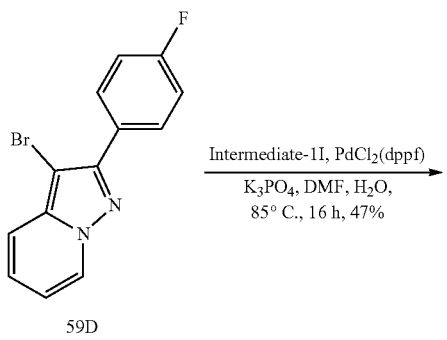

59D

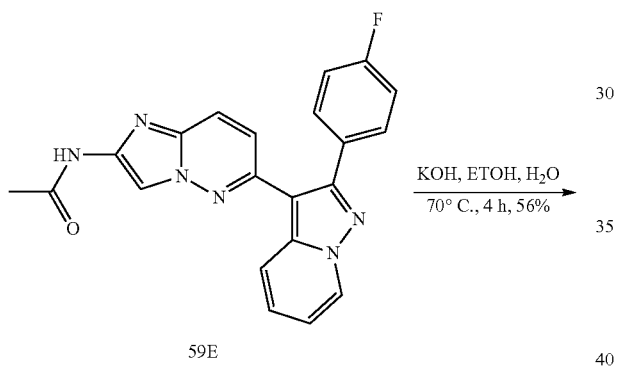

59E

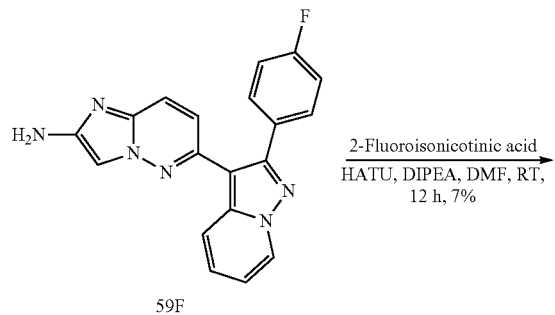

59F

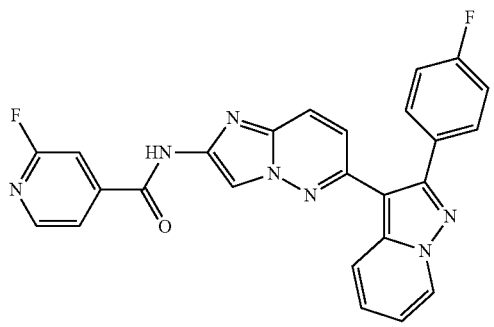

59

Intermediate 59A: Methyl 3-(4-fluorophenyl)propiolate

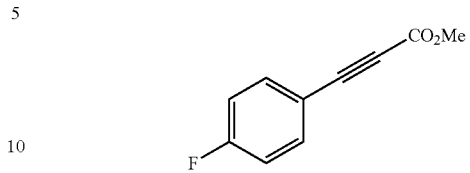

To a solution of 1-ethynyl-4-fluorobenzene (2 g, 16.65 mmol) in THF (15 mL) at −78° C. was added n-butyllithium (7.99 mL, 19.98 mmol) and the resulting solution was stirred at −78° C. for 30 min. Methyl carbonochloridate (1.89 g, 19.98 mmol) in THF (5 mL) was then added and stirring was continued at −78° C. for 30 min. and then slowly warmed to room temperature and stirred for 12 h. The reaction mixture was quenched with ammonium chloride solution and the aqueous layer was extracted with ethyl acetate (3×50 mL). The combined organic layer was and washed with brine, dried over $Na_2SO_4$, filtered and concentrated. The residue was purified silica gel chromatography (40 g REDISEP® column, eluting with 5% EtOAc in hexane). The collected fractions were concentrated together to afford Intermediate 59A (2.4 g, 81%) as a yellow solid. $^1$H NMR (300 MHz, chloroform-d) δ ppm 7.57-7.65 (m, 2H), 7.05-7.15 (m, 2H), 3.86 (s, 3H).

Intermediate 59B: Methyl 2-(4-fluorophenyl)pyrazolo[1,5-a]pyridine-3-carboxylate

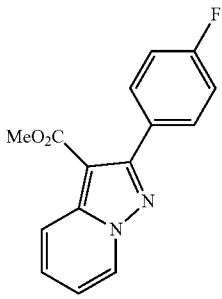 [SMILES: COC(=O)c1c(-c2ccc(F)cc2)nn2ccccc12]

To a stirred solution of 1-aminopyridin-1-ium 2,4-dinitrophenolate (3.7 g, 13.30 mmol) and Intermediate 59A (2.4 g, 13.47 mmol) in THF (25 mL) was added DBU (4.06 mL, 26.9 mmol) dropwise at 0° C. over a period of 10 min. and the resulting brown color solution was stirred at RT for 12 h. THF was removed completely under reduced pressure, crude product was diluted with water (100 mL) and the aqueous layer was extracted with ethyl acetate (3×50 mL). The combined the organic layer was washed with brine, dried over $Na_2SO_4$, filtered and concentrated. The residue was purified by silica gel chromatography (40 g REDISEP® column, eluting with 2% methanol in chloroform). Collected fractions were concentrated together to afford Intermediate 59B (2.7 g, 74%) as a yellow solid. MS(ES): m/z=271 [M+H]; $^1$H NMR (400 MHz, chloroform-d) δ ppm 8.52 (dd, J=6.90, 1.07 Hz, 1H), 8.20 (dd, J=8.94, 1.04 Hz, 1H), 7.76-7.85 (m, 2H), 7.43 (ddd, J=8.97, 6.90, 1.07 Hz, 1H), 7.09-7.21 (m, 2H), 6.98 (td, J=6.89, 1.22 Hz, 1H), 3.82-3.89 (m, 3H).

Intermediate 59C: 2-(4-Fluorophenyl)pyrazolo[1,5-a]pyridine-3-carboxylic acid

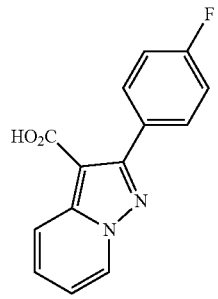 [SMILES: O=C(O)c1c(-c2ccc(F)cc2)nn2ccccc12]

A solution of Intermediate 59B (2.70 g, 9.99 mmol) in 2N aqueous sodium hydroxide (9.99 mL, 19.98 mmol) and methanol (30 mL) was stirred at reflux temperature for 3 h. Methanol was removed under reduced pressure and the aqueous layer was acidified with 1.5N HCl solution. The solid separated out was filtered, washed with water, dried under vacuum to afford Intermediate 59C (2.3 g, 90%) as a white solid. MS(ES): m/z=257 [M+H]$^+$; $^1$H NMR (300 MHz, DMSO-d$_6$) δ ppm 8.84 (dt, J=6.89, 1.01 Hz, 1H), 8.16 (dt, J=8.90, 1.22 Hz, 1H), 7.77-7.89 (m, 2H), 7.58 (ddd, J=8.95, 6.92, 1.09 Hz, 1H), 7.24-7.35 (m, 2H), 7.16 (td, J=6.89, 1.42 Hz, 1H).

Intermediate 59D: 3-Bromo-2-(4-fluorophenyl)pyrazolo[1,5-a]pyridine

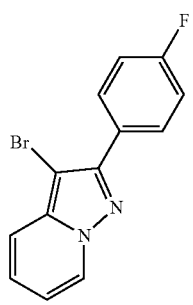 [SMILES: Fc1ccc(-c2nn3ccccc3c2Br)cc1]

To a solution of Intermediate 59C (1 g, 3.90 mmol) and sodium bicarbonate (0.984 g, 11.71 mmol) in dry DMF (10 mL) was added NBS (0.695 g, 3.90 mmol) and the reaction was stirred at RT for 2 h. The reaction mixture was diluted with water. The solid separated was filtered, washed with water and dried under vacuum to afford Intermediate 59D (1 g, 88%) as a white solid. MS(ES): m/z=290 [M+H]$^+$; $^1$H NMR (300 MHz, DMSO-d$_6$) δ ppm 8.78 (d, J=6.99 Hz, 1H), 7.97-8.10 (m, 2H), 7.58-7.67 (m, 1H), 7.31-7.47 (m, 3H), 7.05 (td, J=6.88, 1.35 Hz, 1H).

Intermediate 59E: N-(6-(2-(4-Fluorophenyl)pyrazolo[1,5-a]pyridin-3-yl)imidazo[1,2-b]pyridazin-2-yl)acetamide

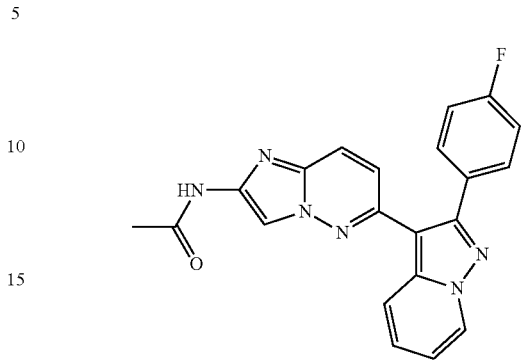

To a degassed solution of Intermediate 59D (0.8 g, 2.75 mmol), Intermediate II (2.08 g, 6.87 mmol) and K$_3$PO$_4$ (1.436 g, 8.24 mmol) in DMF (8 mL) and water (0.8 mL) was added PdCl$_2$(dppf) (0.121 g, 0.165 mmol). The reaction mixture was degassed with nitrogen for 10 min. and stirred at 85° C. for 16 h. DMF was removed under vacuum and the crude product was diluted with ethyl acetate and filtered. The organic layer was washed with water, brine, dried over Na$_2$SO$_4$, filtered and concentrated. The residue was purified silica gel chromatography (40 g REDISEP® column, eluting with 3% methanol in chloroform). Collected fractions were concentrated together to afford Intermediate 59E (0.5 g, 47%) as a pale yellow solid. MS(ES): m/z=387 [M+H]$^+$; $^1$H NMR (400 MHz, DMSO-d$_6$) δ ppm 10.88 (s, 1H), 8.86 (dt, J=6.92, 1.00 Hz, 1H), 8.28-8.35 (m, 1H), 8.15 (dt, J=8.96, 1.17 Hz, 1H), 7.88 (dd, J=9.41, 0.63 Hz, 1H), 7.63-7.73 (m, 2H), 7.48 (ddd, J=8.96, 6.79, 1.07 Hz, 1H), 7.27-7.38 (m, 2H), 7.13 (td, J=6.85, 1.35 Hz, 1H), 6.90 (d, J=9.41 Hz, 1H), 2.12 (s, 3H).

Intermediate 59F: 6-(2-(4-Fluorophenyl)pyrazolo[1,5-a]pyridin-3-yl)imidazo[1,2-b]pyridazin-2-amine

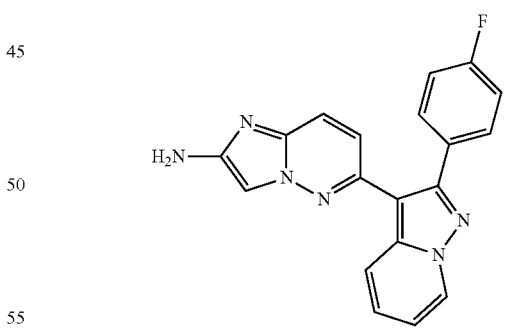

To a solution of Intermediate 59E (0.30 g, 0.776 mmol) in ethanol (6 mL) was added potassium hydroxide (218 mg, 3.88 mmol) in water (3 mL). The resulting reaction mixture was heated at 70° C. for 4 h. Ethanol was removed under high vacuum, residue was diluted with water and aqueous layer was extracted with DCM (2×50 mL). The combined organic layer was washed with water, brine, dried over Na$_2$SO$_4$, filtered and concentrated to afford Intermediate 59F (0.15 g, 56%) as pale yellow solid. MS(ES): m/z=345 [M+H]$^+$. This was taken to the next step without further purification.

Intermediate 59: 2-Fluoro-N-(6-(2-(4-fluorophenyl)pyrazolo[1,5-a]pyridin-3-yl)imidazo [1,2-b]pyridazin-2-yl)isonicotinamide Scheme 4

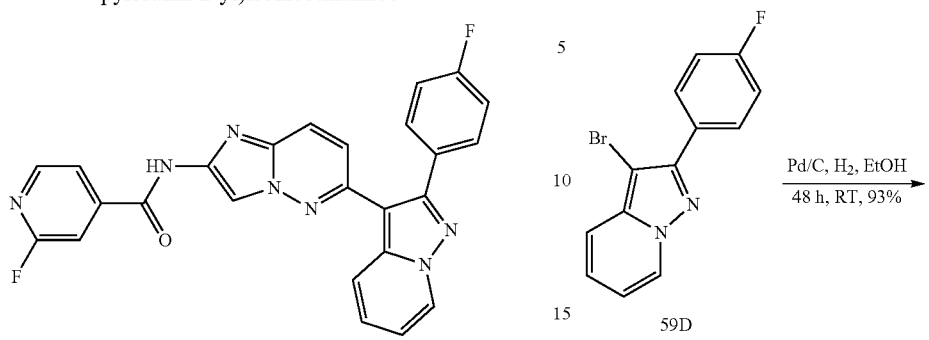

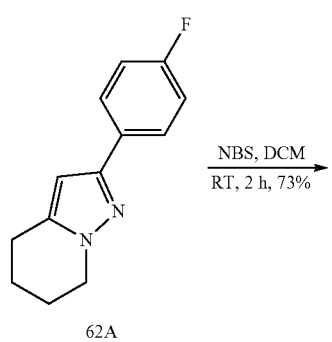

To a solution of Intermediate 59F (50 mg, 0.145 mmol), 2-fluoroisonicotinic acid (41.0 mg, 0.290 mmol) and HATU (110 mg, 0.290 mmol) in DMF (2 mL) was added DIPEA (0.076 mL, 0.436 mmol) and the reaction mixture was stirred at RT for 12 h. The reaction mixture was diluted with water (15 mL) and the aqueous layer was extracted with ethyl acetate (3×15 mL). The combined organic layer was washed with brine, dried over $Na_2SO_4$, filtered and concentrated. The crude was purified by preparative HPLC to afford Compound 59 (0.005 g, 7%) as a yellow solid. MS(ES): m/z=466 [M−H]$^+$; HPLC Ret. Time 18.00 min and 15.44 min (HPLC Methods C and D, respectively); $^1$H NMR (400 MHz, DMSO-$d_6$) δ ppm 8.88 (d, J=6.96 Hz, 1H), 8.57 (s, 1H), 8.47 (d, J=5.15 Hz, 1H), 8.20 (d, J=8.91 Hz, 1H), 7.94-8.01 (m, 2H), 7.82 (s, 1H), 7.69-7.74 (m, 2H), 7.51 (ddd, J=9.00, 6.84, 1.04 Hz, 1H), 7.30-7.37 (m, 2H), 7.15 (td, J=6.85, 1.35 Hz, 1H), 6.97 (d, J=9.41 Hz, 1H).

The Compounds described in Table 10 were synthesized analogous to Compound 59 by reacting Compound 59F with corresponding carboxylic acids.

TABLE 10

| Ex. No. | Structure | Name | [M + H]$^+$ | Ret Time (min) | HPLC Methods |
|---|---|---|---|---|---|
| 60 | 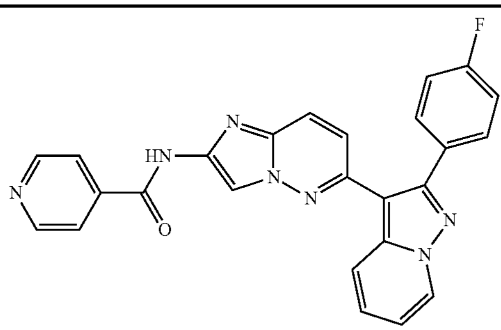 | N-(6-(2-(4-Fluorophenyl)pyrazolo[1,5-a]pyridin-3-yl)imidazo[1,2-b]pyridazin-2-yl)isonicotinamide | 450 | 7.95<br>7.87 | A<br>B |
| 61 | 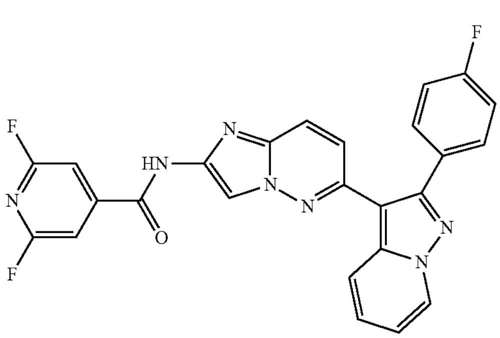 [SMILES: O=C(Nc1cn2nc(-c3c(-c4ccc(F)cc4)nn4ccccc34)ccc2n1)c1cc(F)nc(F)c1] | 2,6-Difluoro-N-(6-(2-(4-fluorophenyl)pyrazolo[1,5-a]pyridin-3-yl)imidazo[1,2-b]pyridazin-2-yl)isonicotinamide | 486 | 16.74<br>15.29 | E<br>F |

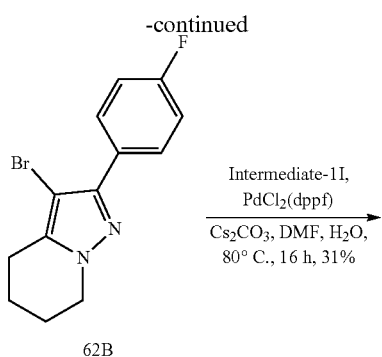

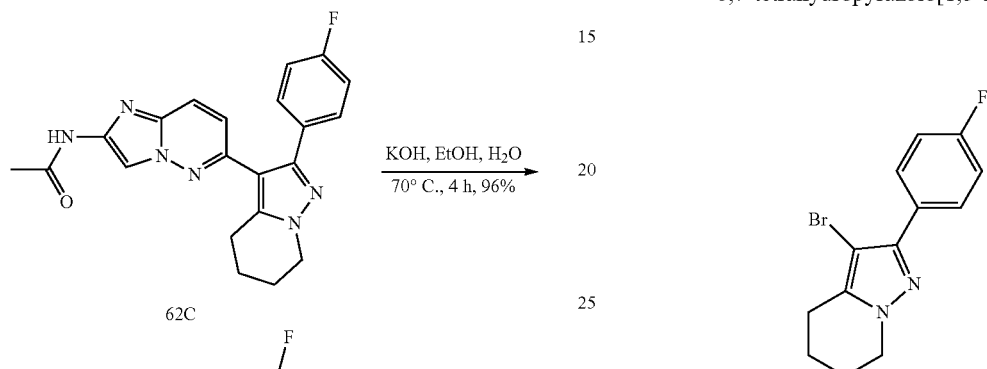

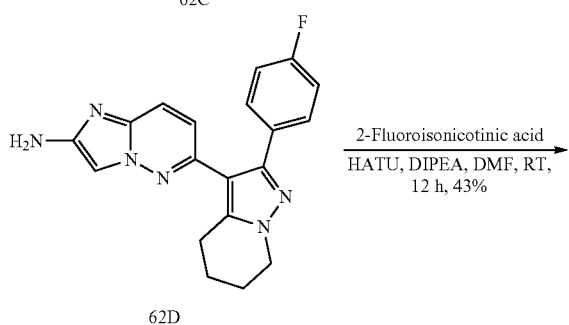

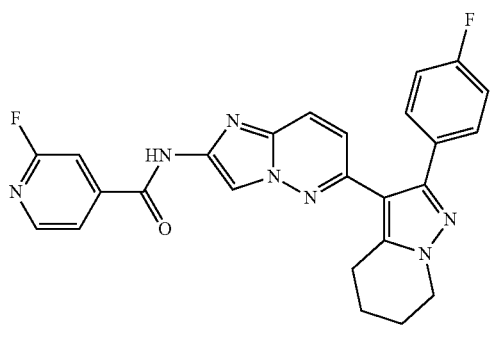

Intermediate 62A: 2-(4-Fluorophenyl)-4,5,6,7-tetra-hydropyrazolo[1,5-a]pyridine

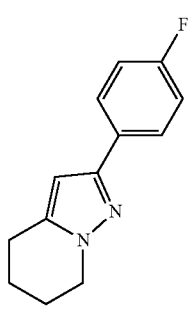 [SMILES: Fc1ccc(-c2cc3n(n2)CCCC3)cc1]

To a solution of Intermediate 59D (0.8 g, 2.75 mmol) in ethanol (15 mL) in an autoclave was added 10% Pd/C (0.292 g, 0.275 mmol) and stirred at RT under 5 Kg/cm² pressure for 48 h. The reaction mixture was filtered through CELITE®, washed with methanol and concentrated under reduced pressure to afford Intermediate 62A (0.55 g, 93%) as a white solid. MS(ES): m/z=217 [M+H]$^+$; $^1$H NMR (400 MHz, chloroform-d) δ ppm 7.82-7.91 (m, 2H), 7.06-7.15 (m, 2H), 6.47 (s, 1H), 4.16 (t, J=6.09 Hz, 2H), 2.74 (t, J=6.43 Hz, 2H), 2.03-2.12 (m, 2H), 1.88-1.96 (m, 2H).

Intermediate 62B: 3-Bromo-2-(4-fluorophenyl)-4,5,6,7-tetrahydropyrazolo[1,5-a]pyridine To a solution of Intermediate 62A (0.65 g, 3.01 mmol) in DCM (10 mL) was added NBS (0.535 g, 3.01 mmol) and stirred at RT for 2 h. The reaction mixture was diluted with water and the organic layer was extracted with DCM (3×100 mL). The combined organic layer was washed with water, brine, dried over sodium sulfate and concentrated under reduced pressure to afford desired product. The residue was purified by silica gel chromatography (40 g REDISEP® column, eluting with 15% EtOAc in hexane). The collected fractions were concentrated together to afford Intermediate 62B (0.65 g, 73%) as a yellow solid. MS(ES): m/z=297 [M+H]$^+$; $^1$H NMR (400 MHz, chloroform-d) δ ppm 7.82-7.91 (m, 2H), 7.06-7.15 (m, 2H), 4.16 (t, J=6.09 Hz, 2H), 2.74 (t, J=6.43 Hz, 2H), 2.03-2.12 (m, 2H), 1.88-1.96 (m, 2H).

Intermediate 62C: N-(6-(2-(4-Fluorophenyl)-4,5,6,7-tetrahydropyrazolo[1,5-a]pyridin-3-yl)imidazo[1,2-b]pyridazin-2-yl)acetamide To a degassed solution of Intermediate 62B (0.12 g, 0.407 mmol), Intermediate 1I (0.307 g, 1.016 mmol) and cesium carbonate (0.397 g, 1.220 mmol) in DMF (2 mL) and water (0.2 mL) was added PdCl$_2$(dppf)-CH$_2$Cl$_2$ adduct (0.017 g, 0.020 mmol). The reaction mixture was degassed with nitrogen for 10 min. and stirred at 80° C. for 16 h. The reaction mixture was diluted with water and extracted with EtOAc (3×10 mL). The combined organic layer was washed with water, brine, dried over Na$_2$SO$_4$, filtered and concentrated. The residue was purified by silica gel chromatography (12 g REDISEP® column, eluting with 2% methanol in chloroform). The collected fractions were concentrated together to afford Intermediate 62C (0.05 g, 31%) as an off-white solid. MS(ES): m/z=391 [M+H]$^+$; $^1$H NMR (400 MHz, chloroform-d) δ ppm 8.38 (s, 1H), 7.50-7.56 (m, 1H), 7.42-7.48 (m, 2H), 7.00-7.08 (m, 2H), 6.73 (d, J=9.41 Hz, 1H), 4.25 (t, J=6.12 Hz, 2H), 3.05 (t, J=6.40 Hz, 2H), 2.25 (s, 3H), 2.10-2.17 (m, 2H), 1.90-2.00 (m, 2H).

Intermediate 62D: 6-(2-(4-Fluorophenyl)-4,5,6,7-tetrahydropyrazolo[1,5-a]pyridin-3-yl)imidazo[1,2-b]pyridazin-2-amine

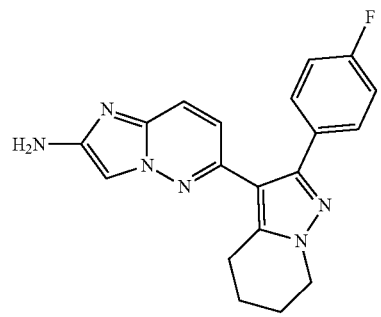 [SMILES: Nc1cn2nc(-c3c(-c4ccc(F)cc4)nn4c3CCCC4)ccc2n1]

To a solution of Intermediate 62C (0.035 g, 0.090 mmol) in EtOH (1 mL) was added KOH (0.025 g, 0.448 mmol) in water (0.5 mL) and the reaction was stirred at 70° C. for 4 h. Ethanol was removed under reduced pressure and the residue was reconstituted in ethyl acetate and water. The organics were extracted with EtOAc (3×10 mL) and the combined organic layer was washed with water, brine, dried over sodium sulfate and concentrated under reduced pressure to afford Intermediate 62D (0.03 g, 96%) as an off-white solid. MS(ES): m/z=349 [M+H]$^+$. This compound was taken for the next step without further purification.

Compound 62: 2-Fluoro-N-(6-(2-(4-fluorophenyl)-4,5,6,7-tetrahydropyrazolo[1,5-a]pyridin-3-yl)imidazo[1,2-b]pyridazin-2-yl)isonicotinamide

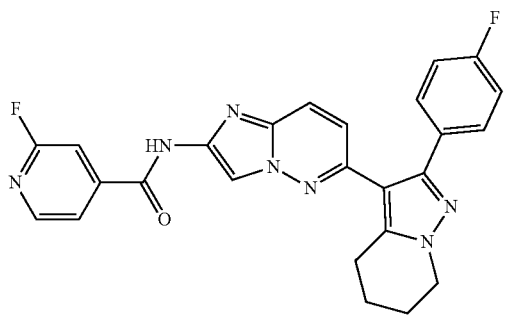 [SMILES: O=C(Nc1cn2nc(-c3c(-c4ccc(F)cc4)nn4c3CCCC4)ccc2n1)c1ccnc(F)c1]

To a solution of Intermediate 62D (0.022 g, 0.063 mmol), HATU (0.048 g, 0.126 mmol) and DIPEA (0.033 mL, 0.189 mmol) in dry DMF (0.8 mL) was added 2-fluoroisonicotinic acid (0.018 g, 0.126 mmol) and the reaction was stirred at RT for 16 h. DMF was removed under high vacuum and the residue was quenched with 10% sodium bicarbonate solution and extracted with DCM (3×30 mL). The combined organic layer was washed with sodium bicarbonate solution, water, and brine, dried over sodium sulfate and concentrated to give the crude product, which was purified by preparative HPLC to afford Compound 62 (0.013 g, 43%) as a white solid. MS(ES): m/z=472 [M+H]$^+$; HPLC Ret. Time 10.64 min and 9.71 min (HPLC Methods A and B, respectively); $^1$H NMR (400 MHz, DMSO-d$_6$) δ ppm 11.83 (s, 1H), 8.43-8.48 (m, 2H), 7.94 (dd, J=9.41, 0.56 Hz, 2H), 7.80 (s, 1H), 7.49 (dd, J=8.91, 5.52 Hz, 2H), 7.21 (t, J=8.97 Hz, 2H), 6.91 (d, J=9.41 Hz, 1H), 4.20 (t, J=6.02 Hz, 2H), 2.96 (t, J=6.27 Hz, 2H), 2.07 (dd, J=6.24, 3.61 Hz, 2H), 1.88 (d, J=5.71 Hz, 2H).

The Compounds described in Table 11 were synthesized analogous to Compound 62 by reacting Compound 62D with corresponding carboxylic acids.

TABLE 11

| Ex. No. | Structure | Name | [M + H]$^+$ | Ret Time (min) | HPLC Methods |
|---|---|---|---|---|---|
| 63 | 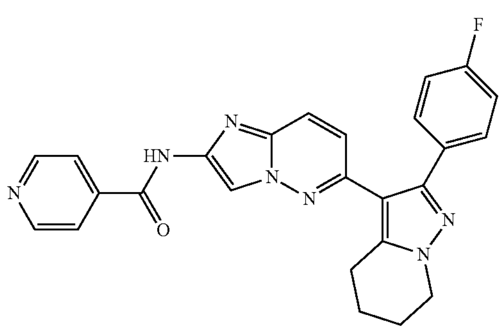 [SMILES: O=C(Nc1cn2nc(-c3c(-c4ccc(F)cc4)nn4c3CCCC4)ccc2n1)c1ccncc1] | N-(6-(2-(4-Fluorophenyl)-4,5,6,7-tetrahydropyrazolo[1,5-a]pyridin-3-yl)imidazo[1,2-b]pyridazin-2-yl)isonicotinamide | 454 | 7.63<br>7.95 | A<br>B |

TABLE 11-continued
| Ex. No. | Structure | Name | [M + H]+ | Ret Time (min) | HPLC Methods |
|---|---|---|---|---|---|
| 64 | 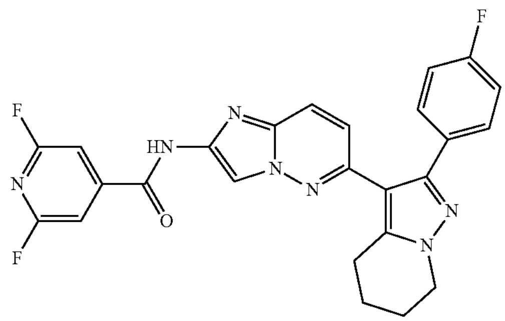 [SMILES: O=C(Nc1cn2nc(-c3c(-c4ccc(F)cc4)nn4c3CCCC4)ccc2n1)c1cc(F)nc(F)c1] | 2,6-Difluoro-N-(6-(2-(4-fluorophenyl)-4,5,6,7-tetrahydropyrazolo[1,5-a]pyridin-3-yl)imidazo[1,2-b]pyridazin-2-yl)isonicotinamide | 490 | 11.68<br>10.58 | A<br>B |
Scheme 5
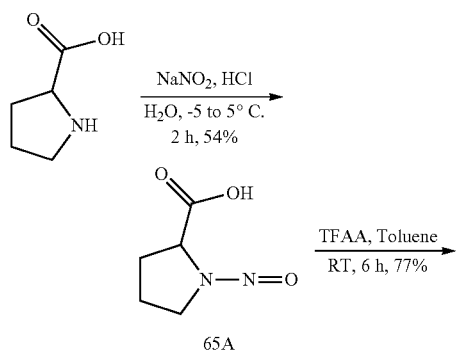
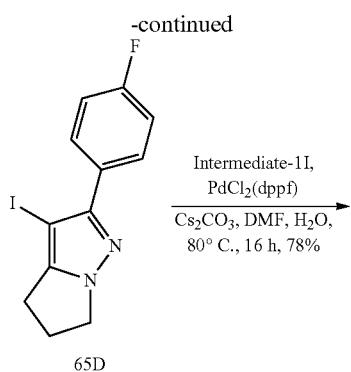
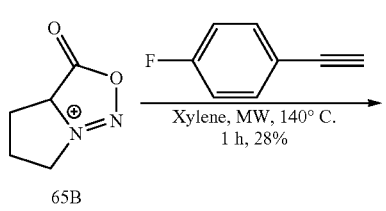
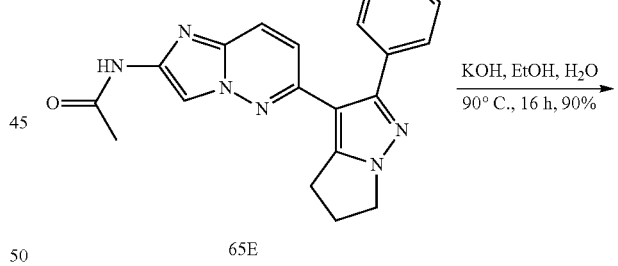
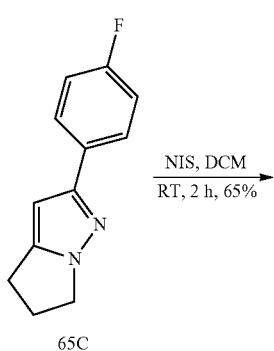
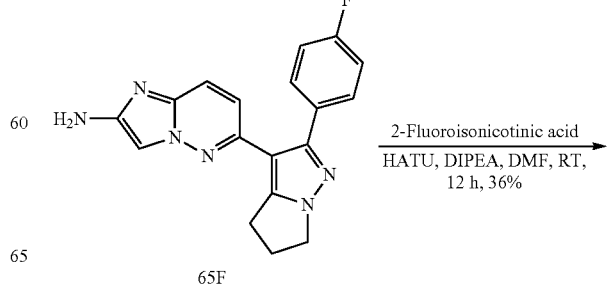

-continued

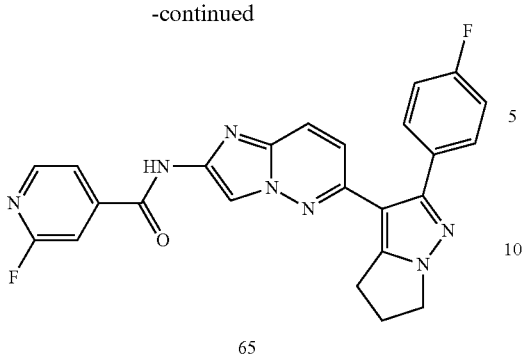

65

Intermediate 65A: 1-Nitrosopyrrolidine-2-carboxylic acid

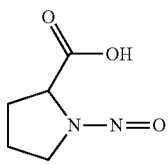

To the stirred solution of pyrrolidine-2-carboxylic acid (10 g, 87 mmol) in HCl (6.6 ml, 217 mmol) and water (34 mL) at −5° C. was added sodium nitrite (8.2 g, 119 mmol) in water (10 mL) and stirring was continued for 1.5 h at 5° C. The reaction mixture was extracted with ethyl acetate (5×100 mL) and the combined organic layer was washed with water, brine, dried over sodium sulfate and concentrated. The crude product recrystallized from benzene (20 mL) to afford pure Intermediate 65A (6.8 g, 54%) as brown solid. MS(ES): m/z=145 [M+H]$^+$. $^1$H NMR (400 MHz, chloroform-d) δ ppm 6.56-7.2 (br, m, 1H), 5.33 (dd, J=8.03, 3.51 Hz, 1H), 4.22-4.61 (m, 2H), 3.62-3.74 (m, 1H), 2.06-2.42 (m, 4H).

Intermediate 65B: 3-Oxo-3a,4,5,6-tetrahydro-3H-pyrrolo[1,2-c][1,2,3]oxadiazol-7-ium

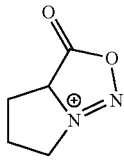

To the stirred suspension of 65A (2.5 g, 17.35 mmol) in toluene (20.0 mL) was added TFAA (2.450 mL, 17.35 mmol) and further stirred at RT for 6 h. The reaction mixture was poured into saturated sodium bicarbonate solution (20 mL) and extracted with ethyl acetate (3×50 mL). The combined organic layer was washed with water, brine, dried over sodium sulfate, filtered and concentrated under reduced pressure to afford Intermediate 65B (1.7 g, 77%) as brown liquid. $^1$H NMR (400 MHz, chloroform-d) δ ppm 4.15-4.55 (m, 2H), 2.84-2.99 (m, 2H), 2.64-2.77 (m, 2H).

Intermediate 65C: 2-(4-Fluorophenyl)-5,6-dihydro-4H-pyrrolo[1,2-b]pyrazole

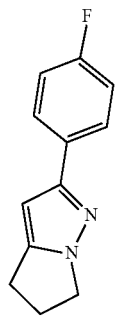 [SMILES: Fc1ccc(-c2cc3n(n2)CCC3)cc1]

To a solution of 1-ethynyl-4-fluorobenzene (1.2 g, 9.99 mmol) in xylene (4.0 mL) was added 65B (1.27 g, 9.99 mmol) in a microwave vial and stirred at 140° C. for 1 h under microwave irradiation using CEM microwave synthesizer. The reaction mixture was diluted with ethyl acetate, washed with water, brine, dried over sodium sulfate, filtered and concentrated under reduced pressure. The crude compound was purified by silica gel chromatography (40 g REDISEP® column, eluting with 30% EtOAc in hexane). The collected fractions were concentrated together to afford Intermediate 65C (0.56 g, 28%) as a brown solid. MS(ES): m/z=203 [M+H]$^+$; $^1$H NMR (400 MHz, DMSO-d$_6$) δ ppm 7.69-7.90 (m, 2H), 7.08-7.33 (m, 2H), 6.43 (s, 1H), 3.91-4.25 (m, 2H), 2.86 (t, J=7.28 Hz, 2H), 2.58 (s, 2H).

Intermediate 65D: 2-(4-Fluorophenyl)-3-iodo-5,6-dihydro-4H-pyrrolo[1,2-b]pyrazole

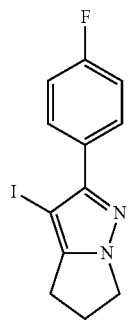 [SMILES: Fc1ccc(-c2nn3c(c2I)CCC3)cc1]

To the stirred solution of 65C (0.3 g, 1.483 mmol) in dichloromethane (10 mL) was added NIS (0.401 g, 1.780 mmol) and stirred at RT for 2 h. The reaction mixture was diluted with dichloromethane, washed with sodium thiosulfate solution, brine, dried over sodium sulfate, filtered and concentrated under reduced pressure. The crude compound was purified by silica gel chromatography (12 g REDISEP® column, eluting with 1% methanol in chloroform). Collected fractions were concentrated together to afford Intermediate 65D (0.32 g, 65%) as off-white solid. MS(ES): m/z=329 [M+H]$^+$; $^1$H NMR (400 MHz, DMSO-d$_6$) δ ppm 7.68-7.83 (m, 2H), 7.18-7.35 (m, 2H), 4.14-4.30 (m, 2H), 2.79-2.89 (m, 2H), 2.54-2.63 (m, 2H).

Intermediate 65E: N-(6-(2-(4-Fluorophenyl)-5,6-dihydro-4H-pyrrolo[1,2-b]pyrazol-3-yl)imidazo[1,2-b]pyridazin-2-yl)acetamide

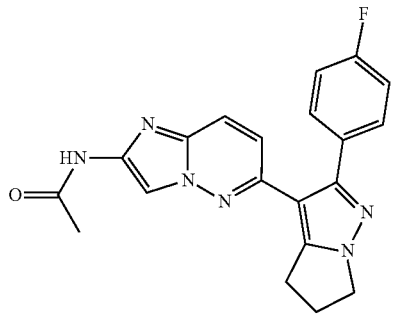 [SMILES: CC(=O)Nc1cn2nc(-c3c(-c4ccc(F)cc4)nn4c3CCC4)ccc2n1]

To a degassed solution of 65D (0.3 g, 0.914 mmol), Intermediate 1I (0.69 g, 2.286 mmol), and cesium carbonate (0.75 g, 2.286 mmol) in DMF (3.0 mL) and water (1 mL) was added $PdCl_2$(dppf)-$CH_2Cl_2$ adduct (0.045 g, 0.055 mmol). The reaction mixture was degassed with nitrogen gas for 10 minutes and stirred at 80° C. for 16 h. The reaction mixture was diluted with water, filtered through CELITE® and the aqueous layer was extracted with EtOAc (3×10 mL). The combined organic layer was washed with water, brine, dried over $Na_2SO_4$, filtered and concentrated. The residue was purified by silica gel chromatography (24 g REDISEP® column, eluting with 2% MeOH in chloroform) to afford pure Intermediate 65E (0.27 g, 78%) as off-white solid. MS(ES): m/z=377 [M+H]$^+$. $^1$H NMR (400 MHz, DMSO-$d_6$) δ ppm 10.83 (s, 1H), 8.11 (s, 1H), 7.86 (s, 1H), 7.46-7.56 (m, 2H), 7.14-7.28 (m, 2H), 6.92 (d, J=9.04 Hz, 1H), 4.21 (t, J=7.28 Hz, 2H), 3.11 (t, J=7.53 Hz, 2H), 2.56-2.69 (m, 2H), 2.01-2.14 (m, 3H).

Intermediate 65F: 6-(2-(4-Fluorophenyl)-5,6-dihydro-4H-pyrrolo[1,2-b]pyrazol-3-yl)imidazo[1,2-b]pyridazin-2-amine

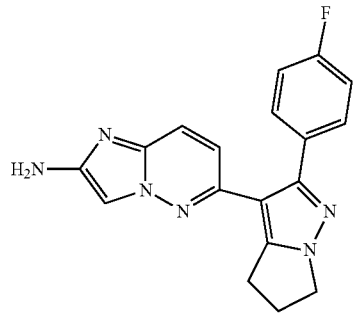 [SMILES: Nc1cn2nc(-c3c(-c4ccc(F)cc4)nn4c3CCC4)ccc2n1]

To the stirred solution of 65E (0.03 g, 0.080 mmol) in ethanol (2.0 mL) was added KOH (4.47 mg, 0.080 mmol) in water (1.0 mL) and stirred at 90° C. for 16 h. The reaction mixture was diluted dichloromethane, washed with water, brine, dried over sodium sulfate, filtered and concentrated to afford Intermediate 65F (0.024 g, 90%) as a pale yellow solid. MS(ES): m/z=335 [M+H]$^+$; $^1$H NMR (300 MHz, DMSO-$d_6$) δ ppm 7.42-7.64 (m, 3H), 7.02-7.27 (m, 3H), 6.72 (d, J=9.07 Hz, 1H), 5.39 (s, 2H), 4.19 (t, J=7.37 Hz, 2H), 3.05 (t, J=7.18 Hz, 2H), 2.58-2.73 (m, 2H).

Compound 65: 2-Fluoro-N-(6-(2-(4-fluorophenyl)-5,6-dihydro-4H-pyrrolo[1,2-b]pyrazol-3-yl)imidazo[1,2-b]pyridazin-2-yl)isonicotinamide

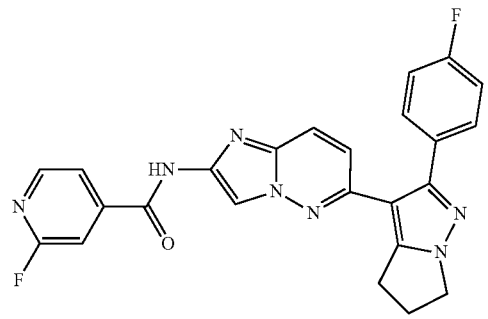 [SMILES: O=C(Nc1cn2nc(-c3c(-c4ccc(F)cc4)nn4c3CCC4)ccc2n1)c1ccnc(F)c1]

To a solution of Intermediate 65F (0.024 g, 0.072 mmol) in dry DMF (1 mL) was added HATU (0.055 g, 0.144 mmol), DIPEA (0.05 mL, 0.287 mmol), 2-fluoroisonicotinic acid (0.02 g, 0.144 mmol) and the reaction mixture was stirred at RT for 16 h. DMF was removed under high vacuum and the residue was diluted with 10% sodium bicarbonate solution and extracted with ethyl acetate (3×10 mL). The combined organic layer was washed with water, brine, dried over sodium sulfate, filtered and concentrated. The crude product was purified by preparative HPLC to afford 65 (0.012 g, 36%) as an off-white solid. MS(ES): m/z=458 [M+H]$^+$; HPLC Ret. Time min 15.82 and min 14.16 (Methods E and F, respectively); $^1$H NMR (400 MHz, DMSO-$d_6$) δ ppm 11.81 (br. s., 1H), 8.47 (s, 1H), 8.37 (s, 1H), 7.93-7.97 (m, 2H), 7.79 (s, 1H), 7.47-7.59 (m, 2H), 7.18-7.28 (m, 2H), 7.01 (d, J=9.54 Hz, 1H), 4.23 (t, J=7.28 Hz, 2H), 3.09-3.18 (m, 2H), 2.59-2.72 (m, 2H).

The Compounds described in Table 12 were synthesized analogous to Compound 65 by reacting Compound 65F with corresponding carboxylic acids.

TABLE 12

| Ex. No. | Structure | Name | [M + H]$^+$ | Ret Time (min) | HPLC Methods |
|---|---|---|---|---|---|
| 66 | ![structure] | 2,6-Difluoro-N-(6-(2-(4-fluorophenyl)-5,6-dihydro-4H-pyrrolo[1,2-b]pyrazol-3-yl)imidazo[1,2-b]pyridazin-2-yl)isonicotinamide | 476 | 11.22 11.85 | A B |

TABLE 12-continued
| Ex. No. | Structure | Name | [M + H]+ | Ret Time (min) | HPLC Methods |
|---|---|---|---|---|---|
| 67 | 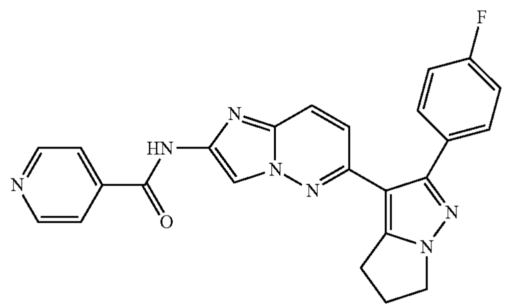 [SMILES: O=C(Nc1cn2nc(-c3c(-c4ccc(F)cc4)nn4c3CCC4)ccc2n1)c1ccncc1] | N-(6-(2-(4-Fluorophenyl)-5,6-dihydro-4H-pyrrolo[1,2-b]pyrazol-3-yl)imidazo[1,2-b]pyridazin-2-yl)isonicotinamide | 440 | 6.95<br>8.73 | A<br>B |
| 68 | 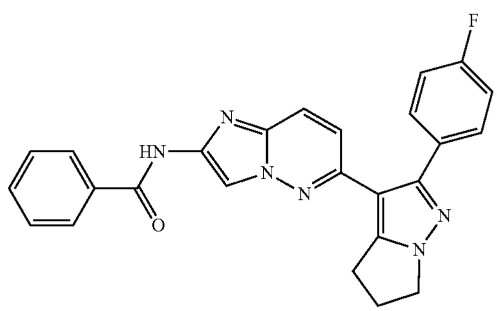 [SMILES: O=C(Nc1cn2nc(-c3c(-c4ccc(F)cc4)nn4c3CCC4)ccc2n1)c1ccccc1] | N-(6-(2-(4-Fluorophenyl)-5,6-dihydro-4H-pyrrolo[1,2-b]pyrazol-3-yl)imidazo[1,2-b]pyridazin-2-yl)benzamide | 439 | 10.43<br>11.29 | A<br>B |
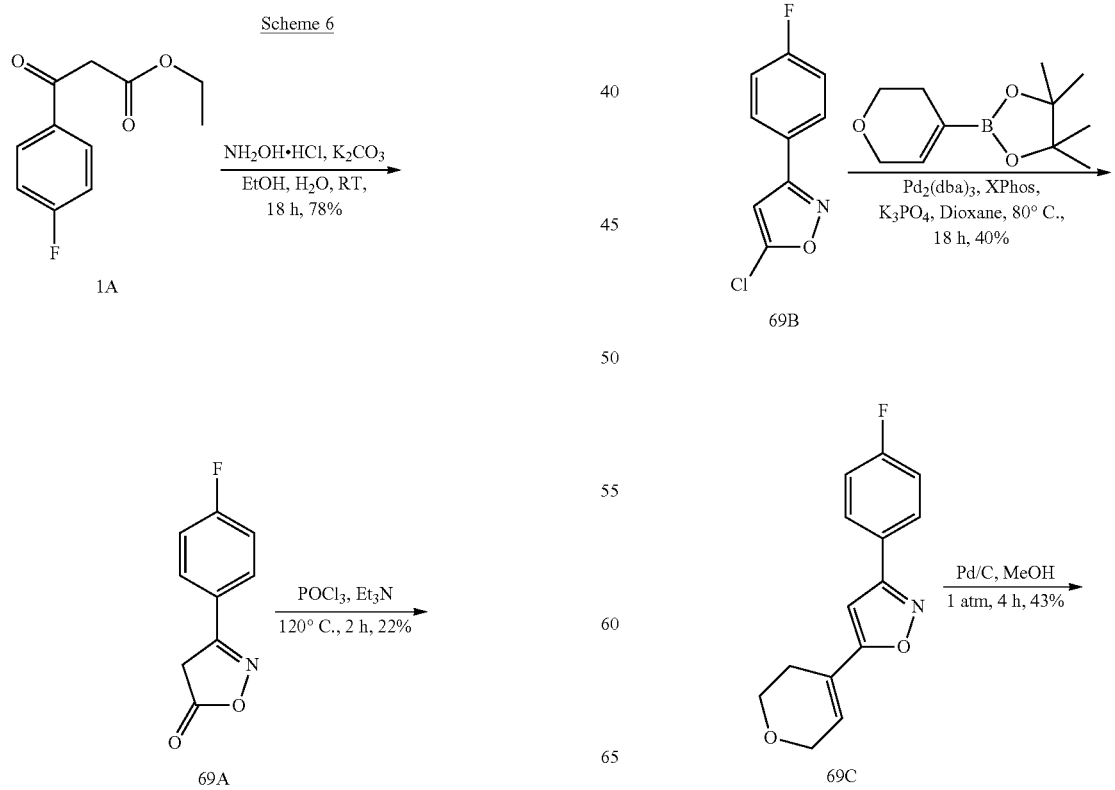

-continued

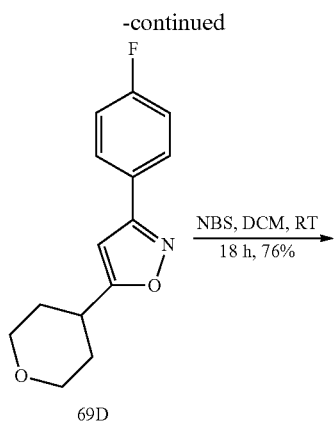

69D

NBS, DCM, RT
18 h, 76%

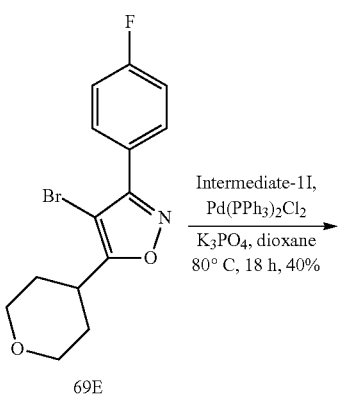

69E

Intermediate-1I,
Pd(PPh₃)₂Cl₂
K₃PO₄, dioxane
80° C, 18 h, 40%

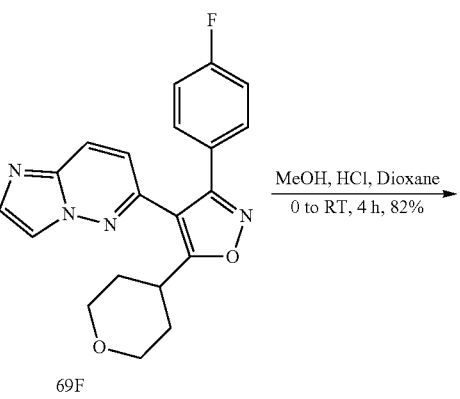

69F

MeOH, HCl, Dioxane
0 to RT, 4 h, 82%

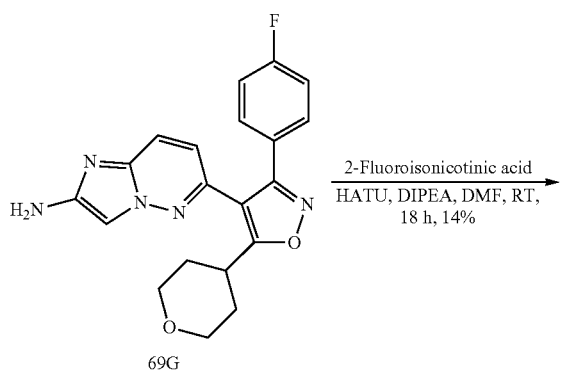

69G

2-Fluoroisonicotinic acid
HATU, DIPEA, DMF, RT,
18 h, 14%

-continued

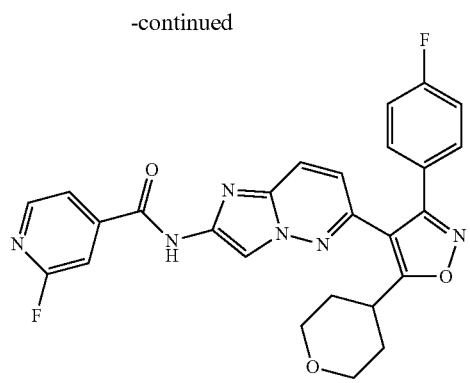

69

Intermediate 69A:
3-(4-Fluorophenyl)isoxazol-5(4H)-one

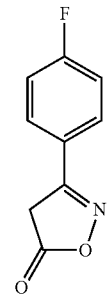 [SMILES: O=C1CC(c2ccc(F)cc2)=NO1]

To a stirred solution of Intermediate 1A (12 g, 57.1 mmol) and hydroxylamine hydrochloride (4.36 g, 62.8 mmol) in ethanol (100 mL) and water (100 mL) was added K₂CO₃ (3.94 g, 28.5 mmol) and stirred at room temperature for 18 h. Ethanol was removed under reduced pressure the yellow solid separated was filtered and dried to afford Intermediate 69A (8 g, 78%). This was used to the next step without further purification. MS(ES): m/z=178 [M−H]⁺; ¹H NMR (400 MHz, chloroform-d) δ ppm 7.65-7.77 (m, 2H), 7.11-7.23 (m, 2H), 3.79 (s, 2H).

Intermediate 69B:
5-Chloro-3-(4-fluorophenyl)isoxazole

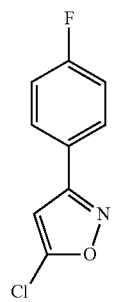 [SMILES: Fc1ccc(-c2cc(Cl)on2)cc1]

To a solution of Intermediate 69A (6.0 g, 33.5 mmol) in POCl₃ (18.73 ml, 201 mmol) was added TEA (5.13 ml, 36.8 mmol) and the reaction mixture was stirred at 120° C. for 2 h. Excess POCl₃ was removed under reduced pressure and the residue was quenched with ice. The aqueous layer was extracted with Et₂O (3×50 mL). The ether layer was washed with 10% NaHCO₃, brine, dried over Na₂SO₄, filtered and concentrated to afford crude product as a brown solid. The residue was further purified by silica gel chromatography (120 g REDISEP® column, eluting with 10% EtOAc in hexane). The collected fractions were concentrated together to afford Intermediate 69B (1.5 g, 22%) as a pale yellow solid. ¹H NMR (400 MHz, chloroform-d) δ ppm 7.70-7.80 (m, 2H), 7.11-7.21 (m, 2H), 6.45 (s, 1H).

Intermediate 69C: 5-(3,6-Dihydro-2H-pyran-4-yl)-3-(4-fluorophenyl)isoxazole

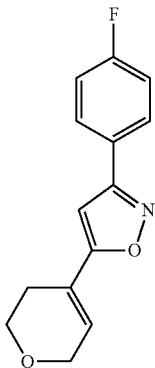 [SMILES: Fc1ccc(-c2cc(C3=CCOCC3)on2)cc1]

A white suspension of Intermediate 69B (200 mg, 1.012 mmol), 2-(3,6-dihydro-2H-pyran-4-yl)-4,4,5,5-tetramethyl-1,3,2-dioxaborolane (319 mg, 1.518 mmol)), Pd₂(dba)₃ (93 mg, 0.101 mmol), XPhos (97 mg, 0.202 mmol) and K₃PO₄ (1.518 mL, 3.04 mmol) in 1,4-dioxane (5 mL) was purged with nitrogen for 10 min. and stirred at 80° C. for 18 h. The reaction mixture was cooled to RT, filtered through CELITE® and the filtrate was concentrated under a reduced pressure. The residue obtained was diluted with water, extracted with EtOAc (3×10 mL). The combined organic layer was washed with brine, dried over Na₂SO₄, filtered and concentrated to give crude compound as yellow solid. The residue was purified silica gel chromatography (120 g REDISEP® column, eluting with 20% EtOAc in hexane). The collected fractions were concentrated together to afford Intermediate 69C (0.1 g, 40%) as yellow solid. ¹H NMR (400 MHz, chloroform-d) δ ppm 7.75-7.86 (m, 2H), 7.12-7.18 (m, 2H), 6.61 (tt, J=3.01, 1.63 Hz, 1H), 6.40 (s, 1H), 3.94 (t, J=5.40 Hz, 2H), 3.84 (t, J=5.52 Hz, 2H), 2.52 (dtt, J=5.52, 2.76, 2.76, 1.38, 1.38 Hz, 2H).

Intermediate 69D: 3-(4-Fluorophenyl)-5-(tetrahydro-2H-pyran-4-yl)isoxazole

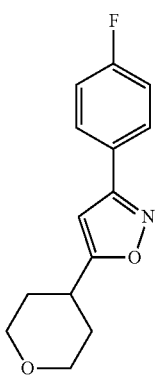 [SMILES: Fc1ccc(-c2cc(C3CCOCC3)on2)cc1]

A degassed solution of Intermediate 69C (0.08 g, 0.326 mmol) in MeOH (4 mL) was added 10% Pd/C (0.069 g, 0.065 mmol) and hydrogenated at room temperature for 4 h under one atmosphere hydrogen pressure. The reaction mixture was filtered through CELITE® and the filtrate was concentrated to afford crude product as an off-white solid. The residue was purified by silica gel chromatography (12 g REDISEP® column, eluting with 20% EtOAc in hexane). The collected fractions were concentrated together to afford Intermediate 69D (0.035 g, 43%) as white solid. MS(ES): m/z=248 [M–H]⁺; ¹H NMR (400 MHz, chloroform-d) δ ppm 7.80-7.88 (m, 2H), 7.14-7.21 (m, 2H), 6.26 (s, 1H), 4.10 (ddd, J=11.70, 4.24, 2.20 Hz, 2H), 3.56 (td, J=11.80, 2.26 Hz, 2H), 3.23 (tt, J=11.78, 3.94 Hz, 1H), 2.02-2.15 (m, 2H), 1.82-1.90 (m, 2H).

Intermediate 69E: 4-Bromo-3-(4-fluorophenyl)-5-(tetrahydro-2H-pyran-4-yl)isoxazole

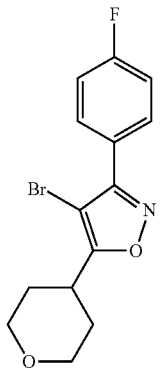 [SMILES: Fc1ccc(-c2noc(C3CCOCC3)c2Br)cc1]

To a solution of Intermediate 69D (250 mg, 1.011 mmol) in DCM (2 mL) was added NBS (180 mg, 1.011 mmol) and stirred at room temperature for 18 h. The reaction mixture was filtered through CELITE® and filtrate was evaporated to afford crude compound as off-white solid. The residue was purified silica gel chromatography (24 g REDISEP® column, eluting with 20% EtOAc in hexane). The collected fractions were concentrated together to afford Intermediate 69E (0.25 g, 76%) as off-white solid. MS(ES): m/z=327 [M–H]⁺; ¹H NMR (400 MHz, chloroform-d) δ ppm 7.80-7.88 (m, 2H), 7.14-7.21 (m, 2H), 4.10 (ddd, J=11.70, 4.24, 2.20 Hz, 2H), 3.56 (td, J=11.80, 2.26 Hz, 2H), 3.23 (tt, J=11.78, 3.94 Hz, 1H), 2.02-2.15 (m, 2H), 1.82-1.90 (m, 2H).

Intermediate 69F: N-(6-(3-(4-Fluorophenyl)-5-(tetrahydro-2H-pyran-4-yl)isoxazol-4-yl)imidazo[1,2-b]pyridazin-2-yl)acetamide

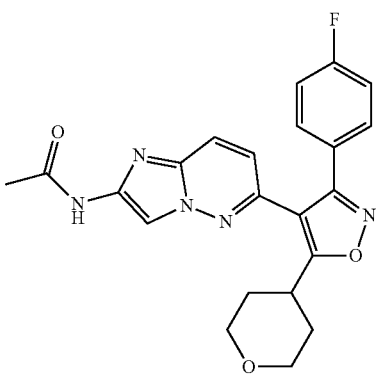 [SMILES: CC(=O)Nc1cn2nc(-c3c(-c4ccc(F)cc4)noc3C3CCOCC3)ccc2n1]

To a degassed white suspension of Intermediate 69E (0 mg, 0.552 mmol), Intermediate 1I (500 mg, 1.656 mmol) and K$_3$PO$_4$ (0.414 mL, 1.656 mmol) in 1,4-dioxane (5 mL) was added Pd(PPh$_3$)$_2$Cl$_2$ (38.7 mg, 0.055 mmol) and stirred 80° C. for 18 h. The reaction mixture was filtered through CELITE® and the filtrate was concentrated under reduced pressure. To this residue was added water and extracted with EtOAc (3×15 mL). The combined organic layer was washed with brine, dried over Na$_2$SO$_4$, filtered and concentrated to give a crude compound as a yellow solid. The crude product was further purified by silica gel chromatography (24 g REDISEP® column, eluting with 2% methanol in chloroform). The collected fractions were concentrated together to afford Intermediate 69F (0.1 g, 40%) as off-white solid. MS(ES): m/z=422 [M−H]$^+$; $^1$H NMR (400 MHz, chloroform-d) δ ppm 8.46 (s, 1H), 8.12 (br. s., 1H), 7.64 (dd, J=9.29, 0.63 Hz, 1H), 7.43-7.49 (m, 2H), 7.05-7.12 (m, 2H), 6.67 (d, J=9.29 Hz, 1H), 4.06-4.14 (m, 2H), 3.50 (td, J=11.81, 2.16 Hz, 2H), 3.36-3.44 (m, 1H), 2.27 (s, 2H), 2.10-2.16 (m, 2H), 1.89-1.95 (m, 3H).

Intermediate 69G: 6-(3-(4-Fluorophenyl)-5-(tetrahydro-2H-pyran-4-yl)isoxazol-4-yl)imidazo[1,2-b]pyridazin-2-amine

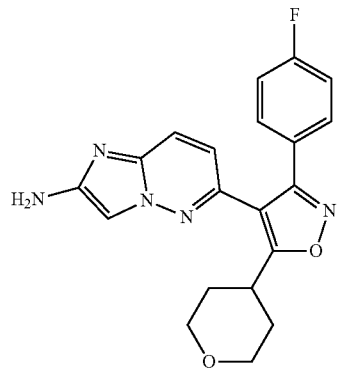 [SMILES: Nc1cn2nc(-c3c(-c4ccc(F)cc4)noc3C3CCOCC3)ccc2n1]

To a solution of Intermediate 69F (0.1 g, 0.237 mmol) in MeOH (1 mL) at 0° C. was added 4 M HCl in 1,4-dioxane (0.890 mL, 3.56 mmol) and the reaction mixture was stirred at room temperature for 4 h. The solvent was removed from the reaction mixture, 10% NaHCO$_3$ was added and the residue extracted with ethyl acetate (3×5 mL). The combined organic layer was washed with 10% NaHCO$_3$ (2×5 mL), brine, dried over Na$_2$SO$_4$, filtered and concentrated to afford crude product 69G (0.09 g, 82%) as a yellow solid, which was used to the next step without further purification. MS(ES): m/z=380[M−H]$^+$.

Intermediate 69: 2-Fluoro-N-(6-(3-(4-fluorophenyl)-5-(tetrahydro-2H-pyran-4-yl)isoxazol-4-yl)imidazo[1,2-b]pyridazin-2-yl)isonicotinamide

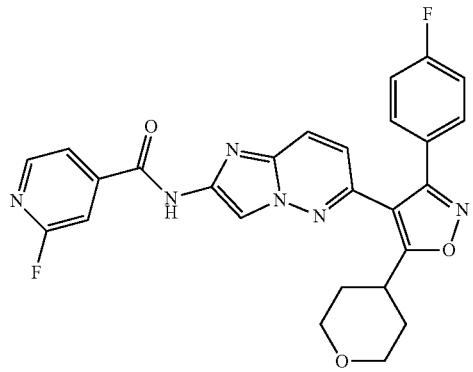 [SMILES: O=C(Nc1cn2nc(-c3c(-c4ccc(F)cc4)noc3C3CCOCC3)ccc2n1)c1ccnc(F)c1]

To a solution of 2-fluoroisonicotinic acid (23.24 mg, 0.165 mmol), HATU (62.6 mg, 0.165 mmol) and DIPEA (0.035 mL, 0.198 mmol) in DMF (2 mL) was added Intermediate 69G (25 mg, 0.066 mmol) and stirred at room temperature for 18 h. The reaction mixture was diluted with water (5 mL) and extracted with EtOAc (3×5 mL). The combined organic layer was washed with water, brine, dried over Na$_2$SO$_4$, filtered and concentrated to afford the crude product as a dark brown residue. The crude product was further purified via reverse phase HPLC to give Compound 69 (0.005 g, 14%) as an off-white solid. MS(ES): m/z=503 [M+H]$^+$; HPLC Ret. Time 17.61 min and 15.11 min. (HPLC Methods E and F, respectively); $^1$H NMR (400 MHz, DMSO-d$_6$) δ ppm 11.81 (br. s., 1H), 8.55 (s, 1H), 8.47 (d, J=5.52 Hz, 1H), 8.07 (d, J=9.54 Hz, 1H), 7.97 (dd, J=5.02, 1.51 Hz, 1H), 7.80 (s, 1H), 7.51-7.58 (m, 2H), 7.26-7.33 (m, 2H), 7.04 (d, J=9.54 Hz, 1H), 3.90-3.97 (m, 2H), 3.40-3.48 (m, 3H), 1.84-1.91 (m, 4H).

The Compounds described in Table 13 were synthesized analogous to Compound 69 by reacting Compound 69G with corresponding carboxylic acids.

TABLE 13

| Ex. No. | Structure | Name | [M + H]$^+$ | Ret Time (min) | HPLC Methods |
|---|---|---|---|---|---|
| 70 | 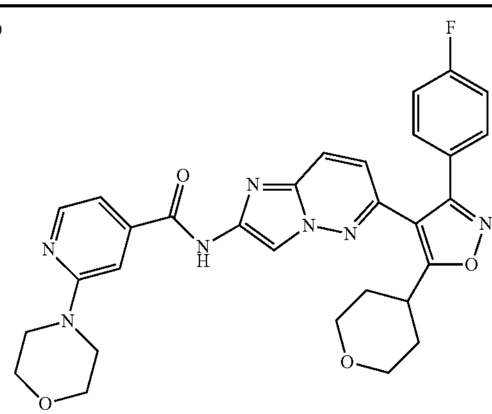 | N-(6-(3-(4-Fluorophenyl)-5-(tetrahydro-2H-pyran-4-yl)isoxazol-4-yl)imidazo[1,2-b]pyridazin-2-yl)-2-morpholinoisonicotinamide | 568[M − H] | 8.04<br>8.18 | A<br>B |

TABLE 13-continued

| Ex. No. | Structure | Name | [M + H]+ | Ret Time (min) | HPLC Methods |
|---|---|---|---|---|---|
| 71 | 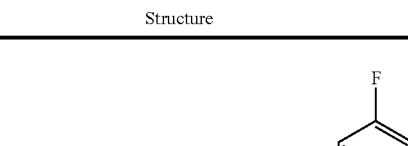 | N-(6-(3-(4-Fluorophenyl)-5-(tetrahydro-2H-pyran-4-yl)isoxazol-4-yl)imidazo[1,2-b]pyridazin-2-yl)-[2,3'-bipyridine]-4-carboxamide | 559[M − H] | 7.60 8.18 | A B |

What is claimed is:

1. A compound according to Formula (I):

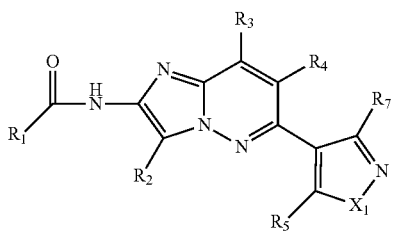

or a pharmaceutically-acceptable salt thereof, wherein:

$X_1$ is selected from O and $NR_6$; provided when $X_1$ is $NR_6$, $R_5$ and $R_6$ together with the nitrogen atom and the adjacent carbon atom to which they are respectively attached form a heterocyclic ring comprising carbon atoms and zero to 3 additional heteroatoms selected from N, $NR_8$, O, S and substituted with 1-5 $R_{10}$;

$R_1$ is selected from $C_{1-4}$alkyl (optionally substituted with F, Cl, Br, OH, CN, and $NR_aR_a$), —$(CR_dR_d)_r$-carbocyclyl substituted with 0-5 $R_{11}$, and —$(CR_dR_d)_r$-heterocyclyl comprising carbon atoms and 1 to 4 heteroatoms selected from N, $NR_9$, O, S, and substituted with 0-5 $R_{11}$;

$R_2$ is selected from H, $C_{1-4}$alkyl, F, Cl, Br, CN, aryl, and heteroaryl;

$R_3$ is selected from H and $C_{1-4}$alkyl;

$R_4$ is selected from H, $C_{1-4}$alkyl F, Cl, Br, and CN;

$R_5$ is selected from H, $C_{1-4}$alkyl substituted with 0-4 $R_e$, —$(CH_2)_r$—$C_{3-6}$ carbocyclyl substituted with 0-4 $R_e$, and —$(CH_2)_r$-heterocyclyl comprising carbon atoms and 1 to 3 heteroatoms selected from N, O, S, and substituted with 0-4 $R_e$;

$R_7$ is aryl substituted with 0-3 $R_e$;

$R_8$ is selected from H, $C_{1-4}$ alkyl substituted with 0-3 $R_e$, —$(CH_2)_rCN$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rNR_aC(=O)R_b$ with 0-3 $R_e$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_2NR_aR_a$, —$(CH_2)_rNR_aS(O)_2NR_aR_a$, —$(CH_2)_rNR_aS(O)_2R_c$, $(CH_2)_r$-carbocyclyl substituted with 0-3 $R_e$, and —$(CH_2)_r$-heterocyclyl substituted with 0-3 $R_e$;

R9 is selected from H, —$C(=O)R_b$, $C_{1-6}$ alkyl substituted with 0-5 $R_e$, —$(CH_2)_r$—$C_{3-6}$carbocyclyl substituted with 0-5 $R_e$, and —$(CH_2)_r$-heterocyclyl substituted with 0-5 $R_e$;

$R_{10}$ is selected from H, $C_{1-6}$alkyl substituted with 0-3 $R_e$, —$(CH_2)_rNR_aR_a$, —$(CH_2)_rC(=O)R_b$, —$(CH_2)_rC(=O)OR_b$, —$(CH_2)_rC(=O)NR_aR_a$, $S(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_{11}$, at each occurrence, is independently selected from H, F, Cl, Br, =O, CN, $NO_2$, —$OR_b$, —$S(O)_pR_c$, —$C(=O)R_b$, —$(CR_dR_d)_rNR_aR_a$, —$(CR_dR_d)_rC(=O)NR_aR_a$, —$NR_aC(=O)R_b$, —$NR_aC(=O)OR_b$, —$OC(=O)NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl substituted with 0-5 $R_e$, and heterocyclyl substituted with 0-5 $R_e$;

$R_d$, at each occurrence, is independently selected from H and $C_{1-4}$alkyl substituted with 0-5 $R_e$;

$R_e$, at each occurrence, is selected from $C_{1-6}$ alkyl substituted with 0-5 $R_f$, $C_{2-6}$ alkenyl, $C_{2-6}$ alkynyl, —(CH$_2$)$_r$—C$_{3-6}$ cycloalkyl, F, Cl, Br, CN, NO$_2$, =O, CO$_2$H, —(CH$_2$)$_r$OR$_f$, SR$_f$, and —(CH$_2$)$_r$NR$_f$R$_f$;

R$_f$, at each occurrence, is independently selected from H, F, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

2. The compound according to claim 1 of Formula (II):

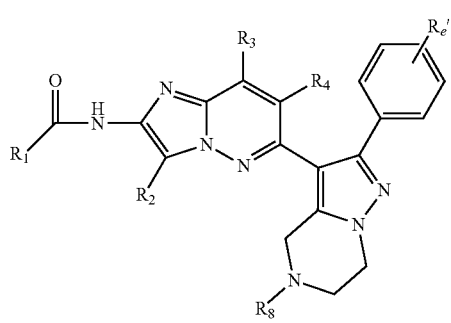

or a pharmaceutically-acceptable salt thereof, wherein:

R$_1$ is selected from aryl, cycloalkyl, and heterocyclyl selected from pyridyl, pyrimidinyl, pyrazinyl, pyridazinyl, triazinyl, furyl, quinolinyl, quinoxalinyl, dihydroquinolinyl, tetrahydroquinolinyl, tetrahydropyranyl, isoquinolinyl, thienyl, imidazolyl, thiazolyl, indolyl, pyrrolyl, oxazolyl, benzofuryl, benzothienyl, benzothiazolyl, benzoxazinyl, isoxazolyl, pyrazolyl, triazolyl, tetrazolyl, indazolyl, 1,2,3-thiadiazolyl, 1,2,4-thiadiazolyl, isothiazolyl, purinyl, carbazolyl, benzimidazolyl, indolinyl, benzodioxolanyl, benzodioxane, 1,5-naphthyridinyl, imidazopyridinyl, azetidinyl, pyrrolidinyl, piperidinyl, piperazinyl, and morpholinyl, each substituted with 0-4 R$_{11}$;

R$_2$ is selected from H, C$_{1-4}$alkyl, F, Cl, Br, CN, aryl, and heteroaryl;

R$_3$ is selected from H and C$_{1-4}$alkyl;

R$_4$ is selected from H, C$_{1-4}$alkyl F, Cl, Br, and CN;

R$_e$' is selected from F, Cl, Br, and C$_{1-6}$ alkyl substituted with 0-5 R$_f$;

R$_8$ is selected from H, C$_{1-4}$ alkyl substituted with 0-3 R$_e$, —S(O)$_p$R$_c$, —C(=O)R$_b$, —C(=O)NR$_a$R$_a$, —C(=O)(CH$_2$)$_r$NR$_a$R$_a$, —(CH$_2$)$_r$C(=O)OR$_b$, —S(O)$_2$NR$_a$R$_a$, C$_{3-6}$ carbocyclyl substituted with 0-3 R$_e$, and heterocyclyl substituted with 0-3 R$_e$; and R$_{11}$, at each occurrence, is independently selected from H, F, Cl, Br, =O, CN, NO$_2$, —OR$_b$, —S(O)$_p$R$_c$, —C(=O)R$_b$, —(CH$_2$)$_r$NR$_a$R$_a$, —(CH$_2$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CH$_2$)$_r$C(=O)OR$_b$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-heterocyclyl substituted with 0-5 R$_e$.

3. The compound according to claim 1 of Formula (III):

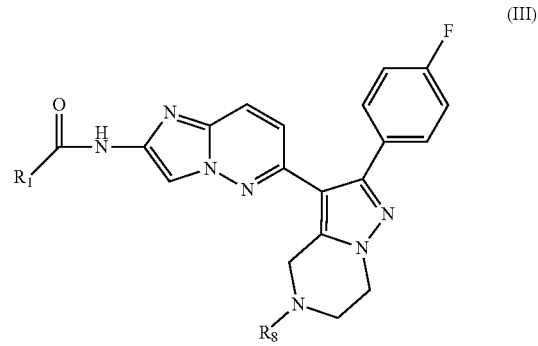

or a pharmaceutically-acceptable salt thereof, wherein:

R$_1$ is selected from

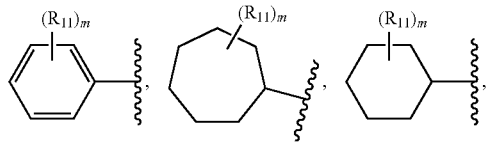
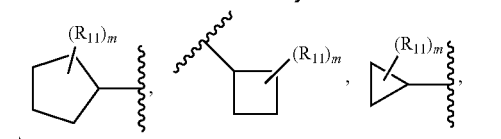
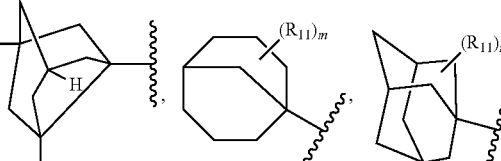
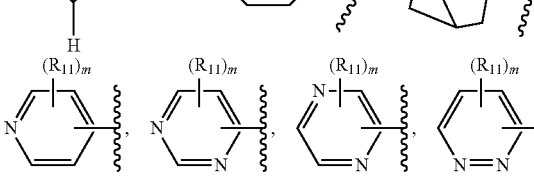
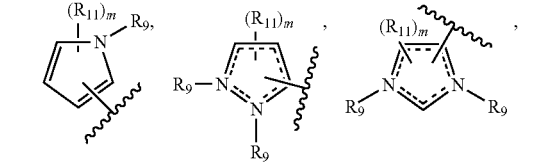
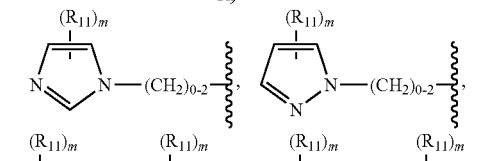
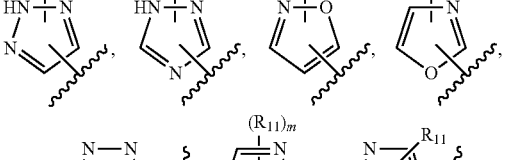

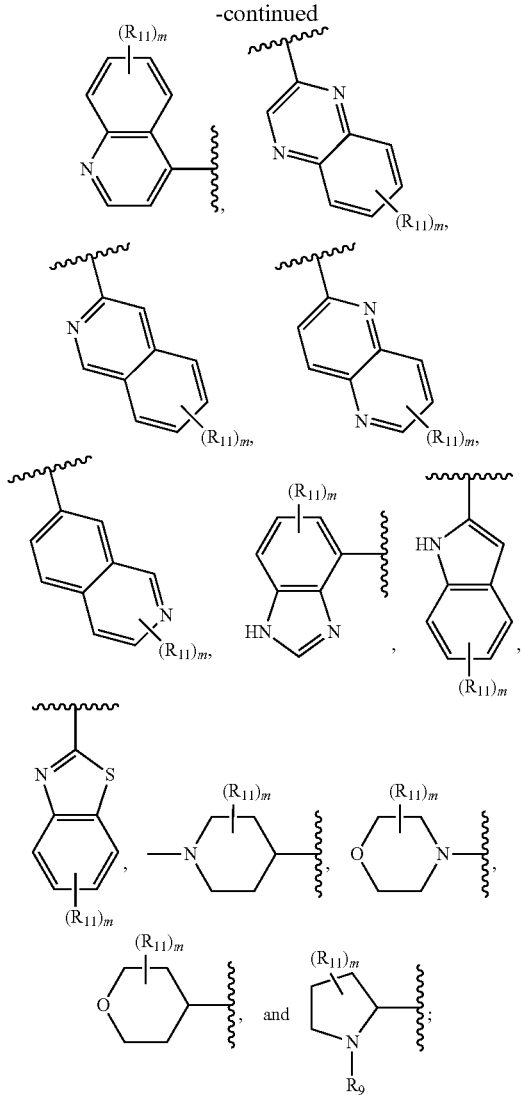

---- represents an optional bond;

R₈ is selected from H, C₁₋₄ alkyl substituted with 0-3 R$_e$, —S(O)$_p$R$_c$, —C(=O)R$_b$, —C(=O)NR$_a$R$_a$, —C(=O)(CH₂)$_r$NR$_a$R$_a$, —C(=O)OR$_b$, —S(O)₂NR$_a$R$_a$, C$_{3-6}$ carbocyclyl substituted with 0-3 R$_e$, and heterocyclyl substituted with 0-3 R$_e$;

R9, at each occurrence, is independently selected from H, —C(=O)R$_b$, and C$_{1-6}$ alkyl substituted with 0-5 R$_e$;

R₁₁, at each occurrence, is independently selected from H, F, Cl, Br, =O, CN, —OR$_b$, —C(=O)R$_b$, —(CH₂)$_r$NR$_a$R$_a$, —(CH₂)$_r$C(=O)NR$_a$R$_a$, —NR$_a$C(=O)R$_b$, —(CH₂)$_r$C(=O)OR$_b$, C$_{1-6}$ alkyl substituted with 0-5 R$_e$, —(CH₂)$_r$—C$_{3-6}$carbocyclyl substituted with 0-5 R$_e$, and —(CH₂)$_r$-heterocyclyl substituted with 0-5 R$_e$;

R$_a$, at each occurrence, is independently selected from H, C$_{1-6}$ alkyl substituted with 0-5 R$_e$, —(CH₂)$_r$—C$_{3-10}$ carbocyclyl substituted with 0-5 R$_e$, and —(CH₂)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, —(CH₂)$_r$—C$_{3-10}$ carbocyclyl substituted with 0-5 R$_e$, and —(CH₂)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl substituted with 0-5 R$_e$, and heterocyclyl substituted with 0-5 R$_e$;

R$_e$, at each occurrence, is independently selected from C$_{1-6}$ alkyl substituted with 0-5 R$_f$, —(CH₂)$_r$—C$_{3-6}$ cycloalkyl, F, Cl, Br, CN, NO₂, =O, CO₂H, —(CH₂)$_r$OC$_{1-5}$ alkyl, —(CH₂)$_r$OH, SH, and —(CH₂)$_r$NR$_f$R$_f$;

R$_f$, at each occurrence, is independently selected from H, F, C$_{1-5}$ alkyl, and phenyl, or R$_f$ and R$_f$ together with the nitrogen atom to which they are both attached form a heterocyclic ring; and m, at each occurrence, is independently selected from zero, 1, and 2.

4. The compound according to claim 3 or a pharmaceutically-acceptable salt thereof, wherein:
R₁ is selected from

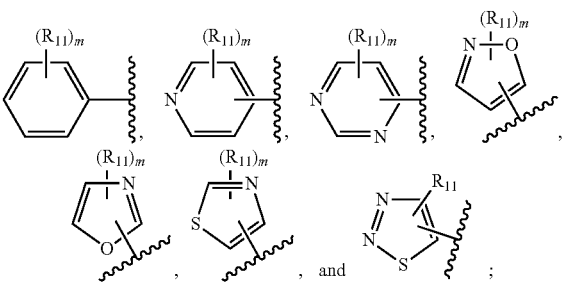

R₈ is selected from H, C$_{1-4}$alkyl substituted with 0-3 R$_e$, —C(=O)C$_{1-4}$alkyl substituted with 0-3 R$_e$, —C(=O)-aryl substituted with 0-3 R$_e$, —C(=O)-heteroaryl substituted with 0-3 R$_e$, —C(=O)CH₂CN, C$_{3-6}$ cycloalkyl, heterocyclyl substituted with 0-3 R$_e$, —C(=O)OC$_{1-4}$alkyl substituted with 0-3 R$_e$, S(O)₂—C$_{1-4}$alkyl substituted with 0-3 R$_e$, S(O)₂—C$_{3-6}$ cycloalkyl substituted with 0-3 R$_e$, S(O)₂—(CH₂)$_r$-aryl substituted with 0-3 R$_e$, S(O)₂-heteroaryl substituted with 0-3 R$_e$, C(=O)NHC$_{1-4}$alkyl substituted with 0-3 R$_e$, C(=O)NHC$_{3-6}$ cycloalkyl substituted with 0-3 R$_e$, C(=O)NH-admantanyl, C(=O)NH-aryl substituted with 0-3 R$_e$, and C(=O)NH-heteroaryl substituted with 0-3 R$_e$;

R₁₁, at each occurrence, is independently selected from H, F, —NR$_a$R$_a$, C$_{1-6}$ alkyl substituted with 0-5 R$_e$, —(CH₂)$_r$—C$_{3-6}$carbocyclyl substituted with 0-5 R$_e$, and —(CH₂)$_r$-heterocyclyl substituted with 0-5 R$_e$;

R$_a$, at each occurrence, is independently selected from H, C$_{1-6}$ alkyl substituted with 0-5 R$_e$, —(CH₂)$_r$—C$_{3-10}$ carbocyclyl substituted with 0-5 R$_e$, and —(CH₂)$_r$-heterocyclyl substituted with 0-5 R$_e$; or R$_a$ and R$_a$ together with the nitrogen atom to which they are both attached form a heterocyclic ring substituted with 0-5 R$_e$;

R$_e$, at each occurrence, is independently selected from C$_{1-6}$ alkyl substituted with 0-5 R$_f$, —(CH₂)$_r$—C$_{3-6}$ cycloalkyl, F, Cl, Br, CN, NO₂, =O, CO₂H, —(CH₂)$_r$OC$_{1-5}$alkyl, —(CH₂)$_r$OH, SH, and —(CH₂)$_r$NR$_f$R$_f$;

R$_f$, at each occurrence, is independently selected from H, F, C$_{1-5}$ alkyl; and m, at each occurrence, is independently selected from zero, 1, and 2.

5. The compound according to claim 1 of Formula (IV):

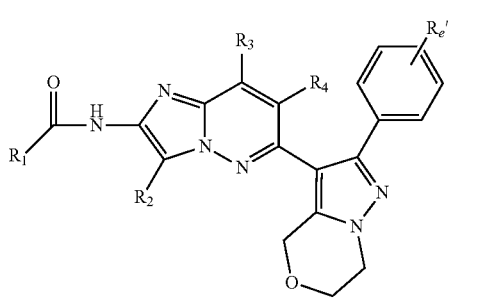

(IV)

or a pharmaceutically-acceptable salt thereof, wherein:
$R_1$ is selected from carbocyclyl substituted with 0-5 $R_{11}$ and heterocyclyl comprising carbon atoms and 1 to 4 heteroatoms selected from N, $NR_9$, O, S, and substituted with 0-5 $R_{11}$;
$R_2$ is selected from H, $C_{1-4}$alkyl, F, Cl, Br, CN, aryl, and heteroaryl;
$R_3$ is selected from H and $C_{1-4}$alkyl;
$R_4$ is selected from H, $C_{1-4}$alkyl F, Cl, Br, and CN;
$R_e'$ is selected from F, Cl, and Br;
$R_9$, at each occurrence, is independently selected from H, —C(=O)$R_b$, and $C_{1-6}$ alkyl substituted with 0-5 $R_e$;
$R_{11}$, at each occurrence, is independently selected from H, F, Cl, CN, —$OR_b$, —$(CH_2)_rNR_aR_a$, —$NR_aC(=O)R_b$, $C_{1-6}$ alkyl substituted with 0-5 $R_e$, —$(CH_2)_r$—$C_{3-6}$carbocyclyl substituted with 0-5 $R_e$, and —$(CH_2)_r$-5- to 10-membered heterocyclyl substituted with 0-5 $R_e$;
$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_e$, at each occurrence, is independently selected from $C_{1-6}$ alkyl substituted with 0-5 $R_f$, —$(CH_2)_r$—$C_{3-6}$ cycloalkyl, F, Cl, Br, CN, $NO_2$, =O, $CO_2H$, —$(CH_2)_rOC_{1-5}$alkyl, —$(CH_2)_rOH$, $S(O)_2C_{1-4}$alkyl, and —$(CH_2)_rNR_fR_f$;
$R_f$, at each occurrence, is independently selected from H, $C_{1-5}$ alkyl, and phenyl, or $R_f$ and $R_f$ together with the nitrogen atom to which they are both attached form a heterocyclic ring; and
r, at each occurrence, is independently selected from zero, 1, 2, 3, and 4.

6. The compound according to claim 5 or a pharmaceutically-acceptable salt thereof, wherein:
$R_1$ is selected from

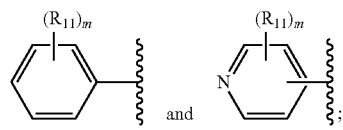

$R_{11}$, at each occurrence, is independently selected from F, Cl, —$NR_aR_a$, OH, $OC_{1-4}$alkyl, $C_{1-4}$ alkyl substituted with 0-5 $R_e$,

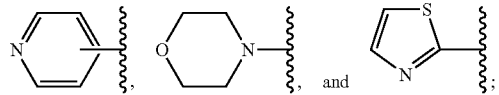

$R_a$, at each occurrence, is independently selected from H and $C_{1-4}$ alkyl substituted with 0-5 $R_e$;
$R_e$, at each occurrence, is independently selected from $C_{1-6}$ alkyl F, Cl, Br, CN, and $NH_2$; and
m, at each occurrence, is independently selected from zero, 1, and 2.

7. The compound according to claim 1 of Formula (V):

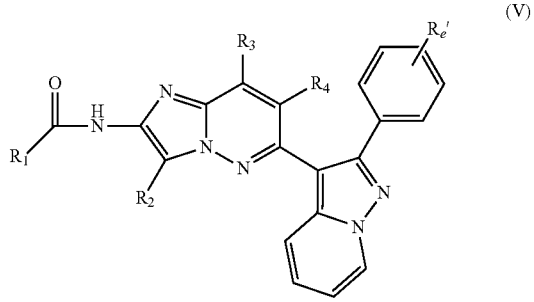

(V)

or a pharmaceutically-acceptable salt thereof, wherein:
$R_1$ is selected from carbocyclyl substituted with 0-5 $R_{11}$ and heteroaryl comprising carbon atoms and 1 to 4 heteroatoms selected from N, O, S, and substituted with 0-5 $R_{11}$;
$R_2$ is selected from H, $C_{1-4}$alkyl, F, Cl, Br, CN, aryl, and heteroaryl;
$R_3$ is selected from H and $C_{1-4}$alkyl;
$R_4$ is selected from H, $C_{1-4}$alkyl F, Cl, Br, and CN;
$R_e'$ is selected from F, Cl, and Br;
$R_{11}$, at each occurrence, is independently selected from H, F, —$NR_aR_a$, $C_{1-6}$ alkyl substituted with 0-5 $R_e$, —$(CH_2)_r$—$C_{3-6}$carbocyclyl substituted with 0-5 $R_e$, and —$(CH_2)_r$-heterocyclyl substituted with 0-5 $R_e$;
$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOR_f$, $SR_f$, and —$(CH_2)_rNR_fR_f$;
$R_f$, at each occurrence, is independently selected from H, F, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;
p, at each occurrence, is independently selected from zero, 1, and 2; and r, at each occurrence, is independently selected from zero, 1, 2, 3, and 4.

8. The compound according to claim 1 of Formula (VI):

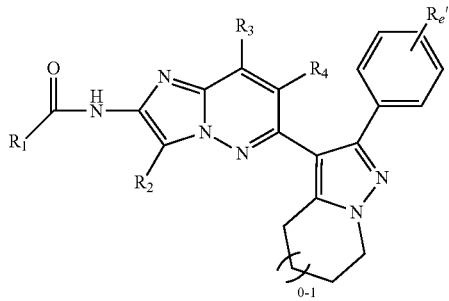

(VI)

or a pharmaceutically-acceptable salt thereof, wherein:
- $R_1$ is selected from carbocyclyl substituted with 0-5 $R_{11}$ and heterocyclyl comprising carbon atoms and 1 to 4 heteroatoms selected from N, $NR_9$, O, S, and substituted with 0-5 $R_{11}$;
- $R_2$ is selected from H, $C_{1-4}$alkyl, F, Cl, Br, CN, aryl, and heteroaryl;
- $R_3$ is selected from H and $C_{1-4}$alkyl;
- $R_4$ is selected from H, $C_{1-4}$alkyl F, Cl, Br, and CN;
- $R_e'$ is selected from F, Cl, and Br;
- $R_9$, at each occurrence, is independently selected from H, —C(=O)$R_b$, and $C_{1-6}$ alkyl substituted with 0-5 $R_e$;
- $R_{11}$, at each occurrence, is independently selected from H, F, —$NR_aR_a$, $C_{1-6}$ alkyl substituted with 0-5 $R_e$, —(CH$_2$)$_r$—$C_{3-6}$carbocyclyl substituted with 0-5 $R_e$, and —(CH$_2$)$_r$-heterocyclyl substituted with 0-5 $R_e$;
- $R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;
- $R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;
- $R_e$, at each occurrence, is independently selected from $C_{1-6}$ alkyl substituted with 0-5 $R_f$, $C_{2-6}$ alkenyl, $C_{2-6}$ alkynyl, —(CH$_2$)$_r$—$C_{3-6}$ cycloalkyl, F, Cl, Br, CN, NO$_2$, =O, $CO_2$H, —(CH$_2$)$_r$OR$_f$, SR$_f$, and —(CH$_2$)$_r$NR$_fR_f$;
- $R_f$, at each occurrence, is independently selected from H, F, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl; and
- r, at each occurrence, is independently selected from zero, 1, 2, 3, and 4.

9. The compound according to claim 1 of Formula (VII):

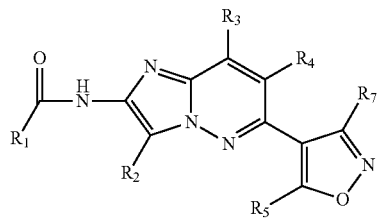

(VII)

or a pharmaceutically-acceptable salt thereof, wherein:
- $R_1$ is selected from carbocyclyl substituted with 0-5 $R_{11}$ and heterocyclyl comprising carbon atoms and 1 to 4 heteroatoms selected from N, $NR_9$, O, S, and substituted with 0-5 $R_{11}$;
- $R_2$ is selected from H, $C_{1-4}$alkyl, F, Cl, Br, CN, aryl, and heteroaryl;
- $R_3$ is selected from H and $C_{1-4}$alkyl;
- $R_4$ is selected from H, $C_{1-4}$alkyl F, Cl, Br, and CN;
- $R_5$ is selected from H, $C_{1-4}$alkyl substituted with 0-4 $R_e$, —(CH$_2$)$_r$—$C_{3-6}$ carbocyclyl substituted with 0-4 $R_e$, and —(CH$_2$)$_r$-heterocyclyl comprising carbon atoms and 1 to 3 heteroatoms selected from N, O, S, and substituted with 0-4 $R_e$;
- $R_7$ is aryl substituted with 0-3 $R_e$;
- $R_9$ is selected from H, —C(=O)$R_b$, $C_{1-6}$ alkyl substituted with 0-5 $R_e$, —(CH$_2$)$_r$—$C_{3-6}$carbocyclyl substituted with 0-5 $R_e$, and —(CH$_2$)$_r$-heterocyclyl substituted with 0-5 $R_e$;
- $R_{11}$, at each occurrence, is independently selected from H, F, —$NR_aR_a$, $C_{1-6}$ alkyl substituted with 0-5 $R_e$, —(CH$_2$)$_r$—$C_{3-6}$carbocyclyl substituted with 0-5 $R_e$, and —(CH$_2$)$_r$-heterocyclyl substituted with 0-5 $R_e$;
- $R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;
- $R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;
- $R_e$, at each occurrence, is independently selected from $C_{1-6}$ alkyl substituted with 0-5 $R_f$, —(CH$_2$)$_r$—$C_{3-6}$ cycloalkyl, F, Cl, Br, CN, NO$_2$, =O, $CO_2$H, —(CH$_2$)$_r$OR$_f$, SR$_f$, and —(CH$_2$)$_r$NR$_fR_f$;
- $R_f$, at each occurrence, is independently selected from H, F, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl; and
- r, at each occurrence, is independently selected from zero, 1, 2, 3, and 4.

10. A pharmaceutical composition comprising one or more compounds of claim 1 and a pharmaceutically acceptable carrier.

11. A method of inhibiting casein kinase Iδ/ε activity in a patient, comprising administering to a patient in need thereof, a therapeutically effective amount of one or more compounds according to claim 1.

* * * * *